United States Patent
Agarwal et al.

(10) Patent No.: US 11,529,337 B2
(45) Date of Patent: Dec. 20, 2022

(54) METHOD OF TREATING PAIN

(71) Applicant: VERTEX PHARMACEUTICALS INCORPORATED, Boston, MA (US)

(72) Inventors: Sagar Agarwal, Medford, MA (US); Cynthia Barber, Wayland, MA (US); Francoise Berlioz-Seux, Lexington, MA (US); Brenda Cirincione, Newtown, PA (US); James Jones, Norfolk, MA (US); Sandra Lechner, San Diego, CA (US); Marco Rizzo, Guilford, CT (US); David Stiles, Danvers, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 16/968,983

(22) PCT Filed: Feb. 12, 2019

(86) PCT No.: PCT/US2019/017662
§ 371 (c)(1),
(2) Date: Aug. 11, 2020

(87) PCT Pub. No.: WO2019/157505
PCT Pub. Date: Aug. 15, 2019

(65) Prior Publication Data
US 2021/0052610 A1    Feb. 25, 2021

Related U.S. Application Data

(60) Provisional application No. 62/780,281, filed on Dec. 16, 2018, provisional application No. 62/778,881, filed on Dec. 12, 2018, provisional application No. 62/629,308, filed on Feb. 12, 2018.

(51) Int. Cl.
*A61K 31/4412*   (2006.01)
*A61P 25/04*     (2006.01)
*A61K 31/661*    (2006.01)

(52) U.S. Cl.
CPC ........ *A61K 31/4412* (2013.01); *A61K 31/661* (2013.01); *A61P 25/04* (2018.01)

(58) Field of Classification Search
CPC ... A61K 31/661; A61K 31/4412; A61P 25/04; A61P 29/00
See application file for complete search history.

(56) References Cited

U.S. PATENT DOCUMENTS

| | | |
|---|---|---|
| 5,304,121 A | 4/1994 | Sahatjian |
| 5,886,026 A | 3/1999 | Hunter et al. |
| 6,099,562 A | 8/2000 | Ding et al. |
| 8,389,734 B2 | 3/2013 | Chen |
| 8,466,188 B2 | 6/2013 | Chafeev et al. |
| 8,486,950 B2 | 7/2013 | Goodacre et al. |
| 8,519,137 B2 | 8/2013 | Joshi |
| 8,779,197 B2 | 7/2014 | Chen |
| 8,841,483 B2 | 9/2014 | Joshi |
| 8,865,771 B2 | 10/2014 | Chen |
| 8,883,840 B2 | 11/2014 | Chafeev et al. |
| 9,051,270 B2 | 6/2015 | Hadida Ruah et al. |
| 9,108,903 B2 | 8/2015 | Hadida Ruah et al. |
| 9,139,529 B2 | 9/2015 | Hadida Ruah et al. |
| 9,163,008 B2 | 10/2015 | Ni et al. |
| 9,163,042 B2 | 10/2015 | Anderson et al. |
| 9,393,235 B2 | 7/2016 | Hadida Ruah et al. |
| 9,421,196 B2 | 8/2016 | Hadida Ruah et al. |
| 9,464,102 B2 | 10/2016 | Anderson et al. |
| 9,656,959 B2 | 5/2017 | Ni et al. |
| 9,758,483 B2 | 9/2017 | Hadida Ruah et al. |
| 9,783,501 B2 | 10/2017 | Hadida Ruah et al. |
| 9,828,397 B2 | 11/2017 | Anderson et al. |
| 10,087,143 B2 | 10/2018 | Hadida Ruah et al. |
| 10,253,054 B2 | 4/2019 | Anderson et al. |
| 10,647,661 B2 | 5/2020 | Ahmad et al. |
| 10,738,009 B2 | 8/2020 | Hadida Ruah et al. |
| 10,787,472 B2 | 9/2020 | Anderson et al. |
| 2007/0238733 A1 | 10/2007 | Joshi |
| 2009/0099233 A1 | 4/2009 | Joshi |
| 2009/0118333 A1 | 5/2009 | Chen |
| 2009/0118338 A1 | 5/2009 | Chen |
| 2010/0105906 A1 | 4/2010 | Bissantz et al. |
| 2013/0231370 A1 | 9/2013 | Chen |
| 2013/0303535 A1 | 11/2013 | Tsuboi et al. |
| 2014/0213616 A1 | 7/2014 | Hadida Ruah et al. |
| 2014/0221435 A1 | 8/2014 | Hadida Ruah et al. |
| 2014/0228371 A1 | 8/2014 | Hadida Ruah et al. |
| 2015/0166589 A1 | 6/2015 | Anderson et al. |

(Continued)

FOREIGN PATENT DOCUMENTS

| | | |
|---|---|---|
| CN | 101855210 | 10/2010 |
| CN | 101883758 | 11/2010 |

(Continued)

OTHER PUBLICATIONS

Akopian, A.N., L. Sivilotti, and J.N. Wood, A tetrodotoxin-resistant voltage-gated sodium channel expressed by sensory neurons. *Nature*, 1996. 379(6562): p. 257-62.
Black, J.A., et al., Multiple sodium channel isoforms and mitogen-activated protein kinases are present in painful human neuromas. *Ann Neurol*, 2008. 64(6) p. 644-53.
Blair, N.T. and B.P. Bean, Roles of tetrodotoxin (TTX)-sensitive $Na^+$ current, TTX-resistant $Na^+$ current, and $Ca^{2+}$ current in the action potentials of nociceptive sensory neurons. *J Neurosci.*, 2002. 22(23): p. 10277-90.
CAS Registry No. 1119379-37-1 (Mar. 12, 2009).
CAS Registry No. 1223014-19-4 (May 13, 2010).
CAS Registry No. 1241310-16-6 (Sep. 15, 2010).

(Continued)

*Primary Examiner* — Umamaheswari Ramachandran
(74) *Attorney, Agent, or Firm* — Barnes & Thornburg LLP

(57) ABSTRACT

Provided is a method of treating or lessening the severity of pain in a subject, comprising administering to the subject a compound of formula (I), defined as described herein, or a pharmaceutically acceptable salt thereof.

11 Claims, 3 Drawing Sheets

(56) References Cited

U.S. PATENT DOCUMENTS

| | | |
|---|---|---|
| 2015/0246028 A1 | 9/2015 | Hadida Ruah et al. |
| 2015/0328196 A1 | 11/2015 | Hadida Ruah et al. |
| 2015/0336945 A1 | 11/2015 | Hadida Ruah et al. |
| 2015/0376174 A1 | 12/2015 | Kawana et al. |
| 2016/0009743 A1 | 1/2016 | Anderson et al. |
| 2016/0152561 A1 | 6/2016 | Hadida Ruah et al. |
| 2016/0376295 A1 | 12/2016 | Anderson et al. |
| 2017/0037009 A1 | 2/2017 | Hadida Ruah et al. |
| 2018/0016235 A1 | 1/2018 | Hadida Ruah et al. |
| 2018/0044361 A1 | 2/2018 | Anderson et al. |
| 2019/0016671 A1 | 1/2019 | Ahmad |
| 2019/0248745 A1 | 8/2019 | Hadida Ruah et al. |
| 2019/0276483 A1 | 9/2019 | Anderson et al. |
| 2019/0343817 A1 | 11/2019 | Agarwal et al. |

FOREIGN PATENT DOCUMENTS

| | | |
|---|---|---|
| CN | 102264722 | 11/2011 |
| CN | 103429571 | 12/2013 |
| JP | 2003/034671 | 2/2003 |
| JP | 2005/531501 | 10/2005 |
| JP | 2011/500599 | 1/2011 |
| JP | 2011/500600 | 1/2011 |
| JP | 2012/506887 | 3/2012 |
| JP | 2016/506963 | 3/2016 |
| JP | 2016/508500 | 3/2016 |
| JP | 2016/525122 | 8/2016 |
| RU | 2010/118467 | 11/2011 |
| RU | 2010/118481 | 11/2011 |
| TW | 201331186 | 8/2013 |
| WO | WO 2002/008748 | 1/2002 |
| WO | WO 2003/068230 | 8/2003 |
| WO | WO 2005/013914 | 2/2005 |
| WO | WO 2006/011050 | 2/2006 |
| WO | WO 2007/120647 | 10/2007 |
| WO | WO 2008/135826 | 11/2008 |
| WO | WO 2009/049181 | 4/2009 |
| WO | WO 2009/049183 | 4/2009 |
| WO | WO 2010/072607 | 7/2010 |
| WO | WO 2010/137351 | 12/2010 |
| WO | WO 2011/026240 | 3/2011 |
| WO | WO 2011/140425 | 11/2011 |
| WO | WO 2012/106499 | 8/2012 |
| WO | WO 2012/112743 | 8/2012 |
| WO | WO 2012/116440 | 9/2012 |
| WO | WO 2012/125613 | 9/2012 |
| WO | WO 2013/061205 | 5/2013 |
| WO | WO 2013/109521 | 7/2013 |
| WO | WO 2013/114250 | 8/2013 |
| WO | WO 2013/131018 | 9/2013 |
| WO | WO 2013/132376 | 9/2013 |
| WO | WO 2014/120808 | 8/2014 |
| WO | WO 2014/120815 | 8/2014 |
| WO | WO 2014/120820 | 8/2014 |
| WO | WO 2015/010065 | 1/2015 |
| WO | WO 2015/089361 | 6/2015 |
| WO | WO 2018/213426 | 11/2018 |

OTHER PUBLICATIONS

CAS Registry No. 1252156-94-7 (Nov. 9, 2010).
CAS Registry No. 1258714-13-4 (Jan. 7, 2011).
CAS Registry No. 1258742-89-0 (Jan. 7, 2011).
CAS Registry No. 1281024-95-0 (Apr. 17, 2011).
CAS Registry No. 1281059-52-6 (Apr. 17, 2011).
CAS Registry No. 1281112-60-4 (Apr. 17, 2011).
CAS Registry No. 1287712-50-8 (Apr. 29, 2011).
CAS Registry No. 1301902-75-9 (May 29, 2011).
CAS Registry No. 1311734-41-4 (Jul. 7, 2011).
CAS Registry No. 1394673-41-6 (Sep. 18, 2012).
CAS Registry No. 1394698-15-7 (Sep. 18, 2012).
Catterall, W. A., Goldin, A. L., and Waxman, S. G., International Union of Pharmacology. XLVII. Nomenclature and structure-function relationships of voltage-gated sodium channels. *Pharmacol Rev* 57 (4), p. 397 (2005).
Chahine, M., Chatelier, A., Babich, O., and Krupp, J. J., Voltage-gated sodium channels in neurological disorders. *CNS Neurol Disord Drug Targets* 7 (2), p. 144-58 (2008).
Choi, J.S. and S.G. Waxman, Physiological interactions between $Na_v1.7$ and $Na_v1.8$ sodium channels: a computer simulation study. *J Neurophysiol.* 106(6): p. 3173-84.
Coward, K., et al., Immunolocalization of SNS/PN3 and NaN/SNS2 sodium channels in human pain states. *Pain*, 2000. 85(1-2): p. 41-50.
Dieleman, J.P., et al., Incidence rates and treatment of neuropathic pain conditions in the general population. *Pain*, 2008. 137(3): p. 681-8.
Dong, X.W., et al., Small interfering RNA-mediated selective knockdown of $Na_{(v)}1.8$ tetrodotoxin-resistant sodium channel reverses mechanical allodynia in neuropathic rats. *Neuroscience*, 2007. 146(2): p. 812-21.
England, S., Voltage-gated sodium channels: the search for subtype-selective analgesics. *Expert Opin Investig Drugs* 17 (12), p. 1849-64 (2008).
Huang, H.L., et al., Proteomic profiling of neuromas reveals alterations in protein composition and local protein synthesis in hyperexcitable nerves. *Mol Pain*, 2008. 4: p. 33.
International Search Report and Written Opinion of the International Searching Authority for International Application No. PCT/US2014/069916 (dated Feb. 12, 2015).
International Search Report and Written Opinion of the International Searching Authority for International Application No. PCT/US2014/013652 (dated Apr. 2, 2014).
Jarvis, M.F., et al., A-803467, a potent and selective $Na_v1.8$ sodium channel blocker, attenuates neuropathic and inflammatory pain in the rat. *Proc Natl Acad Sci. USA*, 2007. 104(20): p. 8520-5.
Joshi, S.K., et al., Involvement of the TTX-resistant sodium channel $Na_v1.8$ in inflammatory and neuropathic, but not post-operative, pain states. *Pain*, 2006. 123(1-2): pp. 75-82.
Krafte, D. S. and Bannon, A. W., Sodium channels and nociception: recent concepts and therapeutic opportunities. *Curr Opin Pharmacol* 7 (1), p. 1-7 (2007).
Lai, J., et al., Inhibition of neuropathic pain by decreased expression of the tetrodotoxin-resistant sodium channel, $Na_v1.8$. *Pain*, 2002. 95(1-2): p. 143-52.
Qiu, F., et al., Increased expression of tetrodotoxin-resistant sodium channels $Na_v1.8$ and $Na_v1.9$ within dorsal root ganglia in a rat model of bone cancer pain. *Neurosci. Lett.* 512(2): p. 61-6).
Renganathan, M., T.R. Cummins, and S.G. Waxman, Contribution of $Na_{(v)}1.8$ sodium channels to action potential electrogenesis in DRG neurons. Neurophysiol., 2001. 86(2): p. 629-40.
Roza, C., et al., The tetrodotoxin-resistant $Na^+$ channel $Na_v1.8$ is essential for the expression of spontaneous activity in damaged sensory axons of mice. *J. Physiol.*, 2003. 550(Pt 3): p. 921-6.
Ruangsri, S., et al., Relationship of axonal voltage-gated sodium channel 1.8 ($Na_v1.8$) mRNA accumulation to sciatic nerve injury-induced painful neuropathy in rats. *J Biol Chem.* 286(46): p. 39836-47.
Rush, A.M. and T.R. Cummins, Painful Research: Identification of a Small-Molecule Inhibitor that Selectively Targets Nav1.8 Sodium Channels. *Mol Interv*, 2007. 7(4): p. 192-5).
Rush, A.M., et al., A single sodium channel mutation produces hyper- or hypoexcitability in different types of neurons. *Proc Natl Acad Sci USA*, 2006. 103(21): p. 8245-50.
Soderpalm, B., Anticonvulsants: aspects of their mechanisms of action. *Eur J Pain 6 Suppl A*, p. 3-9(2002).
Strickland, I.T., et al., Changes in the expression of NaV1.7, $Na_v1.8$ and $Na_v1.9$ in a distinct population of dorsal root ganglia innervating the rat knee joint in a model of chronic inflammatory joint pain. *Eur J Pain*, 2008. 12(5): p. 564-72.
Sun, W., et al., Reduced conduction failure of the main axon of polymodal nociceptive C-fibres contributes to painful diabetic neuropathy in rats. *Brain*. 135(Pt 2): p. 359-75.
Wang, G. K., Mitchell, J., and Wang, S. Y., Block of persistent late $Na^+$ currents by antidepressant sertraline and paroxetine. *J Membr Biol* 222 (2), p. 79-90 (2008).

(56) References Cited

OTHER PUBLICATIONS

Yiangou, Y., et al., SNS/PN3 and SNS2/NaN sodium channel-like immunoreactivity in human adult and neonate injured sensory nerves. *FEBS Lett*, 2000. 467(2-3): p. 249-52.
U.S. National Library of Medicine (Oct. 3, 2016) *A Study of the Efficacy and Safety of VX-150 in Subjects With Osteoarthritis of the Knee* (ClinicalTrials.gov Identifier NCT02660424).
U.S. National Library of Medicine (Apr. 15, 2016). *A Study of the Efficacy and Safety of VX-150 in Subjects With Osteoarthritis of the Knee* (ClinicalTrials.gov Identifier NCT02660424).
U.S. National Library of Medicine (May 19, 2016). *A Study of the Efficacy and Safety of VX-150 in Subjects With Osteoarthritis of the Knee* (ClinicalTrials.gov Identifier NCT02660424).
U.S. National Library of Medicine (Jun. 30, 2016). *A Study of the Efficacy and Safety of VX-150 in Subjects With Osteoarthritis of the Knee* (ClinicalTrials.gov Identifier NCT02660424).
U.S. National Library of Medicine (Oct. 4, 2016). *A Study of the Efficacy and Safety of VX-150 in Subjects With Osteoarthritis of the Knee* (ClinicalTrials.gov Identifier NCT02660424).
U.S. National Library of Medicine (Jul. 2, 2017). *A Study to Evaluate Efficacy and Safety of VX-150 in Subjects With Acute Pain Following Bunionectomy* (ClinicalTrials.gov Identifier NCT03206749).
U.S. National Library of Medicine (Jul. 11, 2017). *A Study to Evaluate Efficacy and Safety of VX-150 in Subjects With Acute Pain Following Bunionectomy* (ClinicalTrials.gov Identifier NCT03206749).
U.S. National Library of Medicine (Aug. 18, 2017). *A Study to Evaluate Efficacy and Safety of VX-150 in Subjects With Acute Pain Following Bunionectomy* (ClinicalTrial.gov Identifier NCT03206749).
U.S. National Library of Medicine (Oct. 9, 2017). *A Study to Evaluate the Efficacy and Safety of VX-150 in Treating Subjects With Pain Caused by Small Fiber Neuropathy* (ClinicalTrial.gov Identifier NCT03304522).
U.S. National Library of Medicine (Oct. 25, 2017). *A Study to Evaluate the Efficacy and Safety of VX-150 in Treating Subjects With Pain Caused by Small Fiber Neuropathy* (ClinicalTrial.gov Identifier NCT03304522).
U.S. National Library of Medicine (Dec. 2, 2017). *A Study to Evaluate the Efficacy and Safety of VX-150 in Treating Subjects With Pain Caused by Small Fiber Neuropathy* (ClinicalTrial.gov Identifier NCT03304522).
U.S. National Library of Medicine (Dec. 18, 2017). *A Study to Evaluate the Efficacy and Safety of VX-150 in Treating Subjects With Pain Caused by Small Fiber Neuropathy* (ClinicalTrial.gov Identifier NCT03304522).
U.S. National Library of Medicine (Dec. 20, 2017). *A Study to Evaluate the Efficacy and Safety of VX-150 in Treating Subjects With Pain Caused by Small Fiber Neuropathy* (ClinicalTrial.gov Identifier NCT03304522).
U.S. National Library of Medicine (Jan. 5, 2018). *A Study to Evaluate Efficacy and Safety of VX-150 in Subjects With Acute Pain Following Bunionectomy* (ClinicalTrial.gov Identifier NCT03206749).
U.S. National Library of Medicine (Feb. 8, 2018). *A Study to Evaluate the Efficacy and Safety of VX-150 in Treating Subjects With Pain Caused by Small Fiber Neuropathy* (ClinicalTrial.gov Identifier NCT03304522).
U.S. National Library of Medicine (Mar. 13, 2018). *A Study to Evaluate the Efficacy and Safety of VX-150 in Treating Subjects With Pain Caused by Small Fiber Neuropathy* (ClinicalTrial.gov Identifier NCT03304522).
U.S. National Library of Medicine (Jun. 6, 2018). *A Study to Evaluate the Efficacy and Safety of VX-150 in Treating Subjects With Pain Caused by Small Fiber Neuropathy* (ClinicalTrial.gov Identifier NCT03304522).
U.S. National Library of Medicine (Aug. 24, 2018). *A Study to Evaluate the Efficacy and Safety of VX-150 in Treating Subjects With Pain Caused by Small Fiber Neuropathy* (ClinicalTrial.gov Identifier NCT03304522).
U.S. National Library of Medicine (Oct. 1, 2018). *A Study to Evaluate the Efficacy and Safety of VX-150 in Treating Subjects With Pain Caused by Small Fiber Neuropathy* (ClinicalTrial.gov Identifier NCT03304522).
U.S. National Library of Medicine (Nov. 14, 2018). *A Study to Evaluate the Efficacy and Safety of VX-150 in Treating Subjects With Pain Caused by Small Fiber Neuropathy* (ClinicalTrial.gov Identifier NCT03304522).
U.S. National Library of Medicine (Dec. 3, 2018). *A Study to Evaluate Efficacy and Safety of VX-150 in Subjects With Acute Pain Following Bunionectomy* (ClinicalTrial.gov Identifier NCT03206749).
U.S. National Library of Medicine (Dec. 4, 2018). *A Dose-ranging Study to Evaluate Efficacy and Safety of VX-150 in Subjects With Acute Pain Following Bunionectomy* (ClinicalTrial.gov Identifier NCT03764072).
U.S. National Library of Medicine (Dec. 10, 2018). *A Study to Evaluate the Efficacy and Safety of VX-150 in Treating Subjects With Pain Caused by Small Fiber Neuropathy* (ClinicalTrial.gov Identifier NCT03304522).
U.S. National Library of Medicine (Dec. 24, 2018). *A Study to Evaluate Efficacy and Safety of VX-150 in Subjects With Acute Pain Following Bunionectomy* (ClinicalTrial.gov Identifier NCT03206749).
U.S. National Library of Medicine (Feb. 18, 2019). *A Study to Evaluate Efficacy and Safety of VX-150 in Subjects With Acute Pain Following Bunionectomy* (ClinicalTrial.gov Identifier NCT03206749).
U.S. National Library of Medicine (Oct. 14, 2019). *A Study to Evaluate the Efficacy and Safety of VX-150 in Treating Subjects with Pain Caused by Small Fiber Neuropathy.* (ClinicalTrials.gov Identifier NCT03304522).
U.S. National Library of Medicine (Jan. 17, 2020) *A Dose-ranging Study to Evaluate Efficacy and Safety of VX-150 in Subjects with Acute Pain Following Bunionectomy.* (ClinicalTrials.gov Identifier NCT03764072).
Howard C. Ansel Ph.D., Loyd V. Allen, Jr. Ph.D., and Nicholas G. Popovich, Ph.D., "New Drug Development and Approval Process, Drug Dosage and Terminology" *Pharmaceutical Dosage Forms and Drug Delivery Systems*, Seventh Edition, 1999, pp. 48-53.
U.S. Office Action dated Dec. 2, 2019 for U.S. Appl. No. 16/273,804, 10 pages.

METHOD OF TREATING PAIN

CROSS-REFERENCE TO RELATED APPLICATIONS

This application claims the benefit of U.S. Provisional Application No. 62/629,308, filed Feb. 12, 2018, U.S. Provisional Application No. 62/778,881, filed Dec. 12, 2018, and U.S. Provisional Application No. 62/780,281, filed Dec. 16, 2018, each of which is incorporated by reference in its entirety.

BACKGROUND

Pain is a protective mechanism that allows healthy animals to avoid tissue damage and to prevent further damage to injured tissue. Managing pain in the clinical setting, in both acute and chronic clinical settings, remain a high unmet need. In addition to acute pain, there are many conditions where chronic pain persists beyond its protective role (neuropathic pain) where patients would benefit from inhibition of pain. Neuropathic pain is a form of chronic pain caused by an injury to the sensory nerves (Dieleman, J. P., et al., Incidence rates and treatment of neuropathic pain conditions in the general population. *Pain*, 2008. 137(3): p. 681-8). Neuropathic pain can be divided into two categories, pain caused by generalized metabolic damage to the nerve and pain caused by a discrete nerve injury. The metabolic neuropathies include post herpetic neuropathy, diabetic neuropathy, and drug-induced neuropathy. Discrete nerve injuries indications include post amputation pain, post-surgical nerve injury pain, and nerve entrapment injuries like neuropathic back pain.

Current pain therapies suffer from poor efficacy and a high risk of adverse events (AEs). For example, lidocaine (a nonselective sodium channel blocker) may effectively reduce pain, but its utility is limited because of prominent side effects when given at dose levels required for pain relief. Opioid pain medications have a high abuse liability, leading to frequent deaths due to overdose. In addition, opioid-induced hyperalgesia also limits the long term use of opioids. Opioid-induced hyperalgesia is encountered regularly in clinical practice and creates significant challenges in pain management. The limited treatment options for pain, combined with a growing awareness of the risks of the current standards of care, underscore the need for new pain management therapies.

Voltage-gated sodium channels ($Na_V$'s) are involved in pain signaling. $Na_V$'s are biological mediators of electrical signaling as they mediate the rapid upstroke of the action potential of many excitable cell types (e.g. neurons, skeletal myocytes, cardiac myocytes). The evidence for the role of these channels in normal physiology, the pathological states arising from mutations in sodium channel genes, preclinical work in animal models, and the clinical pharmacology of known sodium channel modulating agents all point to the central role of $Na_V$'s in pain sensation (Rush, A. M. and T. R. Cummins, *Painful Research: Identification of a Small-Molecule Inhibitor that Selectively Targets $Na_V1.8$ Sodium Channels*. Mol. Interv., 2007. 7(4): p. 192-5); England, S., Voltage-gated sodium channels: the search for subtype-selective analgesics. *Expert Opin. Investig. Drugs* 17 (12), p. 1849-64 (2008); Krafte, D. S. and Bannon, A. W., Sodium channels and nociception: recent concepts and therapeutic opportunities. *Curr. Opin. Pharmacol.* 8 (1), p. 50-56 (2008)). $Na_V$'s mediate the rapid upstroke of the action potential of many excitable cell types (e.g. neurons, skeletal myocytes, cardiac myocytes), and thus are involved in the initiation of signaling in those cells (Hille, Bertil, *Ion Channels of Excitable Membranes*, Third ed. (Sinauer Associates, Inc., Sunderland, Mass., 2001)). Because of the role $Na_V$'s play in the initiation and propagation of neuronal signals, antagonists that reduce $Na_V$ currents can prevent or reduce neural signaling and $Na_V$ channels have been considered likely targets to reduce pain in conditions where hyper-excitability is observed (Chahine, M., Chatelier, A., Babich, O., and Krupp, J. J., Voltage-gated sodium channels in neurological disorders. *CNS Neurol. Disord. Drug Targets* 7 (2), p. 144-58 (2008)). Several clinically useful analgesics have been identified as inhibitors of $Na_V$ channels. The local anesthetic drugs such as lidocaine block pain by inhibiting $Na_V$ channels, and other compounds, such as carbamazepine, lamotrigine, and tricyclic antidepressants that have proven effective at reducing pain have also been suggested to act by sodium channel inhibition (Soderpalm, B., Anticonvulsants: aspects of their mechanisms of action. *Eur. J. Pain* 6 Suppl. A, p. 3-9 (2002); Wang, G. K., Mitchell, J., and Wang, S. Y., Block of persistent late $Na^+$ currents by antidepressant sertraline and paroxetine. *J. Membr. Biol.* 222 (2), p. 79-90 (2008)).

The $Na_V$'s form a subfamily of the voltage-gated ion channel super-family and comprises 9 isoforms, designated $Na_V1.1$-$Na_V1.9$. The tissue localizations of the nine isoforms vary. $Na_V1.4$ is the primary sodium channel of skeletal muscle, and $Na_V1.5$ is primary sodium channel of cardiac myocytes. $Na_V$'s 1.7, 1.8 and 1.9 are primarily localized to the peripheral nervous system, while $Na_V$'s 1.1, 1.2, 1.3, and 1.6 are neuronal channels found in both the central and peripheral nervous systems. The functional behaviors of the nine isoforms are similar but distinct in the specifics of their voltage-dependent and kinetic behavior (Catterall, W. A., Goldin, A. L., and Waxman, S. G., International Union of Pharmacology. XLVII. Nomenclature and structure-function relationships of voltage-gated sodium channels. *Pharmacol. Rev.* 57 (4), p. 397 (2005)).

Upon their discovery, $Na_V1.8$ channels were identified as likely targets for analgesia (Akopian, A. N., L. Sivilotti, and J. N. Wood, A tetrodotoxin-resistant voltage-gated sodium channel expressed by sensory neurons. *Nature*, 1996. 379 (6562): p. 257-62). Since then, $Na_V1.8$ has been shown to be a carrier of the sodium current that maintains action potential firing in small DRG neurons, supporting its potential as a target for multiple indications or across multiple pain types (Blair, N. T. and B. P. Bean, Roles of tetrodotoxin (TTX)-sensitive Na+ current, TTX-resistant $Na^+$ current, and $Ca^{2+}$ current in the action potentials of nociceptive sensory neurons. *J. Neurosci.*, 2002. 22(23): p. 10277-90). $Na_V1.8$ is involved in spontaneous firing in damaged neurons, like those that drive neuropathic pain (Roza, C., et al., The tetrodotoxin-resistant $Na^+$ channel $Na_V1.8$ is essential for the expression of spontaneous activity in damaged sensory axons of mice. *J. Physiol.*, 2003. 550(Pt 3): p. 921-6; Jarvis, M. F., et al., A-803467, a potent and selective $Na_V1.8$ sodium channel blocker, attenuates neuropathic and inflammatory pain in the rat. *Proc. Natl. Acad. Sci. USA*, 2007. 104(20): p. 8520-5; Joshi, S. K., et al., Involvement of the TTX-resistant sodium channel $Na_V1.8$ in inflammatory and neuropathic, but not post-operative, pain states. *Pain*, 2006. 123(1-2): pp. 75-82; Lai, J., et al., Inhibition of neuropathic pain by decreased expression of the tetrodotoxin-resistant sodium channel, $Na_V1.8$. *Pain*, 2002. 95(1-2): p. 143-52; Dong, X. W., et al., Small interfering RNA-mediated selective knockdown of $Na(_V)1.8$ tetrodotoxin-resistant sodium channel reverses mechanical allodynia in neuropathic rats.

Neuroscience, 2007. 146(2): p. 812-21; Huang, H. L., et al., Proteomic profiling of neuromas reveals alterations in protein composition and local protein synthesis in hyper-excitable nerves. *Mol. Pain*, 2008. 4: p. 33; Black, J. A., et al., Multiple sodium channel isoforms and mitogen-activated protein kinases are present in painful human neuromas. *Ann. Neurol.*, 2008. 64(6): p. 644-53; Coward, K., et al., Immunolocalization of SNS/PN3 and NaN/SNS2 sodium channels in human pain states. *Pain*, 2000. 85(1-2): p. 41-50; Yiangou, Y., et al., SNS/PN3 and SNS2/NaN sodium channel-like immunoreactivity in human adult and neonate injured sensory nerves. *FEBS Lett.*, 2000. 467(2-3): p. 249-52; Ruangsri, S., et al., Relationship of axonal voltage-gated sodium channel 1.8 ($Na_V1.8$) mRNA accumulation to sciatic nerve injury-induced painful neuropathy in rats. *J. Biol. Chem.* 286(46): p. 39836-47). The small DRG neurons where $Na_V1.8$ is expressed include the nociceptors involved in pain signaling $Na_V1.8$ mediates large amplitude action potentials in small neurons of the dorsal root ganglia (Blair, N. T. and B. P. Bean, Roles of tetrodotoxin (TTX)-sensitive $Na^+$ current, TTX-resistant $Na^+$ current, and $Ca^{2+}$ current in the action potentials of nociceptive sensory neurons. *J. Neurosci.*, 2002. 22(23): p. 10277-90). $Na_V1.8$ is necessary for rapid repetitive action potentials in nociceptors, and for spontaneous activity of damaged neurons. (Choi, J. S. and S. G. Waxman, Physiological interactions between $Na_V1.7$ and $Na_V1.8$ sodium channels: a computer simulation study. *J. Neurophysiol.* 106(6): p. 3173-84; Renganathan, M., T. R. Cummins, and S. G. Waxman, Contribution of $Na_{(V)}1.8$ sodium channels to action potential electrogenesis in DRG neurons. *J. Neurophysiol.*, 2001. 86(2): p. 629-40; Roza, C., et al., The tetrodotoxin-resistant $Na^+$ channel $Na_V1.8$ is essential for the expression of spontaneous activity in damaged sensory axons of mice. *J. Physiol.*, 2003. 550(Pt 3): p. 921-6). In depolarized or damaged DRG neurons, $Na_V1.8$ appears to be a driver of hyper-excitablility (Rush, A. M., et al., A single sodium channel mutation produces hyper- or hypoexcitability in different types of neurons. *Proc. Natl. Acad. Sci. USA,* 2006. 103(21): p. 8245-50). In some animal pain models, $Na_V1.8$ mRNA expression levels have been shown to increase in the DRG (Sun, W., et al., Reduced conduction failure of the main axon of polymodal nociceptive C-fibers contributes to painful diabetic neuropathy in rats. *Brain,* 135(Pt 2): p. 359-75; Strickland, I. T., et al., Changes in the expression of $Na_V1.7$, $Na_V1.8$ and $Na_V1.9$ in a distinct population of dorsal root ganglia innervating the rat knee joint in a model of chronic inflammatory joint pain. *Eur. J. Pain*, 2008. 12(5): p. 564-72; Qiu, F., et al., Increased expression of tetrodotoxin-resistant sodium channels $Na_V1.8$ and $Na_V1.9$ within dorsal root ganglia in a rat model of bone cancer pain. *Neurosci. Lett.*, 512(2): p. 61-6).

US Publication No. 2014/0213616 A1 discloses a pyridone amide compound useful as an inhibitor of $Na_V1.8$ sodium channels and known by the chemical name 2-(4-fluoro-2-methylphenoxy)-N-(2-oxo-1,2-dihydropyridin-4-yl)-4-(trifluoromethyl)benzamide. US Publication No. 2015/0166589 A1 discloses a prodrug of the foregoing compound, which is known by the chemical name (4-(2-(4-fluoro-2-methylphenoxy)-4-(trifluoromethyl)benzamido)-2-oxopyridin-1(2H)-yl)methyl dihydrogen phosphate.

SUMMARY

In one aspect, the disclosure relates to a method of treating or lessening the severity of pain in a subject, comprising administering to the subject a compound of formula (I)

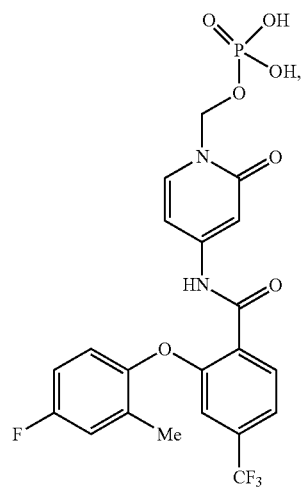

or a pharmaceutically acceptable salt thereof.

DETAILED DESCRIPTION

Definitions

Figure 1:
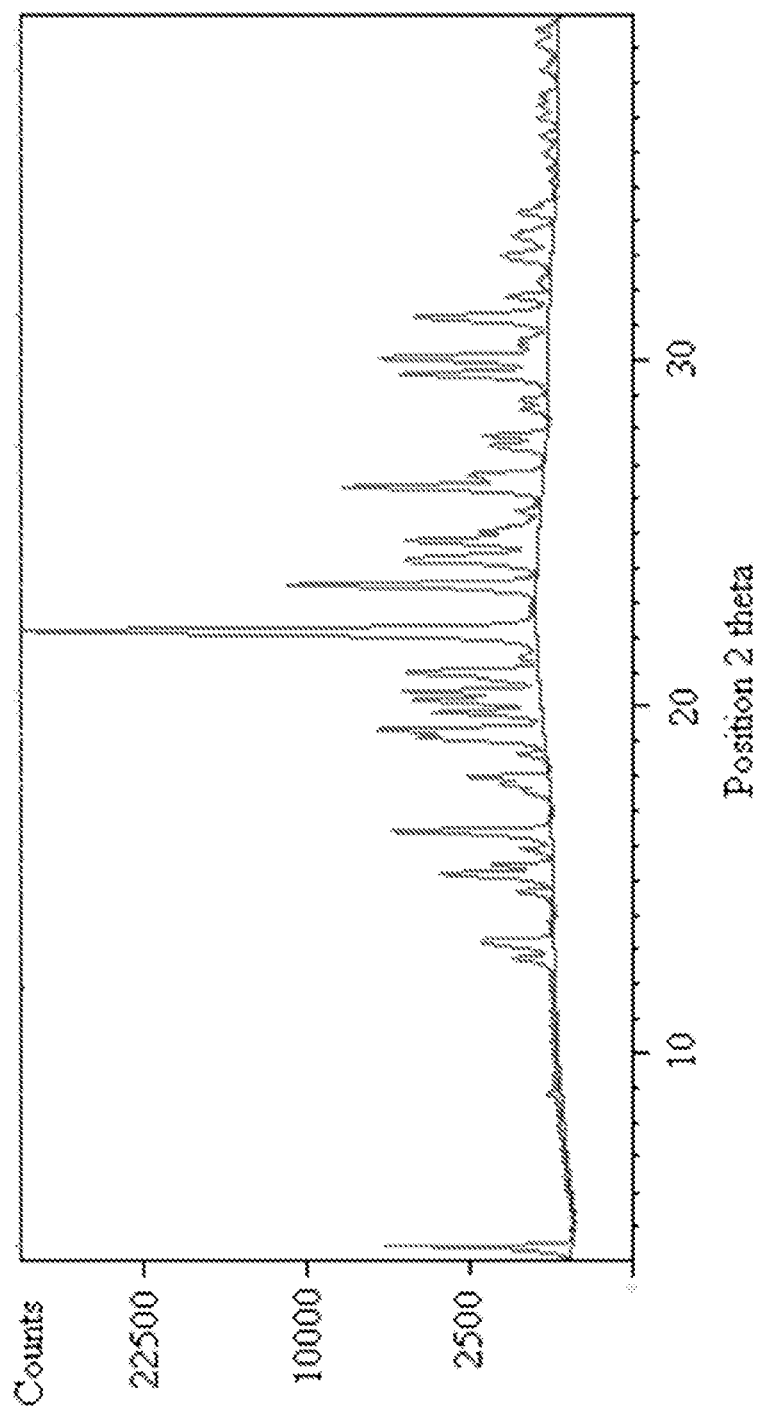
FIG. 1 is an X-ray powder diffraction pattern of solid Form B of (4-(2-(4-fluoro-2-methylphenoxy)-4-(trifluoromethyl)benzamido)-2-oxopyridin-1(2H)-yl)methyl dihydrogen phosphate.

The chemical elements are identified herein in accordance with the Periodic Table of the Elements, CAS version, Handbook of Chemistry and Physics, 75th Ed. Additionally, general principles of organic chemistry are described in "Organic Chemistry," Thomas Sorrell, University Science Books, Sausalito: 1999, and "March's Advanced Organic Chemistry," 5th Ed.: Smith, M. B. and March, J., John Wiley & Sons, New York: 2001, the entire contents of which are hereby incorporated by reference.

As used herein, the term "compound of formula (I)," and the structure and chemical name corresponding to the "compound of formula (I)," refer to a collection of molecules having identical chemical structures, namely the structure corresponding to the "compound of formula (I)," except that there may be isotopic variation among the constituent atoms of the molecules. The term "compound of formula (I)" includes such a collection of molecules without regard to the purity of a given sample containing the collection of molecules. Thus, the term "compound of formula (I)" includes such a collection of molecules in pure form or in a mixture (e.g., solution, suspension, or colloid) with one or more other substances.

In the specification and claims, unless otherwise specified, any atom not specifically designated as a particular isotope in the compound of formula (I) is meant to represent any stable isotope of the specified element. In the Examples, where an atom is not specifically designated as a particular isotope, no effort was made to enrich that atom in a particular isotope, and therefore a person of ordinary skill in the art would understand that such atom likely was present at approximately the natural abundance isotopic composition of the specified element.

As used herein, the term "stable," when referring to an isotope, means that the isotope is not known to undergo spontaneous radioactive decay. Stable isotopes include, but are not limited to, the isotopes for which no decay mode is identified in V. S. Shirley & C. M. Lederer, Isotopes Project, Nuclear Science Division, Lawrence Berkeley Laboratory, Table of Nuclides (January 1980).

As used herein in the specification and claims, "H" refers to hydrogen and includes any stable isotope of hydrogen, namely $^1$H and D. In the Examples, where an atom is designated as "H," no effort was made to enrich that atom in a particular isotope of hydrogen, and therefore a person of ordinary skill in the art would understand that such hydrogen atom likely was present at approximately the natural abundance isotopic composition of hydrogen.

In some embodiments, the compound of formula (I), or a pharmaceutically acceptable salt thereof, includes each constituent atom at approximately the natural abundance isotopic composition of the specified element.

In some embodiments, the compound of formula (I), or a pharmaceutically acceptable salt thereof, includes one or more atoms having an atomic mass or mass number which differs from the atomic mass or mass number of the most abundant isotope of the specified element ("isotope-labelled" compound or salt). Examples of stable isotopes which are commercially available and suitable for the invention include without limitation isotopes of hydrogen, carbon, nitrogen, oxygen, and phosphorus, for example $^2$H, $^{13}$C, $^{15}$N, $^{18}$O, $^{17}$O, and $^{31}$P, respectively.

The terms "compound of formula (I)" and "pharmaceutically acceptable salt thereof" include the compound of formula (I) and any pharmaceutically acceptable salt thereof in any form, including any solid form thereof (including any amorphous or crystalline form thereof), any solvate, hydrate, or cocrystal form thereof, and any solution or suspension thereof.

As used herein, the term "subject" or "patient" means an animal, preferably a mammal, and most preferably a human.

As used herein, the term "amount," when referring to an amount of the compound of formula (I), or a pharmaceutically acceptable salt thereof, administered to a subject, refers to the mass of an equimolar amount of (4-(2-(4-fluoro-2-methylphenoxy)-4-(trifluoromethyl)benzamido)-2-oxopyridin-1(2H)-yl)methyl dihydrogen phosphate, regardless of the actual mass of any salt, solvate, hydrate, or cocrystal form that may be administered.

As used herein, and unless otherwise specified, the term "per day," when referring to an amount of the compound of formula (I), or a pharmaceutically acceptable salt thereof, administered to a subject, refers to the amount of the compound of formula (I), or a pharmaceutically acceptable salt thereof, administered to the subject on at least one day during a course of treatment. Unless otherwise specified, it will be understood that the compound of formula (I), or a pharmaceutically acceptable salt thereof, may be administered to the subject in a different amount on one or more other day(s) during the course of treatment.

As used herein, the term "first day" refers to the first day on which the compound of formula (I), or a pharmaceutically acceptable salt thereof, is administered during a course of treatment.

As used herein, the term "course of treatment," when referring to the compound of formula (I), or a pharmaceutically acceptable salt thereof, refers to the administration of one or more doses of the compound or salt during a period of time that is separate from any earlier or later administration of the compound or salt. Typically, the compound of formula (I), its parent compound, and any metabolites thereof are substantially eliminated from a subject's systemic circulation between courses of treatment.

As used herein, the term "parent compound" refers to the biologically active entity that is released in vivo following administration of a prodrug. The parent compound of the compound of formula (I) is 2-(4-fluoro-2-methylphenoxy)-N-(2-oxo-1,2-dihydropyridin-4-yl)-4-(trifluoromethyl)benzamide.

As used herein, the term "dose," when referring to the administration of the compound of formula (I), or a pharmaceutically acceptable salt thereof, refers to an amount of the compound or salt administered in a discrete period of time, separate from other amounts of the compound or salt that may be administered at other times during the same day or course of treatment. When a dose is administered orally, the dose may be administered in a single tablet, capsule, or other oral dosage form, or in multiple such dosage forms.

As used herein, the term "first dose" refers to the first dose of the compound of formula (I), or a pharmaceutically acceptable salt thereof, that is administered on a given day or in a given course of treatment, as the context dictates.

As used herein, the term "subsequent dose" refers to any dose of the compound of formula (I), or a pharmaceutically acceptable salt thereof, that is administered after the first dose on a given day or in a given course of treatment, as the context dictates.

As used herein, the term "baseline pain score" refers to a subject's pain score, such as a score on the 11-point Numeric Pain Rating Scale or Verbal Categorical Rating Scale, prior to beginning a course of treatment with the compound of formula (I), or a pharmaceutically acceptable salt thereof.

As used herein, the term "11-point Numeric Pain Rating Scale" refers to a pain rating scale on which a subject rates his or her pain intensity on a scale of 0 to 10, where a score of 0 denotes no pain, and a score of 10 denotes the worst pain intensity imaginable.

As used herein, the term "Verbal Categorical Rating Scale" refers to a pain rating scale on which a subject rates his or her pain intensity as none, mild, moderate, or severe.

Medical Uses of the Compound of Formula (I) or a Pharmaceutically Acceptable Salt Thereof.

In one aspect, the disclosure relates to a method of treating or lessening the severity of pain in a subject, comprising administering to the subject a compound of formula (I), or a pharmaceutically acceptable salt thereof.

In another aspect, the disclosure relates to a compound of formula (I), or a pharmaceutically acceptable salt thereof, for use in a method of treating or lessening the severity of pain in a subject, comprising administering to the subject the compound of formula (I), or the pharmaceutically acceptable salt thereof.

In another aspect, the disclosure relates to a composition comprising a compound of formula (I), or a pharmaceutically acceptable salt thereof, for use in a method of treating or lessening the severity of pain in a subject, wherein the composition is prepared for administration of the compound of formula (I), or the pharmaceutically acceptable salt thereof, to the subject.

Dosing Schedules

The compound of formula (I), or a pharmaceutically acceptable salt thereof, may be administered in any amount appropriate to treat or lessen the severity of pain in the subject. In some embodiments, the compound of formula (I), or a pharmaceutically acceptable salt thereof is administered in an amount of 100 mg to 5000 mg per day, or 500 mg to 5000 mg per day, or 600 mg to 4600 mg per day, or 700 mg to 4200 mg per day, or 800 mg to 3800 mg per day, or 900 mg to 3400 mg per day, or 1000 mg to 3000 mg per day, or 1100 mg to 2850 mg per day, or 1200 mg to 2700 mg per day, or 1300 mg to 2550 mg per day, or 1400 mg to 2400 mg per day, or 1500 mg to 2250 mg per day, or 1000 mg to 3500 mg per day, or 1100 mg to 3400 mg per day, or 1200 mg to 3300 mg per day, or 1300 mg to 3200 mg per day, or 1400 mg to 3100 mg per day, or 1500 mg to 3000 mg per day, or 1600 mg to 2900 mg per day, or 1700 mg to 2800 mg per day, or 1800 mg to 2700 mg per day, or 1900 mg to 2600 mg per day, or 2000 mg to 2500 mg per day, or 2100 mg to 2400 mg per day, or 2200 mg to 2300 mg per day, or about 2250 mg per day, or 500 mg to 2500 mg per day, or 600 mg to 2400 mg per day, or 700 mg to 2300 mg per day, or 800 mg to 2200 mg per day, or 900 mg to 2100 mg per day, or 1000 mg to 2000 mg per day, or 1100 mg to 1900 mg per day, or 1200 mg to 1800 mg per day, or 1300 mg to 1700 mg per day, or 1400 mg to 1600 mg per day, or 1450 mg to 1550 mg per day, or about 1500 mg per day, or 100 mg to 2000 mg per day, or 100 mg to 500 mg per day, or 150 mg to 400 mg per day, or 200 mg to 300 mg per day, or about 250 mg per day, or 500 mg to 2000 mg per day, or 600 mg to 1800 mg per day, or 700 mg to 1600 mg per day, or 800 mg to 1400 mg per day, or 900 mg to 1200 mg per day, or about 1000 mg per day, or 250 mg to 1500 mg per day, or 500 to 1000 mg per day, or about 750 mg per day, or 250 mg to 1000 mg per day, or 250 to 750 mg per day, or about 500 mg per day, or 500 mg to 2000 mg per day, or 750 mg to 1750 mg per day, or 1000 mg to 1500 mg per day, or 1100 mg to 1400 mg per day, or 1200 mg to 1300 mg per day, or about 1250 mg per day, or 250 mg to 1250 mg per day, or 500 mg to 1000 mg per day, or 600 mg to 900 mg per day, or 700 mg to 800 mg per day, or about 750 mg per day, or 250 mg to 1750 mg per day, or 500 mg to 1500 mg per day, or 750 mg to 1250 mg per day.

The compound of formula (I), or a pharmaceutically acceptable salt thereof, when administered for multiple days, may be administered in the same or different amounts each day.

In some embodiments, the compound of (I), or a pharmaceutically acceptable salt thereof, is administered in the same amount each day. In some embodiments, the compound of formula (I), or a pharmaceutically acceptable salt thereof, is administered in an amount of 100 mg to 2000 mg per day, or 100 mg to 500 mg per day, or 150 mg to 400 mg per day, or 200 mg to 300 mg per day, or about 250 mg per day, or 500 mg to 2000 mg per day, or 600 mg to 1800 mg per day, or 700 mg to 1600 mg per day, or 800 mg to 1400 mg per day, or 900 mg to 1200 mg per day, or about 1000 mg per day, or 500 mg to 2000 mg per day, or 750 mg to 1750 mg per day, or 1000 mg to 1500 mg per day, or 1100 mg to 1400 mg per day, or 1200 mg to 1300 mg per day, or about 1250 mg per day, or 250 mg to 1250 mg per day, or 500 mg to 1000 mg per day, or 600 mg to 900 mg per day, or 700 mg to 800 mg per day, or about 750 mg per day, or 250 mg to 1750 mg per day, or 500 mg to 1500 mg per day, or 750 mg to 1250 mg per day.

In some embodiments, the compound of formula (I), or a pharmaceutically acceptable salt thereof, is administered in different amounts on the first day and after the first day. In some embodiments, the compound of formula (I), or a pharmaceutically acceptable salt thereof, is administered in an amount of 1500 mg to 3000 mg, or 1500 mg to 3000 mg, or 1600 mg to 2900 mg, or 1700 mg to 2800 mg, or 1800 mg to 2700 mg, or 1900 mg to 2600 mg, or 2000 mg to 2500 mg, or 2100 mg to 2400 mg, or 2200 mg to 2300 mg, or about 2250 mg on a first day and in an amount of 1000 mg to 2000 mg per day, or 1100 mg to 1900 mg per day, or 1200 mg to 1800 mg per day, or 1300 mg to 1700 mg per day, or 1400 mg to 1600 mg per day, or 1450 mg to 1550 mg per day, or about 1500 mg per day after the first day.

In some embodiments, the compound of formula (I), or a pharmaceutically acceptable salt thereof, is administered in an amount of 2000 mg to 2500 mg, or 2100 mg to 2400 mg, or 2200 mg to 2300 mg, or about 2250 mg on the first day.

In some embodiments, the compound of formula (I), or a pharmaceutically acceptable salt thereof, is administered in an amount of 1250 mg to 1750 mg per day, or 1300 mg to 1700 mg per day, or 1350 mg to 1650 mg per day, or 1400 mg to 1600 mg per day, or 1450 mg to 1550 mg per day, or about 1500 mg per day after the first day.

In some embodiments, the compound of formula (I), or a pharmaceutically acceptable salt thereof, is administered in an amount of 250 mg to 1500 mg, or 500 mg to 1000 mg, or about 750 mg on a first day and in an amount of 250 mg to 1000 mg per day, or about 250 mg to 750 mg per day, or about 500 mg per day after the first day.

In some embodiments, the compound of formula (I), or a pharmaceutically acceptable salt thereof, is administered in an amount of 250 mg to 1500 mg, or 500 mg to 1000 mg, or about 750 mg on the first day.

In some embodiments, the compound of formula (I), or a pharmaceutically acceptable salt thereof, is administered in an amount of 250 mg to 1000 mg per day, or about 250 mg to 750 mg per day, or about 500 mg per day after the first day.

The compound of formula (I), or a pharmaceutically acceptable salt thereof, may be administered in any number of doses per day. In some embodiments, the compound of formula (I), or a pharmaceutically acceptable salt thereof, is administered in one dose per day. In some embodiments, the compound of formula (I), or a pharmaceutically acceptable salt thereof, is administered in one dose of 100 mg to 500 mg, or 150 mg to 400 mg, or 200 mg to 300 mg, or about 250 mg, or 500 mg to 2000 mg, 600 mg to 1800 mg, or 700 mg to 1600 mg, or 800 mg to 1400 mg, or 900 mg to 1200 mg, or about 1000 mg per day, or 500 mg to 2000 mg per day, or 750 mg to 1750 mg per day, or 1000 mg to 1500 mg per day, or 1100 mg to 1400 mg per day, or 1200 mg to 1300 mg per day, or about 1250 mg per day, or 250 mg to 1250 mg per day, or 500 mg to 1000 mg per day, or 600 mg to 900 mg per day, or 700 mg to 800 mg per day, or about 750 mg per day, or 250 mg to 1750 mg per day, or 500 mg to 1500 mg per day, or 750 mg to 1250 mg per day.

In some embodiments, the compound of formula (I), or a pharmaceutically acceptable salt thereof, is administered in two doses per day.

The compound of formula (I), or a pharmaceutically acceptable salt thereof, when administered for multiple days, may be administered in the same or different numbers of doses each day. In some embodiments, the compound of formula (I), or a pharmaceutically acceptable salt thereof, is administered in the same number of doses on the first day and after the first day.

In some embodiments, the compound of formula (I), or a pharmaceutically acceptable salt thereof, is administered in two doses on the first day (i.e., a first dose and a subsequent dose). The quantity of the first dose and the subsequent dose may be the same or different.

In some embodiments, the first dose and the subsequent dose are the same. In some embodiments, the compound of formula (I), or a pharmaceutically acceptable salt thereof, is administered in two doses of 250 mg to 1000 mg, or 300 mg to 900 mg, or 350 mg to 800 mg, or 400 mg to 700 mg, or 450 mg to 600 mg, or about 500 mg per day.

In some embodiments, the first dose is larger than the subsequent dose on the first day. In some embodiments, the first dose is between 1000 mg and 2000 mg, or between 1050 mg and 1950 mg, or between 1100 mg and 1900 mg, or between 1150 mg and 1850 mg, or between 1200 mg and 1800 mg, or between 1250 mg and 1750 mg, or between 1300 mg and 1700 mg, or between 1350 mg and 1650 mg, or between 1400 mg and 1600 mg, or between 1450 mg and 1550 mg, or about 1500 mg, or between 250 mg and 750 mg, or between 400 mg and 600 mg, or about 500 mg. In some embodiments, the subsequent dose is between 500 mg and 1000 mg, or between 550 mg and 950 mg, or between 600 mg and 900 mg, or between 650 mg and 850 mg, or between 700 mg and 800 mg, or between 725 mg and 775 mg, or about 750 mg, or between 100 mg and 500 mg, or about 250 mg.

In some embodiments, the compound of formula (I), or a pharmaceutically acceptable salt thereof, is administered in two doses per day after the first day (i.e., a first dose and a subsequent dose). The quantity of the first dose and the subsequent dose may be the same or different. In some embodiments, the first dose and the subsequent dose are the same after the first day. In some embodiments, the compound of formula (I), or a pharmaceutically acceptable salt thereof, is administered in two doses of 500 to 1000 mg, or in two doses of 550 mg to 950 mg, or in two doses of 600 mg to 900 mg, or in two doses of 625 mg to 875 mg, or in two doses of 650 mg to 850 mg, or in two doses of 675 mg to 825 mg, or in two doses of 700 mg to 800 mg, or in two doses of 725 mg to 775 mg, or in two doses of about 750 mg, or in two doses of 100 mg to 500 mg, or in two doses of about 250 mg per day after the first day. In some embodiments, the compound of formula (I), or a pharmaceutically acceptable salt thereof, is administered in two doses of 500 to 1000 mg, or in two doses of 550 mg to 950 mg, or in two doses of 600 mg to 900 mg, or in two doses of 625 mg to 875 mg, or in two doses of 650 mg to 850 mg, or in two doses of 675 mg to 825 mg, or in two doses of 700 mg to 800 mg, or in two doses of 725 mg to 775 mg, or in two doses of about 750 mg, or in two doses of 100 mg to 500 mg, or in two doses of about 250 mg per day each day after the first day.

In some embodiments, the compound of formula (I), or a pharmaceutically acceptable salt thereof, is administered once per day in a dose of about 250 mg.

In some embodiments, the compound of formula (I), or a pharmaceutically acceptable salt thereof, is administered every 18-30 hours in a dose of about 250 mg.

In some embodiments, the compound of formula (I), or a pharmaceutically acceptable salt thereof, is administered every 21-27 hours in a dose of about 250 mg.

In some embodiments, the compound of formula (I), or a pharmaceutically acceptable salt thereof, is administered every 24 hours in a dose of about 250 mg.

In some embodiments, the compound of formula (I), or a pharmaceutically acceptable salt thereof, is administered once per day in a dose of about 300 mg.

In some embodiments, the compound of formula (I), or a pharmaceutically acceptable salt thereof, is administered every 18-30 hours in a dose of about 300 mg.

In some embodiments, the compound of formula (I), or a pharmaceutically acceptable salt thereof, is administered every 21-27 hours in a dose of about 300 mg.

In some embodiments, the compound of formula (I), or a pharmaceutically acceptable salt thereof, is administered every 24 hours in a dose of about 300 mg.

In some embodiments, the compound of formula (I), or a pharmaceutically acceptable salt thereof, is administered once per day in a dose of about 1000 mg.

In some embodiments, the compound of formula (I), or a pharmaceutically acceptable salt thereof, is administered every 18-30 hours in a dose of about 1000 mg.

In some embodiments, the compound of formula (I), or a pharmaceutically acceptable salt thereof, is administered every 21-27 hours in a dose of about 1000 mg.

In some embodiments, the compound of formula (I), or a pharmaceutically acceptable salt thereof, is administered every 24 hours in a dose of about 1000 mg.

In some embodiments, the compound of formula (I), or a pharmaceutically acceptable salt thereof, is administered once per day in a dose of about 900 mg.

In some embodiments, the compound of formula (I), or a pharmaceutically acceptable salt thereof, is administered every 18-30 hours in a dose of about 900 mg.

In some embodiments, the compound of formula (I), or a pharmaceutically acceptable salt thereof, is administered every 21-27 hours in a dose of about 900 mg.

In some embodiments, the compound of formula (I), or a pharmaceutically acceptable salt thereof, is administered every 24 hours in a dose of about 900 mg.

In some embodiments, the compound of formula (I), or a pharmaceutically acceptable salt thereof, is administered once per day in a dose of about 1200 mg.

In some embodiments, the compound of formula (I), or a pharmaceutically acceptable salt thereof, is administered every 18-30 hours in a dose of about 1200 mg.

In some embodiments, the compound of formula (I), or a pharmaceutically acceptable salt thereof, is administered every 21-27 hours in a dose of about 1200 mg.

In some embodiments, the compound of formula (I), or a pharmaceutically acceptable salt thereof, is administered every 24 hours in a dose of about 1200 mg.

In some embodiments, the compound of formula (I), or a pharmaceutically acceptable salt thereof, is administered twice per day in a dose of about 500 mg (1000 mg per day).

In some embodiments, the compound of formula (I), or a pharmaceutically acceptable salt thereof, is administered every 6-18 hours in a dose of about 500 mg.

In some embodiments, the compound of formula (I), or a pharmaceutically acceptable salt thereof, is administered every 9-15 hours in a dose of about 500 mg.

In some embodiments, the compound of formula (I), or a pharmaceutically acceptable salt thereof, is administered every 12 hours in a dose of about 500 mg.

In some embodiments, the compound of formula (I), or a pharmaceutically acceptable salt thereof, is administered twice per day in a dose of about 600 mg (1200 mg per day).

In some embodiments, the compound of formula (I), or a pharmaceutically acceptable salt thereof, is administered every 6-18 hours in a dose of about 600 mg.

In some embodiments, the compound of formula (I), or a pharmaceutically acceptable salt thereof, is administered every 9-15 hours in a dose of about 600 mg.

In some embodiments, the compound of formula (I), or a pharmaceutically acceptable salt thereof, is administered every 12 hours in a dose of about 600 mg.

In some embodiments, the compound of formula (I), or a pharmaceutically acceptable salt thereof, is administered in a first dose of about 1500 mg and a subsequent dose of about 750 mg on the first day, and in two doses of about 750 mg per day each day after the first day.

In some embodiments, the compound of formula (I), or a pharmaceutically acceptable salt thereof, is administered every 6-18 hours in a first dose of 1500 mg and a subsequent dose of 750 mg.

In some embodiments, the compound of formula (I), or a pharmaceutically acceptable salt thereof, is administered every 9-15 hours in a first dose of 1500 mg and a subsequent dose of 750 mg.

In some embodiments, the compound of formula (I), or a pharmaceutically acceptable salt thereof, is administered every 12 hours in a first dose of 1500 mg and a subsequent dose of 750 mg.

In some embodiments, the compound of formula (I), or a pharmaceutically acceptable salt thereof, is administered in a first dose of about 1500 mg and a subsequent dose of about 900 mg on the first day, and in two doses of about 900 mg per day each day after the first day.

In some embodiments, the compound of formula (I), or a pharmaceutically acceptable salt thereof, is administered every 6-18 hours in a first dose of 1500 mg and a subsequent dose of 900 mg.

In some embodiments, the compound of formula (I), or a pharmaceutically acceptable salt thereof, is administered every 9-15 hours in a first dose of 1500 mg and a subsequent dose of 900 mg.

In some embodiments, the compound of formula (I), or a pharmaceutically acceptable salt thereof, is administered every 12 hours in a first dose of 1500 mg and a subsequent dose of 900 mg.

In some embodiments, the compound of formula (I), or a pharmaceutically acceptable salt thereof, is administered in a first dose of about 1500 mg and a subsequent dose of about 600 mg on the first day, and in two doses of about 600 mg per day each day after the first day.

In some embodiments, the compound of formula (I), or a pharmaceutically acceptable salt thereof, is administered every 6-18 hours in a first dose of 1500 mg and a subsequent dose of 600 mg.

In some embodiments, the compound of formula (I), or a pharmaceutically acceptable salt thereof, is administered every 9-15 hours in a first dose of 1500 mg and a subsequent dose of 600 mg.

In some embodiments, the compound of formula (I), or a pharmaceutically acceptable salt thereof, is administered every 12 hours in a first dose of 1500 mg and a subsequent dose of 600 mg.

In some embodiments, the compound of formula (I), or a pharmaceutically acceptable salt thereof, is administered in a first dose of about 500 mg and a subsequent dose of about 250 mg on the first day, and in two doses of about 250 mg per day each day after the first day.

In some embodiments, the compound of formula (I), or a pharmaceutically acceptable salt thereof, is administered every 6-18 hours in a first dose of about 500 mg and a subsequent dose of about 250 mg.

In some embodiments, the compound of formula (I), or a pharmaceutically acceptable salt thereof, is administered every 9-15 hours in a first dose of about 500 mg and a subsequent dose of about 250 mg.

In some embodiments, the compound of formula (I), or a pharmaceutically acceptable salt thereof, is administered every 12 hours in a first dose of about 500 mg and a subsequent dose of about 250 mg.

In some embodiments, the compound of formula (I), or a pharmaceutically acceptable salt thereof, is administered in a first dose of about 600 mg and a subsequent dose of about 300 mg on the first day, and in two doses of about 300 mg per day each day after the first day.

In some embodiments, the compound of formula (I), or a pharmaceutically acceptable salt thereof, is administered every 6-18 hours in a first dose of about 600 mg and a subsequent dose of about 300 mg.

In some embodiments, the compound of formula (I), or a pharmaceutically acceptable salt thereof, is administered every 9-15 hours in a first dose of about 600 mg and a subsequent dose of about 300 mg.

In some embodiments, the compound of formula (I), or a pharmaceutically acceptable salt thereof, is administered every 12 hours in a first dose of about 600 mg and a subsequent dose of about 300 mg.

In some embodiments, the compound of formula (I), or a pharmaceutically acceptable salt thereof, is administered once per day in a dose of about 600 mg.

In some embodiments, the compound of formula (I), or a pharmaceutically acceptable salt thereof, is administered every 18-30 hours in a dose of about 600 mg.

In some embodiments, the compound of formula (I), or a pharmaceutically acceptable salt thereof, is administered every 21-27 hours in a dose of about 600 mg.

In some embodiments, the compound of formula (I), or a pharmaceutically acceptable salt thereof, is administered every 24 hours in a dose of about 600 mg.

In some embodiments, the compound of formula (I), or a pharmaceutically acceptable salt thereof, is administered once per day in a dose of about 750 mg.

In some embodiments, the compound of formula (I), or a pharmaceutically acceptable salt thereof, is administered every 18-30 hours in a dose of about 750 mg.

In some embodiments, the compound of formula (I), or a pharmaceutically acceptable salt thereof, is administered every 21-27 hours in a dose of about 750 mg.

In some embodiments, the compound of formula (I), or a pharmaceutically acceptable salt thereof, is administered every 24 hours in a dose of about 750 mg.

In some embodiments, the compound of formula (I), or a pharmaceutically acceptable salt thereof, is administered once per day in a dose of about 900 mg.

In some embodiments, the compound of formula (I), or a pharmaceutically acceptable salt thereof, is administered every 18-30 hours in a dose of about 900 mg.

In some embodiments, the compound of formula (I), or a pharmaceutically acceptable salt thereof, is administered every 21-27 hours in a dose of about 900 mg.

In some embodiments, the compound of formula (I), or a pharmaceutically acceptable salt thereof, is administered every 24 hours in a dose of about 900 mg.

In some embodiments, the compound of formula (I), or a pharmaceutically acceptable salt thereof, is administered once per day in a dose of about 1000 mg.

In some embodiments, the compound of formula (I), or a pharmaceutically acceptable salt thereof, is administered every 18-30 hours in a dose of about 1000 mg.

In some embodiments, the compound of formula (I), or a pharmaceutically acceptable salt thereof, is administered every 21-27 hours in a dose of about 1000 mg.

In some embodiments, the compound of formula (I), or a pharmaceutically acceptable salt thereof, is administered every 24 hours in a dose of about 1000 mg.

In some embodiments, the compound of formula (I), or a pharmaceutically acceptable salt thereof, is administered once per day in a dose of about 1200 mg.

In some embodiments, the compound of formula (I), or a pharmaceutically acceptable salt thereof, is administered every 18-30 hours in a dose of about 1200 mg.

In some embodiments, the compound of formula (I), or a pharmaceutically acceptable salt thereof, is administered every 21-27 hours in a dose of about 1200 mg.

In some embodiments, the compound of formula (I), or a pharmaceutically acceptable salt thereof, is administered every 24 hours in a dose of about 1200 mg.

In some embodiments, the compound of formula (I), or a pharmaceutically acceptable salt thereof, is administered once per day in a dose of about 1250 mg.

In some embodiments, the compound of formula (I), or a pharmaceutically acceptable salt thereof, is administered every 18-30 hours in a dose of about 1250 mg.

In some embodiments, the compound of formula (I), or a pharmaceutically acceptable salt thereof, is administered every 21-27 hours in a dose of about 1250 mg.

In some embodiments, the compound of formula (I), or a pharmaceutically acceptable salt thereof, is administered every 24 hours in a dose of about 1250 mg.

In some embodiments, the compound of formula (I), or a pharmaceutically acceptable salt thereof, is administered once per day in a dose of about 1500 mg.

In some embodiments, the compound of formula (I), or a pharmaceutically acceptable salt thereof, is administered every 18-30 hours in a dose of about 1500 mg.

In some embodiments, the compound of formula (I), or a pharmaceutically acceptable salt thereof, is administered every 21-27 hours in a dose of about 1500 mg.

In some embodiments, the compound of formula (I), or a pharmaceutically acceptable salt thereof, is administered every 24 hours in a dose of about 1500 mg.

In some embodiments, the compound of formula (I), or a pharmaceutically acceptable salt thereof, is administered once per day in a dose of 750 mg to 1250 mg.

In some embodiments, the compound of formula (I), or a pharmaceutically acceptable salt thereof, is administered every 18-30 hours in a dose of 750 mg to 1250 mg.

In some embodiments, the compound of formula (I), or a pharmaceutically acceptable salt thereof, is administered every 21-27 hours in a dose of 750 mg to 1250 mg.

In some embodiments, the compound of formula (I), or a pharmaceutically acceptable salt thereof, is administered every 24 hours in a dose of 750 mg to 1250 mg.

In some embodiments, the compound of formula (I), or a pharmaceutically acceptable salt thereof, is administered once per day in a dose of 600 mg to 1500 mg.

In some embodiments, the compound of formula (I), or a pharmaceutically acceptable salt thereof, is administered every 18-30 hours in a dose of 600 mg to 1500 mg.

In some embodiments, the compound of formula (I), or a pharmaceutically acceptable salt thereof, is administered every 21-27 hours in a dose of 600 mg to 1500 mg.

In some embodiments, the compound of formula (I), or a pharmaceutically acceptable salt thereof, is administered every 24 hours in a dose of 600 mg to 1500 mg.

In some embodiments, the compound of formula (I), or a pharmaceutically acceptable salt thereof, is administered once per day in a dose of 900 mg to 1200 mg.

In some embodiments, the compound of formula (I), or a pharmaceutically acceptable salt thereof, is administered every 18-30 hours in a dose of 900 mg to 1200 mg.

In some embodiments, the compound of formula (I), or a pharmaceutically acceptable salt thereof, is administered every 21-27 hours in a dose of 900 mg to 1200 mg.

In some embodiments, the compound of formula (I), or a pharmaceutically acceptable salt thereof, is administered every 24 hours in a dose of 900 mg to 1200 mg.

In some embodiments, the compound of formula (I), or a pharmaceutically acceptable salt thereof, is administered once per day in a dose of about 600 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered every 18-30 hours in a dose of about 600 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered every 21-27 hours in a dose of about 600 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered every 24 hours in a dose of about 600 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered once per day in a dose of about 750 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered every 18-30 hours in a dose of about 750 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered every 21-27 hours in a dose of about 750 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered every 24 hours in a dose of about 750 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered once per day in a dose of about 900 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered every 18-30 hours in a dose of about 900 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered every 21-27 hours in a dose of about 900 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered every 24 hours in a dose of about 900 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered once per day in a dose of about 1000 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered every 18-30 hours in a dose of about 1000 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered every 21-27 hours in a dose of about 1000 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered every 24 hours in a dose of about 1000 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered once per day in a dose of about 1200 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered every 18-30 hours in a dose of about 1200 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered every 21-27 hours in a dose of about 1200 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered every 24 hours in a dose of about 1200 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered once per day in a dose of about 1250 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered every 18-30 hours in a dose of about 1250 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered every 21-27 hours in a dose of about 1250 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered every 24 hours in a dose of about 1250 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered once per day in a dose of about 1500 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered every 18-30 hours in a dose of about 1500 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered every 21-27 hours in a dose of about 1500 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered every 24 hours in a dose of about 1500 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered once per day in a dose of 750 mg to 1250 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered every 18-30 hours in a dose of 750 mg to 1250 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered every 21-27 hours in a dose of 750 mg to 1250 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered every 24 hours in a dose of 750 mg to 1250 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered once per day in a dose of 600 mg to 1500 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered every 18-30 hours in a dose of 600 mg to 1500 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered every 21-27 hours in a dose of 600 mg to 1500 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered every 24 hours in a dose of 600 mg to 1500 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered once per day in a dose of 900 mg to 1200 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered every 18-30 hours in a dose of 900 mg to 1200 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered every 21-27 hours in a dose of 900 mg to 1200 mg, for at least one week, at least two weeks, at least three weeks, at least four weeks, at least five weeks, or at least six weeks, or from one to six weeks.

In some embodiments, the compound of formula (I), or a pharmaceutically acceptable salt thereof, is administered every 24 hours in a dose of 900 mg to 1200 mg, for at least one week, at least two weeks, at least three weeks, at least four weeks, at least five weeks, or at least six weeks, or from one to six weeks.

The compound of formula (I), or a pharmaceutically acceptable salt thereof, may be administered in any form, including any solid form (including any amorphous or crystalline form), any solvate, hydrate, or cocrystal form, or any solution or suspension of the compound of formula (I), or a pharmaceutically acceptable salt thereof. In some embodiments, the compound of formula (I) is administered in Form B. In some embodiments, the compound of formula (I) is administered in a pharmaceutical composition prepared by mixing Form B with a pharmaceutically acceptable carrier, adjuvant, or vehicle. In some embodiments, Form B is characterized by an X-ray powder diffraction pattern (XRPD) comprising at least three approximate peak positions (degrees 2 theta±0.2) when measured using Cu $K_\alpha$ radiation, selected from the group consisting of 4.4, 15.2, 16.4, 18.0, 19.1, 19.3, 19.9, 20.2, 20.5, 21.0, 22.2, 23.5 24.2, 24.8, 26.3, 29.6, 30.1 and 31.3, when the XRPD is collected from about 4 to about 40 degrees 2 theta (2 θ). In some embodiments, Form B is characterized by an X-ray powder diffraction pattern (XRPD) comprising at least three approximate peak positions (degrees 2 theta±0.2) when measured using Cu $K_\alpha$ radiation, selected from the group consisting of 19.3, 22.2, 23.5, 26.3 and 30.1, when the XRPD is collected from about 4 to about 40 degrees 2 theta (2 θ). In some embodiments, Form B is characterized by an X-ray powder diffraction pattern (XRPD), measured using Cu $K_\alpha$ radiation, substantially similar to FIG. 1.

In some embodiments, the method comprises administering to the subject the compound of formula (I) in non-salt form (i.e., as the free acid (4-(2-(4-fluoro-2-methylphenoxy)-4-(trifluoromethyl)benzamido)-2-oxopyridin-1(2H)-yl)methyl dihydrogen phosphate).

The compound of formula (I), or a pharmaceutically acceptable salt thereof, may be administered by any route known in the art. In some embodiments, the compound of formula (I), or a pharmaceutically acceptable salt thereof, is administered orally.

The compound of formula (I), or a pharmaceutically acceptable salt thereof, may be administered for any number of days necessary or desirable to treat or lessen the severity of the subject's pain, which may depend on the type of pain experienced by the subject. In some embodiments, the compound of formula (I), or a pharmaceutically acceptable salt thereof, is administered for at least two days. In some embodiments, the compound of formula (I), or a pharmaceutically acceptable salt thereof, is administered for at least one week, at least two weeks, at least three weeks, at least four weeks, at least five weeks, or at least six weeks, or from one to six weeks.

Indications

The compound of formula (I), or a pharmaceutically acceptable salt thereof, may be administered to a subject for treating or lessening the severity of any type of pain known in the art.

In some embodiments, the pain comprises chronic pain, gut pain, neuropathic pain, musculoskeletal pain, acute pain, inflammatory pain, cancer pain, idiopathic pain, postsurgical pain (e.g., bunionectomy pain or abdominoplasty pain), or visceral pain.

In some embodiments, the pain comprises gut pain. In some embodiments, the gut pain comprises inflammatory bowel disease pain, Crohn's disease pain or interstitial cystitis pain.

In some embodiments, the pain comprises neuropathic pain. In some embodiments, the neuropathic pain comprises post-herpetic neuralgia or idiopathic small-fiber neuropathy. In some embodiments, the neuropathic pain comprises post-herpetic neuralgia, diabetic neuralgia, painful HIV-associated sensory neuropathy, trigeminal neuralgia, burning mouth syndrome, post-amputation pain, phantom pain, painful neuroma; traumatic neuroma; Morton's neuroma; nerve entrapment injury, spinal stenosis, carpal tunnel syndrome, radicular pain, sciatica pain; nerve avulsion injury, brachial plexus avulsion injury; complex regional pain syndrome, drug therapy induced neuralgia, cancer chemotherapy induced neuralgia, anti-retroviral therapy induced neuralgia; post spinal cord injury pain, idiopathic small-fiber neuropathy, idiopathic sensory neuropathy or trigeminal autonomic cephalalgia. As used herein, the phrase "idiopathic small-fiber neuropathy" shall be understood to include any small fiber neuropathy.

In some embodiments, the pain comprises musculoskeletal pain. In some embodiments, the musculoskeletal pain comprises osteoarthritis pain. In some embodiments, the musculoskeletal pain comprises osteoarthritis pain, back pain, cold pain, burn pain or dental pain.

In some embodiments, the pain comprises inflammatory pain. In some embodiments, the inflammatory pain comprises rheumatoid arthritis pain or vulvodynia. In some embodiments, the inflammatory pain comprises rheumatoid arthritis pain.

In some embodiments, the pain comprises idiopathic pain. In some embodiments, the idiopathic pain comprises fibromyalgia pain.

In some embodiments, the pain comprises acute pain. In some aspects, the acute pain comprises acute post-operative pain.

In some embodiments, the pain comprises postsurgical pain (e.g., bunionectomy pain or abdominoplasty pain). In some embodiments, the postsurgical pain comprises bunionectomy pain. In some embodiments, the postsurgical pain comprises abdominoplasty pain.

In some embodiments, the pain comprises visceral pain. In some embodiments, the visceral pain comprises visceral pain from abdominoplasty.

In some embodiments, the pain comprises acute pain, chronic pain, neuropathic pain, inflammatory pain, arthritis, migraine, cluster headaches, trigeminal neuralgia, herpetic neuralgia, general neuralgias, visceral pain, osteoarthritis pain, postherpetic neuralgia, diabetic neuropathy, radicular pain, sciatica pain, back pain, head pain, neck pain, severe pain, intractable pain, nociceptive pain, breakthrough pain, postsurgical pain (e.g., bunionectomy pain or abdominoplasty pain), cancer pain, stress induced angina, or exercise induced angina.

In some embodiments, the pain comprises femur cancer pain; non-malignant chronic bone pain; rheumatoid arthritis; osteoarthritis; spinal stenosis; neuropathic low back pain; myofascial pain syndrome; fibromyalgia; temporomandibular joint pain; chronic visceral pain, abdominal pain; pancreatic pain; IBS pain; chronic and acute headache pain; migraine; tension headache; cluster headaches; chronic and acute neuropathic pain, post-herpetic neuralgia; diabetic neuropathy; HIV-associated neuropathy; trigeminal neuralgia; Charcot-Marie-Tooth neuropathy; hereditary sensory neuropathy; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury pain; exercise pain; acute visceral pain; pyelonephritis; appendicitis; cholecystitis; intestinal obstruction; hernias; chest pain, cardiac pain; pelvic pain, renal colic pain, acute obstetric pain, labor pain; cesarean section pain; acute inflammatory pain, burn pain, trauma pain; acute intermittent pain, endometriosis; acute herpes zoster pain; sickle cell anemia; acute pancreatitis; breakthrough pain; orofacial pain; sinusitis pain; dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; painful bladder syndrome; interstitial cystitis (IC) pain; prostatitis; complex regional pain syndrome (CRPS), type I, complex regional pain syndrome (CRPS) type II; widespread pain, paroxysmal extreme pain, pruritus, tinnitus, or angina-induced pain.

Patient Populations

The compound of formula (I), or a pharmaceutically acceptable salt thereof, may be administered to a subject having pain of any severity for treating or lessening the severity of the pain.

In some embodiments, the subject has a baseline pain score of at least 4 on an 11-point Numeric Pain Rating Scale prior to administration of the compound of formula (I), or a pharmaceutically acceptable salt thereof.

In some embodiments, the subject has a baseline pain level of moderate or severe on a Verbal Categorical Rating Scale prior to administration of the compound of formula (I), or a pharmaceutically acceptable salt thereof.

Compounds, Pharmaceutically Acceptable Salts, and Compositions for Use

In another aspect, the disclosure relates to a compound of formula (I), or a pharmaceutically acceptable salt or pharmaceutical composition thereof, for use in a method of treating or lessening the severity of pain in a subject in accordance with the method described herein (including any embodiment thereof).

In another aspect, the disclosure relates to a compound of formula (I), or a pharmaceutically acceptable salt thereof, for use in a method of treating or lessening the severity of pain in a subject, comprising administering to the subject the compound of formula (I), or the pharmaceutically acceptable salt thereof, once per day in a dose of about 250 mg.

In another aspect, the disclosure relates to a compound of formula (I), or a pharmaceutically acceptable salt thereof, for use in a method of treating or lessening the severity of pain in a subject, comprising administering to the subject the compound of formula (I), or the pharmaceutically acceptable salt thereof, once per day in a dose of about 1000 mg.

In another aspect, the disclosure relates to a compound of formula (I), or a pharmaceutically acceptable salt thereof, for use in a method of treating or lessening the severity of pain in a subject, comprising administering to the subject the compound of formula (I), or the pharmaceutically acceptable salt thereof, once per day in a dose of about 1000 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of pain in a subject, comprising administering to the subject the compound of formula (I), or the pharmaceutically acceptable salt thereof, twice per day in a dose of about 500 mg (1000 mg per day).

In another aspect, the disclosure relates to a compound of formula (I), or a pharmaceutically acceptable salt thereof, for use in a method of treating or lessening the severity of pain in a subject, comprising administering to the subject the compound of formula (I), or the pharmaceutically acceptable salt thereof, in a first dose of about 1500 mg and a subsequent dose of about 750 mg on the first day, and in two doses of about 750 mg per day each day after the first day.

In another aspect, the disclosure relates to a compound of formula (I), or a pharmaceutically acceptable salt thereof, for use in a method of treating or lessening the severity of pain in a subject, comprising administering to the subject the compound of formula (I), or the pharmaceutically acceptable salt thereof, in a first dose of about 500 mg and a subsequent dose of about 250 mg on the first day, and in two doses of about 250 mg per day each day after the first day.

In another aspect, the disclosure relates to a compound of formula (I), or a pharmaceutically acceptable salt thereof, for use in a method of treating or lessening the severity of pain in a subject, comprising administering to the subject the compound of formula (I), or the pharmaceutically acceptable salt thereof, once per day in a dose of about 750 mg.

In another aspect, the disclosure relates to a compound of formula (I), or a pharmaceutically acceptable salt thereof, for use in a method of treating or lessening the severity of pain in a subject, comprising administering to the subject the compound of formula (I), or the pharmaceutically acceptable salt thereof, once per day in a dose of about 750 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of pain in a subject, comprising administering to the subject the compound of formula (I), or the pharmaceutically acceptable salt thereof, once per day in a dose of about 1250 mg.

In another aspect, the disclosure relates to a compound of formula (I), or a pharmaceutically acceptable salt thereof, for use in a method of treating or lessening the severity of pain in a subject, comprising administering to the subject the compound of formula (I), or the pharmaceutically acceptable salt thereof, once per day in a dose of about 1250 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of pain in a subject, comprising administering to the subject the compound of formula (I), or the pharmaceutically acceptable salt thereof, once per day in a dose of 750 mg to 1250 mg.

In another aspect, the disclosure relates to a compound of formula (I), or a pharmaceutically acceptable salt thereof, for use in a method of treating or lessening the severity of pain in a subject, comprising administering to the subject the compound of formula (I), or the pharmaceutically acceptable salt thereof, once per day in a dose of 750 mg to 1250 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of chronic pain in a subject, comprising administering to the subject the compound of formula (I), or the pharmaceutically acceptable salt thereof.

In another aspect, the disclosure relates to a compound of formula (I), or a pharmaceutically acceptable salt thereof, for use in a method of treating or lessening the severity of chronic pain in a subject, comprising administering to the subject the compound of formula (I), or the pharmaceutically acceptable salt thereof, once per day in a dose of about 250 mg.

In another aspect, the disclosure relates to a compound of formula (I), or a pharmaceutically acceptable salt thereof, for use in a method of treating or lessening the severity of chronic pain in a subject, comprising administering to the subject the compound of formula (I), or the pharmaceutically acceptable salt thereof, once per day in a dose of about 1000 mg.

In another aspect, the disclosure relates to a compound of formula (I), or a pharmaceutically acceptable salt thereof, for use in a method of treating or lessening the severity of chronic pain in a subject, comprising administering to the subject the compound of formula (I), or the pharmaceutically acceptable salt thereof, once per day in a dose of about 1000 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of chronic pain in a subject, comprising administering to the subject the compound of formula (I), or the pharmaceutically acceptable salt thereof, twice per day in a dose of about 500 mg (1000 mg per day).

In another aspect, the disclosure relates to a compound of formula (I), or a pharmaceutically acceptable salt thereof, for use in a method of treating or lessening the severity of chronic pain in a subject, comprising administering to the subject the compound of formula (I), or the pharmaceutically acceptable salt thereof, in a first dose of about 1500 mg and a subsequent dose of about 750 mg on the first day, and in two doses of about 750 mg per day each day after the first day.

In another aspect, the disclosure relates to a compound of formula (I), or a pharmaceutically acceptable salt thereof, for use in a method of treating or lessening the severity of chronic pain in a subject, comprising administering to the subject the compound of formula (I), or the pharmaceutically acceptable salt thereof, in a first dose of about 500 mg and a subsequent dose of about 250 mg on the first day, and in two doses of about 250 mg per day each day after the first day.

In another aspect, the disclosure relates to a compound of formula (I), or a pharmaceutically acceptable salt thereof, for use in a method of treating or lessening the severity of chronic pain in a subject, comprising administering to the subject the compound of formula (I), or the pharmaceutically acceptable salt thereof, once per day in a dose of about 750 mg.

In another aspect, the disclosure relates to a compound of formula (I), or a pharmaceutically acceptable salt thereof, for use in a method of treating or lessening the severity of chronic pain in a subject, comprising administering to the subject the compound of formula (I), or the pharmaceutically acceptable salt thereof, once per day in a dose of about 750 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of chronic pain in a subject, comprising administering to the subject the compound of formula (I), or the pharmaceutically acceptable salt thereof, once per day in a dose of about 1250 mg.

In another aspect, the disclosure relates to a compound of formula (I), or a pharmaceutically acceptable salt thereof, for use in a method of treating or lessening the severity of chronic pain in a subject, comprising administering to the subject the compound of formula (I), or the pharmaceutically acceptable salt thereof, once per day in a dose of about 1250 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of chronic pain in a subject, comprising administering to the subject the compound of formula (I), or the pharmaceutically acceptable salt thereof, once per day in a dose of 750 mg to 1250 mg.

In another aspect, the disclosure relates to a compound of formula (I), or a pharmaceutically acceptable salt thereof, for use in a method of treating or lessening the severity of chronic pain in a subject, comprising administering to the subject the compound of formula (I), or the pharmaceutically acceptable salt thereof, once per day in a dose of 750 mg to 1250 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of gut pain in a subject, comprising administering to the subject the compound of formula (I), or the pharmaceutically acceptable salt thereof.

In another aspect, the disclosure relates to a compound of formula (I), or a pharmaceutically acceptable salt thereof, for use in a method of treating or lessening the severity of gut pain in a subject, comprising administering to the subject the compound of formula (I), or the pharmaceutically acceptable salt thereof, once per day in a dose of about 250 mg.

In another aspect, the disclosure relates to a compound of formula (I), or a pharmaceutically acceptable salt thereof, for use in a method of treating or lessening the severity of gut pain in a subject, comprising administering to the subject the compound of formula (I), or the pharmaceutically acceptable salt thereof, once per day in a dose of about 1000 mg.

In another aspect, the disclosure relates to a compound of formula (I), or a pharmaceutically acceptable salt thereof, for use in a method of treating or lessening the severity of gut pain in a subject, comprising administering to the subject the compound of formula (I), or the pharmaceutically acceptable salt thereof, once per day in a dose of about 1000 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of gut pain in a subject, comprising administering to the subject the compound of formula (I), or the pharmaceutically acceptable salt thereof, twice per day in a dose of about 500 mg (1000 mg per day).

In another aspect, the disclosure relates to a compound of formula (I), or a pharmaceutically acceptable salt thereof, for use in a method of treating or lessening the severity of gut pain in a subject, comprising administering to the subject the compound of formula (I), or the pharmaceutically acceptable salt thereof, in a first dose of about 1500 mg and a subsequent dose of about 750 mg on the first day, and in two doses of about 750 mg per day each day after the first day.

In another aspect, the disclosure relates to a compound of formula (I), or a pharmaceutically acceptable salt thereof, for use in a method of treating or lessening the severity of gut pain in a subject, comprising administering to the subject the compound of formula (I), or the pharmaceutically acceptable salt thereof, in a first dose of about 500 mg and a subsequent dose of about 250 mg on the first day, and in two doses of about 250 mg per day each day after the first day.

In another aspect, the disclosure relates to a compound of formula (I), or a pharmaceutically acceptable salt thereof, for use in a method of treating or lessening the severity of gut pain in a subject, comprising administering to the subject the compound of formula (I), or the pharmaceutically acceptable salt thereof, once per day in a dose of about 750 mg.

In another aspect, the disclosure relates to a compound of formula (I), or a pharmaceutically acceptable salt thereof, for use in a method of treating or lessening the severity of gut pain in a subject, comprising administering to the subject the compound of formula (I), or the pharmaceutically acceptable salt thereof, once per day in a dose of about 750 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of gut pain in a subject, comprising administering to the subject the compound of formula (I), or the pharmaceutically acceptable salt thereof, once per day in a dose of about 1250 mg.

In another aspect, the disclosure relates to a compound of formula (I), or a pharmaceutically acceptable salt thereof, for use in a method of treating or lessening the severity of gut pain in a subject, comprising administering to the subject the compound of formula (I), or the pharmaceutically acceptable salt thereof, once per day in a dose of about 1250 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of gut pain in a subject, comprising administering to the subject the compound of formula (I), or the pharmaceutically acceptable salt thereof, once per day in a dose of 750 mg to 1250 mg.

In another aspect, the disclosure relates to a compound of formula (I), or a pharmaceutically acceptable salt thereof, for use in a method of treating or lessening the severity of gut pain in a subject, comprising administering to the subject the compound of formula (I), or the pharmaceutically acceptable salt thereof, once per day in a dose of 750 mg to 1250 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of neuropathic pain in a subject, comprising administering to the subject the compound of formula (I), or the pharmaceutically acceptable salt thereof.

In another aspect, the disclosure relates to a compound of formula (I), or a pharmaceutically acceptable salt thereof, for use in a method of treating or lessening the severity of neuropathic pain in a subject, comprising administering to the subject the compound of formula (I), or the pharmaceutically acceptable salt thereof, once per day in a dose of about 250 mg.

In another aspect, the disclosure relates to a compound of formula (I), or a pharmaceutically acceptable salt thereof, for use in a method of treating or lessening the severity of neuropathic pain in a subject, comprising administering to the subject the compound of formula (I), or the pharmaceutically acceptable salt thereof, once per day in a dose of about 1000 mg.

In another aspect, the disclosure relates to a compound of formula (I), or a pharmaceutically acceptable salt thereof, for use in a method of treating or lessening the severity of neuropathic pain in a subject, comprising administering to the subject the compound of formula (I), or the pharmaceutically acceptable salt thereof, once per day in a dose of about 1000 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of neuropathic pain in a subject, comprising administering to the subject the compound of formula (I), or the pharmaceutically acceptable salt thereof, twice per day in a dose of about 500 mg (1000 mg per day).

In another aspect, the disclosure relates to a compound of formula (I), or a pharmaceutically acceptable salt thereof, for use in a method of treating or lessening the severity of neuropathic pain in a subject, comprising administering to the subject the compound of formula (I), or the pharmaceutically acceptable salt thereof, in a first dose of about 1500 mg and a subsequent dose of about 750 mg on the first day, and in two doses of about 750 mg per day each day after the first day.

In another aspect, the disclosure relates to a compound of formula (I), or a pharmaceutically acceptable salt thereof, for use in a method of treating or lessening the severity of neuropathic pain in a subject, comprising administering to the subject the compound of formula (I), or the pharmaceutically acceptable salt thereof, in a first dose of about 500 mg and a subsequent dose of about 250 mg on the first day, and in two doses of about 250 mg per day each day after the first day.

In another aspect, the disclosure relates to a compound of formula (I), or a pharmaceutically acceptable salt thereof, for use in a method of treating or lessening the severity of neuropathic pain in a subject, comprising administering to the subject the compound of formula (I), or the pharmaceutically acceptable salt thereof, once per day in a dose of about 750 mg.

In another aspect, the disclosure relates to a compound of formula (I), or a pharmaceutically acceptable salt thereof, for use in a method of treating or lessening the severity of neuropathic pain in a subject, comprising administering to the subject the compound of formula (I), or the pharmaceutically acceptable salt thereof, once per day in a dose of about 750 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of neuropathic pain in a subject, comprising administering to the subject the compound of formula (I), or the pharmaceutically acceptable salt thereof, once per day in a dose of about 1250 mg.

In another aspect, the disclosure relates to a compound of formula (I), or a pharmaceutically acceptable salt thereof, for use in a method of treating or lessening the severity of neuropathic pain in a subject, comprising administering to the subject the compound of formula (I), or the pharmaceutically acceptable salt thereof, once per day in a dose of about 1250 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of neuropathic pain in a subject, comprising administering to the subject the compound of formula (I), or the pharmaceutically acceptable salt thereof, once per day in a dose of 750 mg to 1250 mg.

In another aspect, the disclosure relates to a compound of formula (I), or a pharmaceutically acceptable salt thereof, for use in a method of treating or lessening the severity of neuropathic pain in a subject, comprising administering to the subject the compound of formula (I), or the pharmaceutically acceptable salt thereof, once per day in a dose of 750 mg to 1250 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of idiopathic small fiber neuropathy in a subject, comprising administering to the subject the compound of formula (I), or the pharmaceutically acceptable salt thereof.

In another aspect, the disclosure relates to a compound of formula (I), or a pharmaceutically acceptable salt thereof, for use in a method of treating or lessening the severity of idiopathic small fiber neuropathy in a subject, comprising administering to the subject the compound of formula (I), or the pharmaceutically acceptable salt thereof, once per day in a dose of about 250 mg.

In another aspect, the disclosure relates to a compound of formula (I), or a pharmaceutically acceptable salt thereof, for use in a method of treating or lessening the severity of idiopathic small fiber neuropathy in a subject, comprising administering to the subject the compound of formula (I), or the pharmaceutically acceptable salt thereof, once per day in a dose of about 1000 mg.

In another aspect, the disclosure relates to a compound of formula (I), or a pharmaceutically acceptable salt thereof, for use in a method of treating or lessening the severity of idiopathic small fiber neuropathy in a subject, comprising administering to the subject the compound of formula (I), or the pharmaceutically acceptable salt thereof, once per day in a dose of about 1000 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of idiopathic small fiber neuropathy in a subject, comprising administering to the subject the compound of formula (I), or the pharmaceutically acceptable salt thereof, twice per day in a dose of about 500 mg (1000 mg per day).

In another aspect, the disclosure relates to a compound of formula (I), or a pharmaceutically acceptable salt thereof, for use in a method of treating or lessening the severity of idiopathic small fiber neuropathy in a subject, comprising administering to the subject the compound of formula (I), or the pharmaceutically acceptable salt thereof, in a first dose of about 1500 mg and a subsequent dose of about 750 mg on the first day, and in two doses of about 750 mg per day each day after the first day.

In another aspect, the disclosure relates to a compound of formula (I), or a pharmaceutically acceptable salt thereof, for use in a method of treating or lessening the severity of idiopathic small fiber neuropathy in a subject, comprising administering to the subject the compound of formula (I), or the pharmaceutically acceptable salt thereof, in a first dose of about 500 mg and a subsequent dose of about 250 mg on the first day, and in two doses of about 250 mg per day each day after the first day.

In another aspect, the disclosure relates to a compound of formula (I), or a pharmaceutically acceptable salt thereof, for use in a method of treating or lessening the severity of idiopathic small fiber neuropathy in a subject, comprising administering to the subject the compound of formula (I), or the pharmaceutically acceptable salt thereof, once per day in a dose of about 750 mg.

In another aspect, the disclosure relates to a compound of formula (I), or a pharmaceutically acceptable salt thereof, for use in a method of treating or lessening the severity of idiopathic small fiber neuropathy in a subject, comprising administering to the subject the compound of formula (I), or the pharmaceutically acceptable salt thereof, once per day in a dose of about 750 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of idiopathic small fiber neuropathy in a subject, comprising administering to the subject the compound of formula (I), or the pharmaceutically acceptable salt thereof, once per day in a dose of about 1250 mg.

In another aspect, the disclosure relates to a compound of formula (I), or a pharmaceutically acceptable salt thereof, for use in a method of treating or lessening the severity of idiopathic small fiber neuropathy in a subject, comprising administering to the subject the compound of formula (I), or the pharmaceutically acceptable salt thereof, once per day in a dose of about 1250 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of idiopathic small fiber neuropathy in a subject, comprising administering to the subject the compound of formula (I), or the pharmaceutically acceptable salt thereof, once per day in a dose of 750 mg to 1250 mg.

In another aspect, the disclosure relates to a compound of formula (I), or a pharmaceutically acceptable salt thereof, for use in a method of treating or lessening the severity of idiopathic small fiber neuropathy in a subject, comprising administering to the subject the compound of formula (I), or the pharmaceutically acceptable salt thereof, once per day in a dose of 750 mg to 1250 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of musculoskeletal pain in a subject, comprising administering to the subject the compound of formula (I), or the pharmaceutically acceptable salt thereof.

In another aspect, the disclosure relates to a compound of formula (I), or a pharmaceutically acceptable salt thereof, for use in a method of treating or lessening the severity of musculoskeletal pain in a subject, comprising administering to the subject the compound of formula (I), or the pharmaceutically acceptable salt thereof, once per day in a dose of about 250 mg.

In another aspect, the disclosure relates to a compound of formula (I), or a pharmaceutically acceptable salt thereof, for use in a method of treating or lessening the severity of musculoskeletal pain in a subject, comprising administering to the subject the compound of formula (I), or the pharmaceutically acceptable salt thereof, once per day in a dose of about 1000 mg.

In another aspect, the disclosure relates to a compound of formula (I), or a pharmaceutically acceptable salt thereof, for use in a method of treating or lessening the severity of musculoskeletal pain in a subject, comprising administering to the subject the compound of formula (I), or the pharmaceutically acceptable salt thereof, once per day in a dose of about 1000 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of musculoskeletal pain in a subject, comprising administering to the subject the compound of formula (I), or the pharmaceutically acceptable salt thereof, twice per day in a dose of about 500 mg (1000 mg per day).

In another aspect, the disclosure relates to a compound of formula (I), or a pharmaceutically acceptable salt thereof, for use in a method of treating or lessening the severity of musculoskeletal pain in a subject, comprising administering to the subject the compound of formula (I), or the pharmaceutically acceptable salt thereof, in a first dose of about 1500 mg and a subsequent dose of about 750 mg on the first day, and in two doses of about 750 mg per day each day after the first day.

In another aspect, the disclosure relates to a compound of formula (I), or a pharmaceutically acceptable salt thereof, for use in a method of treating or lessening the severity of musculoskeletal pain in a subject, comprising administering to the subject the compound of formula (I), or the pharmaceutically acceptable salt thereof, in a first dose of about 500 mg and a subsequent dose of about 250 mg on the first day, and in two doses of about 250 mg per day each day after the first day.

In another aspect, the disclosure relates to a compound of formula (I), or a pharmaceutically acceptable salt thereof, for use in a method of treating or lessening the severity of musculoskeletal pain in a subject, comprising administering to the subject the compound of formula (I), or the pharmaceutically acceptable salt thereof, once per day in a dose of about 750 mg.

In another aspect, the disclosure relates to a compound of formula (I), or a pharmaceutically acceptable salt thereof, for use in a method of treating or lessening the severity of musculoskeletal pain in a subject, comprising administering to the subject the compound of formula (I), or the pharmaceutically acceptable salt thereof, once per day in a dose of about 750 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of musculoskeletal pain in a subject, comprising administering to the subject the compound of formula (I), or the pharmaceutically acceptable salt thereof, once per day in a dose of about 1250 mg.

In another aspect, the disclosure relates to a compound of formula (I), or a pharmaceutically acceptable salt thereof, for use in a method of treating or lessening the severity of musculoskeletal pain in a subject, comprising administering to the subject the compound of formula (I), or the pharmaceutically acceptable salt thereof, once per day in a dose of about 1250 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of musculoskeletal pain in a subject, comprising administering to the subject the compound of formula (I), or the pharmaceutically acceptable salt thereof, once per day in a dose of 750 mg to 1250 mg.

In another aspect, the disclosure relates to a compound of formula (I), or a pharmaceutically acceptable salt thereof, for use in a method of treating or lessening the severity of musculoskeletal pain in a subject, comprising administering to the subject the compound of formula (I), or the pharmaceutically acceptable salt thereof, once per day in a dose of 750 mg to 1250 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of osteoarthritis pain in a subject, comprising administering to the subject the compound of formula (I), or the pharmaceutically acceptable salt thereof.

In another aspect, the disclosure relates to a compound of formula (I), or a pharmaceutically acceptable salt thereof, for use in a method of treating or lessening the severity of osteoarthritis pain in a subject, comprising administering to the subject the compound of formula (I), or the pharmaceutically acceptable salt thereof, once per day in a dose of about 250 mg.

In another aspect, the disclosure relates to a compound of formula (I), or a pharmaceutically acceptable salt thereof, for use in a method of treating or lessening the severity of osteoarthritis pain in a subject, comprising administering to the subject the compound of formula (I), or the pharmaceutically acceptable salt thereof, once per day in a dose of about 1000 mg.

In another aspect, the disclosure relates to a compound of formula (I), or a pharmaceutically acceptable salt thereof, for use in a method of treating or lessening the severity of osteoarthritis pain in a subject, comprising administering to the subject the compound of formula (I), or the pharmaceutically acceptable salt thereof, once per day in a dose of about 1000 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of osteoarthritis pain in a subject, comprising administering to the subject the compound of formula (I), or the pharmaceutically acceptable salt thereof, twice per day in a dose of about 500 mg (1000 mg per day).

In another aspect, the disclosure relates to a compound of formula (I), or a pharmaceutically acceptable salt thereof, for use in a method of treating or lessening the severity of osteoarthritis pain in a subject, comprising administering to the subject the compound of formula (I), or the pharmaceutically acceptable salt thereof, in a first dose of about 1500 mg and a subsequent dose of about 750 mg on the first day, and in two doses of about 750 mg per day each day after the first day.

In another aspect, the disclosure relates to a compound of formula (I), or a pharmaceutically acceptable salt thereof, for use in a method of treating or lessening the severity of osteoarthritis pain in a subject, comprising administering to the subject the compound of formula (I), or the pharmaceutically acceptable salt thereof, in a first dose of about 500 mg and a subsequent dose of about 250 mg on the first day, and in two doses of about 250 mg per day each day after the first day.

In another aspect, the disclosure relates to a compound of formula (I), or a pharmaceutically acceptable salt thereof, for use in a method of treating or lessening the severity of osteoarthritis pain in a subject, comprising administering to the subject the compound of formula (I), or the pharmaceutically acceptable salt thereof, once per day in a dose of about 750 mg.

In another aspect, the disclosure relates to a compound of formula (I), or a pharmaceutically acceptable salt thereof, for use in a method of treating or lessening the severity of osteoarthritis pain in a subject, comprising administering to the subject the compound of formula (I), or the pharmaceutically acceptable salt thereof, once per day in a dose of about 750 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of osteoarthritis pain in a subject, comprising administering to the subject the compound of formula (I), or the pharmaceutically acceptable salt thereof, once per day in a dose of about 1250 mg.

In another aspect, the disclosure relates to a compound of formula (I), or a pharmaceutically acceptable salt thereof, for use in a method of treating or lessening the severity of osteoarthritis pain in a subject, comprising administering to the subject the compound of formula (I), or the pharmaceutically acceptable salt thereof, once per day in a dose of about 1250 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of osteoarthritis pain in a subject, comprising administering to the subject the compound of formula (I), or the pharmaceutically acceptable salt thereof, once per day in a dose of 750 mg to 1250 mg.

In another aspect, the disclosure relates to a compound of formula (I), or a pharmaceutically acceptable salt thereof, for use in a method of treating or lessening the severity of osteoarthritis pain in a subject, comprising administering to the subject the compound of formula (I), or the pharmaceutically acceptable salt thereof, once per day in a dose of 750 mg to 1250 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of acute pain in a subject, comprising administering to the subject the compound of formula (I), or the pharmaceutically acceptable salt thereof.

In another aspect, the disclosure relates to a compound of formula (I), or a pharmaceutically acceptable salt thereof, for use in a method of treating or lessening the severity of acute pain in a subject, comprising administering to the subject the compound of formula (I), or the pharmaceutically acceptable salt thereof, once per day in a dose of about 250 mg.

In another aspect, the disclosure relates to a compound of formula (I), or a pharmaceutically acceptable salt thereof, for use in a method of treating or lessening the severity of acute pain in a subject, comprising administering to the subject the compound of formula (I), or the pharmaceutically acceptable salt thereof, once per day in a dose of about 1000 mg.

In another aspect, the disclosure relates to a compound of formula (I), or a pharmaceutically acceptable salt thereof, for use in a method of treating or lessening the severity of acute pain in a subject, comprising administering to the subject the compound of formula (I), or the pharmaceutically acceptable salt thereof, once per day in a dose of about 1000 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of acute pain in a subject, comprising administering to the subject the compound of formula (I), or the pharmaceutically acceptable salt thereof, twice per day in a dose of about 500 mg (1000 mg per day).

In another aspect, the disclosure relates to a compound of formula (I), or a pharmaceutically acceptable salt thereof, for use in a method of treating or lessening the severity of acute pain in a subject, comprising administering to the subject the compound of formula (I), or the pharmaceutically acceptable salt thereof, in a first dose of about 1500 mg and a subsequent dose of about 750 mg on the first day, and in two doses of about 750 mg per day each day after the first day.

In another aspect, the disclosure relates to a compound of formula (I), or a pharmaceutically acceptable salt thereof, for use in a method of treating or lessening the severity of acute pain in a subject, comprising administering to the subject the compound of formula (I), or the pharmaceutically acceptable salt thereof, in a first dose of about 500 mg and a subsequent dose of about 250 mg on the first day, and in two doses of about 250 mg per day each day after the first day.

In another aspect, the disclosure relates to a compound of formula (I), or a pharmaceutically acceptable salt thereof, for use in a method of treating or lessening the severity of acute pain in a subject, comprising administering to the subject the compound of formula (I), or the pharmaceutically acceptable salt thereof, once per day in a dose of about 750 mg.

In another aspect, the disclosure relates to a compound of formula (I), or a pharmaceutically acceptable salt thereof, for use in a method of treating or lessening the severity of acute pain in a subject, comprising administering to the subject the compound of formula (I), or the pharmaceutically acceptable salt thereof, once per day in a dose of about 750 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of acute pain in a subject, comprising administering to the subject the compound of formula (I), or the pharmaceutically acceptable salt thereof, once per day in a dose of about 1250 mg.

In another aspect, the disclosure relates to a compound of formula (I), or a pharmaceutically acceptable salt thereof, for use in a method of treating or lessening the severity of acute pain in a subject, comprising administering to the subject the compound of formula (I), or the pharmaceutically acceptable salt thereof, once per day in a dose of about 1250 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of acute pain in a subject, comprising administering to the subject the compound of formula (I), or the pharmaceutically acceptable salt thereof, once per day in a dose of 750 mg to 1250 mg.

In another aspect, the disclosure relates to a compound of formula (I), or a pharmaceutically acceptable salt thereof, for use in a method of treating or lessening the severity of acute pain in a subject, comprising administering to the subject the compound of formula (I), or the pharmaceutically acceptable salt thereof, once per day in a dose of 750 mg to 1250 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of inflammatory pain in a subject, comprising administering to the subject the compound of formula (I), or the pharmaceutically acceptable salt thereof.

In another aspect, the disclosure relates to a compound of formula (I), or a pharmaceutically acceptable salt thereof, for use in a method of treating or lessening the severity of inflammatory pain in a subject, comprising administering to the subject the compound of formula (I), or the pharmaceutically acceptable salt thereof, once per day in a dose of about 250 mg.

In another aspect, the disclosure relates to a compound of formula (I), or a pharmaceutically acceptable salt thereof, for use in a method of treating or lessening the severity of inflammatory pain in a subject, comprising administering to the subject the compound of formula (I), or the pharmaceutically acceptable salt thereof, once per day in a dose of about 1000 mg.

In another aspect, the disclosure relates to a compound of formula (I), or a pharmaceutically acceptable salt thereof, for use in a method of treating or lessening the severity of inflammatory pain in a subject, comprising administering to the subject the compound of formula (I), or the pharmaceutically acceptable salt thereof, once per day in a dose of about 1000 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of inflammatory pain in a subject, comprising administering to the subject the compound of formula (I), or the pharmaceutically acceptable salt thereof, twice per day in a dose of about 500 mg (1000 mg per day).

In another aspect, the disclosure relates to a compound of formula (I), or a pharmaceutically acceptable salt thereof, for use in a method of treating or lessening the severity of inflammatory pain in a subject, comprising administering to the subject the compound of formula (I), or the pharmaceutically acceptable salt thereof, in a first dose of about 1500 mg and a subsequent dose of about 750 mg on the first day, and in two doses of about 750 mg per day each day after the first day.

In another aspect, the disclosure relates to a compound of formula (I), or a pharmaceutically acceptable salt thereof, for use in a method of treating or lessening the severity of inflammatory pain in a subject, comprising administering to the subject the compound of formula (I), or the pharmaceutically acceptable salt thereof, in a first dose of about 500 mg and a subsequent dose of about 250 mg on the first day, and in two doses of about 250 mg per day each day after the first day.

In another aspect, the disclosure relates to a compound of formula (I), or a pharmaceutically acceptable salt thereof, for use in a method of treating or lessening the severity of inflammatory pain in a subject, comprising administering to the subject the compound of formula (I), or the pharmaceutically acceptable salt thereof, once per day in a dose of about 750 mg.

In another aspect, the disclosure relates to a compound of formula (I), or a pharmaceutically acceptable salt thereof, for use in a method of treating or lessening the severity of inflammatory pain in a subject, comprising administering to the subject the compound of formula (I), or the pharmaceutically acceptable salt thereof, once per day in a dose of about 750 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of inflammatory pain in a subject, comprising administering to the subject the compound of formula (I), or the pharmaceutically acceptable salt thereof, once per day in a dose of about 1250 mg.

In another aspect, the disclosure relates to a compound of formula (I), or a pharmaceutically acceptable salt thereof, for use in a method of treating or lessening the severity of inflammatory pain in a subject, comprising administering to the subject the compound of formula (I), or the pharmaceutically acceptable salt thereof, once per day in a dose of about 1250 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of inflammatory pain in a subject, comprising administering to the subject the compound of formula (I), or the pharmaceutically acceptable salt thereof, once per day in a dose of 750 mg to 1250 mg.

In another aspect, the disclosure relates to a compound of formula (I), or a pharmaceutically acceptable salt thereof, for use in a method of treating or lessening the severity of inflammatory pain in a subject, comprising administering to the subject the compound of formula (I), or the pharmaceutically acceptable salt thereof, once per day in a dose of 750 mg to 1250 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of cancer pain in a subject, comprising administering to the subject the compound of formula (I), or the pharmaceutically acceptable salt thereof.

In another aspect, the disclosure relates to a compound of formula (I), or a pharmaceutically acceptable salt thereof, for use in a method of treating or lessening the severity of cancer pain in a subject, comprising administering to the subject the compound of formula (I), or the pharmaceutically acceptable salt thereof, once per day in a dose of about 250 mg.

In another aspect, the disclosure relates to a compound of formula (I), or a pharmaceutically acceptable salt thereof, for use in a method of treating or lessening the severity of cancer pain in a subject, comprising administering to the subject the compound of formula (I), or the pharmaceutically acceptable salt thereof, once per day in a dose of about 1000 mg.

In another aspect, the disclosure relates to a compound of formula (I), or a pharmaceutically acceptable salt thereof, for use in a method of treating or lessening the severity of cancer pain in a subject, comprising administering to the subject the compound of formula (I), or the pharmaceutically acceptable salt thereof, once per day in a dose of about 1000 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of cancer pain in a subject, comprising administering to the subject the compound of formula (I), or the pharmaceutically acceptable salt thereof, twice per day in a dose of about 500 mg (1000 mg per day).

In another aspect, the disclosure relates to a compound of formula (I), or a pharmaceutically acceptable salt thereof, for use in a method of treating or lessening the severity of cancer pain in a subject, comprising administering to the subject the compound of formula (I), or the pharmaceutically acceptable salt thereof, in a first dose of about 1500 mg and a subsequent dose of about 750 mg on the first day, and in two doses of about 750 mg per day each day after the first day.

In another aspect, the disclosure relates to a compound of formula (I), or a pharmaceutically acceptable salt thereof, for use in a method of treating or lessening the severity of cancer pain in a subject, comprising administering to the subject the compound of formula (I), or the pharmaceutically acceptable salt thereof, in a first dose of about 500 mg and a subsequent dose of about 250 mg on the first day, and in two doses of about 250 mg per day each day after the first day.

In another aspect, the disclosure relates to a compound of formula (I), or a pharmaceutically acceptable salt thereof, for use in a method of treating or lessening the severity of cancer pain in a subject, comprising administering to the subject the compound of formula (I), or the pharmaceutically acceptable salt thereof, once per day in a dose of about 750 mg.

In another aspect, the disclosure relates to a compound of formula (I), or a pharmaceutically acceptable salt thereof, for use in a method of treating or lessening the severity of cancer pain in a subject, comprising administering to the subject the compound of formula (I), or the pharmaceutically acceptable salt thereof, once per day in a dose of about 750 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of cancer pain in a subject, comprising administering to the subject the compound of formula (I), or the pharmaceutically acceptable salt thereof, once per day in a dose of about 1250 mg.

In another aspect, the disclosure relates to a compound of formula (I), or a pharmaceutically acceptable salt thereof, for use in a method of treating or lessening the severity of cancer pain in a subject, comprising administering to the subject the compound of formula (I), or the pharmaceutically acceptable salt thereof, once per day in a dose of about 1250 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of cancer pain in a subject, comprising administering to the subject the compound of formula (I), or the pharmaceutically acceptable salt thereof, once per day in a dose of 750 mg to 1250 mg.

In another aspect, the disclosure relates to a compound of formula (I), or a pharmaceutically acceptable salt thereof, for use in a method of treating or lessening the severity of cancer pain in a subject, comprising administering to the subject the compound of formula (I), or the pharmaceutically acceptable salt thereof, once per day in a dose of 750 mg to 1250 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of idiopathic pain in a subject, comprising administering to the subject the compound of formula (I), or the pharmaceutically acceptable salt thereof.

In another aspect, the disclosure relates to a compound of formula (I), or a pharmaceutically acceptable salt thereof, for use in a method of treating or lessening the severity of idiopathic pain in a subject, comprising administering to the subject the compound of formula (I), or the pharmaceutically acceptable salt thereof, once per day in a dose of about 250 mg.

In another aspect, the disclosure relates to a compound of formula (I), or a pharmaceutically acceptable salt thereof, for use in a method of treating or lessening the severity of idiopathic pain in a subject, comprising administering to the subject the compound of formula (I), or the pharmaceutically acceptable salt thereof, once per day in a dose of about 1000 mg.

In another aspect, the disclosure relates to a compound of formula (I), or a pharmaceutically acceptable salt thereof, for use in a method of treating or lessening the severity of idiopathic pain in a subject, comprising administering to the subject the compound of formula (I), or the pharmaceutically acceptable salt thereof, once per day in a dose of about 1000 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of idiopathic pain in a subject, comprising administering to the subject the compound of formula (I), or the pharmaceutically acceptable salt thereof, twice per day in a dose of about 500 mg (1000 mg per day).

In another aspect, the disclosure relates to a compound of formula (I), or a pharmaceutically acceptable salt thereof, for use in a method of treating or lessening the severity of idiopathic pain in a subject, comprising administering to the subject the compound of formula (I), or the pharmaceutically acceptable salt thereof, in a first dose of about 1500 mg and a subsequent dose of about 750 mg on the first day, and in two doses of about 750 mg per day each day after the first day.

In another aspect, the disclosure relates to a compound of formula (I), or a pharmaceutically acceptable salt thereof, for use in a method of treating or lessening the severity of idiopathic pain in a subject, comprising administering to the subject the compound of formula (I), or the pharmaceutically acceptable salt thereof, in a first dose of about 500 mg and a subsequent dose of about 250 mg on the first day, and in two doses of about 250 mg per day each day after the first day.

In another aspect, the disclosure relates to a compound of formula (I), or a pharmaceutically acceptable salt thereof, for use in a method of treating or lessening the severity of idiopathic pain in a subject, comprising administering to the subject the compound of formula (I), or the pharmaceutically acceptable salt thereof, once per day in a dose of about 750 mg.

In another aspect, the disclosure relates to a compound of formula (I), or a pharmaceutically acceptable salt thereof, for use in a method of treating or lessening the severity of idiopathic pain in a subject, comprising administering to the subject the compound of formula (I), or the pharmaceutically acceptable salt thereof, once per day in a dose of about 750 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of idiopathic pain in a subject, comprising administering to the subject the compound of formula (I), or the pharmaceutically acceptable salt thereof, once per day in a dose of about 1250 mg.

In another aspect, the disclosure relates to a compound of formula (I), or a pharmaceutically acceptable salt thereof, for use in a method of treating or lessening the severity of idiopathic pain in a subject, comprising administering to the subject the compound of formula (I), or the pharmaceutically acceptable salt thereof, once per day in a dose of about 1250 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of idiopathic pain in a subject, comprising administering to the subject the compound of formula (I), or the pharmaceutically acceptable salt thereof, once per day in a dose of 750 mg to 1250 mg.

In another aspect, the disclosure relates to a compound of formula (I), or a pharmaceutically acceptable salt thereof, for use in a method of treating or lessening the severity of idiopathic pain in a subject, comprising administering to the subject the compound of formula (I), or the pharmaceutically acceptable salt thereof, once per day in a dose of 750 mg to 1250 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of postsurgical pain in a subject, comprising administering to the subject the compound of formula (I), or the pharmaceutically acceptable salt thereof.

In another aspect, the disclosure relates to a compound of formula (I), or a pharmaceutically acceptable salt thereof, for use in a method of treating or lessening the severity of postsurgical pain in a subject, comprising administering to the subject the compound of formula (I), or the pharmaceutically acceptable salt thereof, once per day in a dose of about 250 mg.

In another aspect, the disclosure relates to a compound of formula (I), or a pharmaceutically acceptable salt thereof, for use in a method of treating or lessening the severity of postsurgical pain in a subject, comprising administering to the subject the compound of formula (I), or the pharmaceutically acceptable salt thereof, once per day in a dose of about 1000 mg.

In another aspect, the disclosure relates to a compound of formula (I), or a pharmaceutically acceptable salt thereof, for use in a method of treating or lessening the severity of postsurgical pain in a subject, comprising administering to the subject the compound of formula (I), or the pharmaceutically acceptable salt thereof, once per day in a dose of about 1000 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of postsurgical pain in a subject, comprising administering to the subject the compound of formula (I), or the pharmaceutically acceptable salt thereof, twice per day in a dose of about 500 mg (1000 mg per day).

In another aspect, the disclosure relates to a compound of formula (I), or a pharmaceutically acceptable salt thereof, for use in a method of treating or lessening the severity of postsurgical pain in a subject, comprising administering to the subject the compound of formula (I), or the pharmaceutically acceptable salt thereof, in a first dose of about 1500 mg and a subsequent dose of about 750 mg on the first day, and in two doses of about 750 mg per day each day after the first day.

In another aspect, the disclosure relates to a compound of formula (I), or a pharmaceutically acceptable salt thereof, for use in a method of treating or lessening the severity of postsurgical pain in a subject, comprising administering to the subject the compound of formula (I), or the pharmaceutically acceptable salt thereof, in a first dose of about 500 mg and a subsequent dose of about 250 mg on the first day, and in two doses of about 250 mg per day each day after the first day.

In another aspect, the disclosure relates to a compound of formula (I), or a pharmaceutically acceptable salt thereof, for use in a method of treating or lessening the severity of postsurgical pain in a subject, comprising administering to the subject the compound of formula (I), or the pharmaceutically acceptable salt thereof, once per day in a dose of about 750 mg.

In another aspect, the disclosure relates to a compound of formula (I), or a pharmaceutically acceptable salt thereof, for use in a method of treating or lessening the severity of postsurgical pain in a subject, comprising administering to the subject the compound of formula (I), or the pharmaceutically acceptable salt thereof, once per day in a dose of about 750 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of postsurgical pain in a subject, comprising administering to the subject the compound of formula (I), or the pharmaceutically acceptable salt thereof, once per day in a dose of about 1250 mg.

In another aspect, the disclosure relates to a compound of formula (I), or a pharmaceutically acceptable salt thereof, for use in a method of treating or lessening the severity of postsurgical pain in a subject, comprising administering to the subject the compound of formula (I), or the pharmaceutically acceptable salt thereof, once per day in a dose of about 1250 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of postsurgical pain in a subject, comprising administering to the subject the compound of formula (I), or the pharmaceutically acceptable salt thereof, once per day in a dose of 750 mg to 1250 mg.

In another aspect, the disclosure relates to a compound of formula (I), or a pharmaceutically acceptable salt thereof, for use in a method of treating or lessening the severity of postsurgical pain in a subject, comprising administering to the subject the compound of formula (I), or the pharmaceutically acceptable salt thereof, once per day in a dose of 750 mg to 1250 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of visceral pain in a subject, comprising administering to the subject the compound of formula (I), or the pharmaceutically acceptable salt thereof.

In another aspect, the disclosure relates to a compound of formula (I), or a pharmaceutically acceptable salt thereof, for use in a method of treating or lessening the severity of visceral pain in a subject, comprising administering to the subject the compound of formula (I), or the pharmaceutically acceptable salt thereof, once per day in a dose of about 250 mg.

In another aspect, the disclosure relates to a compound of formula (I), or a pharmaceutically acceptable salt thereof, for use in a method of treating or lessening the severity of visceral pain in a subject, comprising administering to the subject the compound of formula (I), or the pharmaceutically acceptable salt thereof, once per day in a dose of about 1000 mg.

In another aspect, the disclosure relates to a compound of formula (I), or a pharmaceutically acceptable salt thereof, for use in a method of treating or lessening the severity of visceral pain in a subject, comprising administering to the subject the compound of formula (I), or the pharmaceutically acceptable salt thereof, once per day in a dose of about 1000 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of visceral pain in a subject, comprising administering to the subject the compound of formula (I), or the pharmaceutically acceptable salt thereof, twice per day in a dose of about 500 mg (1000 mg per day).

In another aspect, the disclosure relates to a compound of formula (I), or a pharmaceutically acceptable salt thereof, for use in a method of treating or lessening the severity of visceral pain in a subject, comprising administering to the subject the compound of formula (I), or the pharmaceutically acceptable salt thereof, in a first dose of about 1500 mg and a subsequent dose of about 750 mg on the first day, and in two doses of about 750 mg per day each day after the first day.

In another aspect, the disclosure relates to a compound of formula (I), or a pharmaceutically acceptable salt thereof, for use in a method of treating or lessening the severity of visceral pain in a subject, comprising administering to the subject the compound of formula (I), or the pharmaceutically acceptable salt thereof, in a first dose of about 500 mg and a subsequent dose of about 250 mg on the first day, and in two doses of about 250 mg per day each day after the first day.

In another aspect, the disclosure relates to a compound of formula (I), or a pharmaceutically acceptable salt thereof, for use in a method of treating or lessening the severity of visceral pain in a subject, comprising administering to the subject the compound of formula (I), or the pharmaceutically acceptable salt thereof, once per day in a dose of about 750 mg.

In another aspect, the disclosure relates to a compound of formula (I), or a pharmaceutically acceptable salt thereof, for use in a method of treating or lessening the severity of visceral pain in a subject, comprising administering to the subject the compound of formula (I), or the pharmaceutically acceptable salt thereof, once per day in a dose of about 750 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of visceral pain in a subject, comprising administering to the subject the compound of formula (I), or the pharmaceutically acceptable salt thereof, once per day in a dose of about 1250 mg.

In another aspect, the disclosure relates to a compound of formula (I), or a pharmaceutically acceptable salt thereof, for use in a method of treating or lessening the severity of visceral pain in a subject, comprising administering to the subject the compound of formula (I), or the pharmaceutically acceptable salt thereof, once per day in a dose of about 1250 mg, for at least one week, at least two weeks, at least three weeks, at least four weeks, at least five weeks, or at least six weeks, or from one to six weeks.

In another aspect, the disclosure relates to a compound of formula (I), or a pharmaceutically acceptable salt thereof, for use in a method of treating or lessening the severity of visceral pain in a subject, comprising administering to the subject the compound of formula (I), or the pharmaceutically acceptable salt thereof, once per day in a dose of 750 mg to 1250 mg.

In another aspect, the disclosure relates to a compound of formula (I), or a pharmaceutically acceptable salt thereof, for use in a method of treating or lessening the severity of visceral pain in a subject, comprising administering to the subject the compound of formula (I), or the pharmaceutically acceptable salt thereof, once per day in a dose of 750 mg to 1250 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of pain in a subject, wherein the composition is prepared for administration of the compound of formula (I), or the pharmaceutically acceptable salt thereof, to the subject once per day in a dose of about 250 mg.

In another aspect, disclosure relates to a composition comprising a compound of formula (I), or a pharmaceutically acceptable salt thereof, for use in a method of treating or lessening the severity of pain in a subject, wherein the composition is prepared for administration of the compound of formula (I), or the pharmaceutically acceptable salt thereof, to the subject once per day in a dose of about 1000 mg.

In another aspect, disclosure relates to a composition comprising a compound of formula (I), or a pharmaceutically acceptable salt thereof, for use in a method of treating or lessening the severity of pain in a subject, wherein the composition is prepared for administration of the compound of formula (I), or the pharmaceutically acceptable salt thereof, to the subject once per day in a dose of about 1000 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of pain in a subject, wherein the composition is prepared for administration of the compound of formula (I), or the pharmaceutically acceptable salt thereof, to the subject twice per day in a dose of about 500 mg (1000 mg per day).

In another aspect, disclosure relates to a composition comprising a compound of formula (I), or a pharmaceutically acceptable salt thereof, for use in a method of treating or lessening the severity of pain in a subject, wherein the composition is prepared for administration of the compound of formula (I), or the pharmaceutically acceptable salt thereof, to the subject in a first dose of about 1500 mg and a subsequent dose of about 750 mg on the first day, and in two doses of about 750 mg per day each day after the first day.

In another aspect, disclosure relates to a composition comprising a compound of formula (I), or a pharmaceutically acceptable salt thereof, for use in a method of treating or lessening the severity of pain in a subject, wherein the composition is prepared for administration of the compound of formula (I), or the pharmaceutically acceptable salt thereof, to the subject in a first dose of about 500 mg and a subsequent dose of about 250 mg on the first day, and in two doses of about 250 mg per day each day after the first day.

In another aspect, disclosure relates to a composition comprising a compound of formula (I), or a pharmaceutically acceptable salt thereof, for use in a method of treating or lessening the severity of pain in a subject, wherein the composition is prepared for administration of the compound of formula (I), or the pharmaceutically acceptable salt thereof, to the subject once per day in a dose of about 750 mg.

In another aspect, disclosure relates to a composition comprising a compound of formula (I), or a pharmaceutically acceptable salt thereof, for use in a method of treating or lessening the severity of pain in a subject, wherein the composition is prepared for administration of the compound of formula (I), or the pharmaceutically acceptable salt thereof, to the subject once per day in a dose of about 750 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of pain in a subject, wherein the composition is prepared for administration of the compound of formula (I), or the pharmaceutically acceptable salt thereof, to the subject once per day in a dose of about 1250 mg.

In another aspect, disclosure relates to a composition comprising a compound of formula (I), or a pharmaceutically acceptable salt thereof, for use in a method of treating or lessening the severity of pain in a subject, wherein the composition is prepared for administration of the compound of formula (I), or the pharmaceutically acceptable salt thereof, to the subject once per day in a dose of about 1250 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of pain in a subject, wherein the composition is prepared for administration of the compound of formula (I), or the pharmaceutically acceptable salt thereof, to the subject once per day in a dose of 750 mg to 1250 mg.

In another aspect, disclosure relates to a composition comprising a compound of formula (I), or a pharmaceutically acceptable salt thereof, for use in a method of treating or lessening the severity of pain in a subject, wherein the composition is prepared for administration of the compound of formula (I), or the pharmaceutically acceptable salt thereof, to the subject once per day in a dose of 750 mg to 1250 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of chronic pain in a subject, wherein the composition is prepared for administration of the compound of formula (I), or the pharmaceutically acceptable salt thereof, to the subject.

In another aspect, disclosure relates to a composition comprising a compound of formula (I), or a pharmaceutically acceptable salt thereof, for use in a method of treating or lessening the severity of chronic pain in a subject, wherein the composition is prepared for administration of the compound of formula (I), or the pharmaceutically acceptable salt thereof, to the subject once per day in a dose of about 250 mg.

In another aspect, disclosure relates to a composition comprising a compound of formula (I), or a pharmaceutically acceptable salt thereof, for use in a method of treating or lessening the severity of chronic pain in a subject, wherein the composition is prepared for administration of the compound of formula (I), or the pharmaceutically acceptable salt thereof, to the subject once per day in a dose of about 1000 mg.

In another aspect, disclosure relates to a composition comprising a compound of formula (I), or a pharmaceutically acceptable salt thereof, for use in a method of treating or lessening the severity of chronic pain in a subject, wherein the composition is prepared for administration of the compound of formula (I), or the pharmaceutically acceptable salt thereof, to the subject once per day in a dose of about 1000 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of chronic pain in a subject, wherein the composition is prepared for administration of the compound of formula (I), or the pharmaceutically acceptable salt thereof, to the subject twice per day in a dose of about 500 mg (1000 mg per day).

In another aspect, disclosure relates to a composition comprising a compound of formula (I), or a pharmaceutically acceptable salt thereof, for use in a method of treating or lessening the severity of chronic pain in a subject, wherein the composition is prepared for administration of the compound of formula (I), or the pharmaceutically acceptable salt thereof, to the subject in a first dose of about 1500 mg and a subsequent dose of about 750 mg on the first day, and in two doses of about 750 mg per day each day after the first day.

In another aspect, disclosure relates to a composition comprising a compound of formula (I), or a pharmaceutically acceptable salt thereof, for use in a method of treating or lessening the severity of chronic pain in a subject, wherein the composition is prepared for administration of the compound of formula (I), or the pharmaceutically acceptable salt thereof, to the subject in a first dose of about 500 mg and a subsequent dose of about 250 mg on the first day, and in two doses of about 250 mg per day each day after the first day.

In another aspect, disclosure relates to a composition comprising a compound of formula (I), or a pharmaceutically acceptable salt thereof, for use in a method of treating or lessening the severity of chronic pain in a subject, wherein the composition is prepared for administration of the compound of formula (I), or the pharmaceutically acceptable salt thereof, to the subject once per day in a dose of about 750 mg.

In another aspect, disclosure relates to a composition comprising a compound of formula (I), or a pharmaceutically acceptable salt thereof, for use in a method of treating or lessening the severity of chronic pain in a subject, wherein the composition is prepared for administration of the compound of formula (I), or the pharmaceutically acceptable salt thereof, to the subject once per day in a dose of about 750 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of chronic pain in a subject, wherein the composition is prepared for administration of the compound of formula (I), or the pharmaceutically acceptable salt thereof, to the subject once per day in a dose of about 1250 mg.

In another aspect, disclosure relates to a composition comprising a compound of formula (I), or a pharmaceutically acceptable salt thereof, for use in a method of treating or lessening the severity of chronic pain in a subject, wherein the composition is prepared for administration of the compound of formula (I), or the pharmaceutically acceptable salt thereof, to the subject once per day in a dose of about 1250 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of chronic pain in a subject, wherein the composition is prepared for administration of the compound of formula (I), or the pharmaceutically acceptable salt thereof, to the subject once per day in a dose of about 750 mg to about 1250 mg.

In another aspect, disclosure relates to a composition comprising a compound of formula (I), or a pharmaceutically acceptable salt thereof, for use in a method of treating or lessening the severity of pain in a subject, wherein the composition is prepared for administration of the compound of formula (I), or the pharmaceutically acceptable salt thereof, to the subject once per day in a dose of 750 mg to 1250 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of gut pain in a subject, wherein the composition is prepared for administration of the compound of formula (I), or the pharmaceutically acceptable salt thereof, to the subject.

In another aspect, disclosure relates to a composition comprising a compound of formula (I), or a pharmaceutically acceptable salt thereof, for use in a method of treating or lessening the severity of gut pain in a subject, wherein the composition is prepared for administration of the compound of formula (I), or the pharmaceutically acceptable salt thereof, to the subject once per day in a dose of about 250 mg.

In another aspect, disclosure relates to a composition comprising a compound of formula (I), or a pharmaceutically acceptable salt thereof, for use in a method of treating or lessening the severity of gut pain in a subject, wherein the composition is prepared for administration of the compound of formula (I), or the pharmaceutically acceptable salt thereof, to the subject once per day in a dose of about 1000 mg.

In another aspect, disclosure relates to a composition comprising a compound of formula (I), or a pharmaceutically acceptable salt thereof, for use in a method of treating or lessening the severity of gut pain in a subject, wherein the composition is prepared for administration of the compound of formula (I), or the pharmaceutically acceptable salt thereof, to the subject once per day in a dose of about 1000 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of gut pain in a subject, wherein the composition is prepared for administration of the compound of formula (I), or the pharmaceutically acceptable salt thereof, to the subject twice per day in a dose of about 500 mg (1000 mg per day).

In another aspect, disclosure relates to a composition comprising a compound of formula (I), or a pharmaceutically acceptable salt thereof, for use in a method of treating or lessening the severity of gut pain in a subject, wherein the composition is prepared for administration of the compound of formula (I), or the pharmaceutically acceptable salt thereof, to the subject in a first dose of about 1500 mg and a subsequent dose of about 750 mg on the first day, and in two doses of about 750 mg per day each day after the first day.

In another aspect, disclosure relates to a composition comprising a compound of formula (I), or a pharmaceutically acceptable salt thereof, for use in a method of treating or lessening the severity of gut pain in a subject, wherein the composition is prepared for administration of the compound of formula (I), or the pharmaceutically acceptable salt thereof, to the subject in a first dose of about 500 mg and a subsequent dose of about 250 mg on the first day, and in two doses of about 250 mg per day each day after the first day.

In another aspect, disclosure relates to a composition comprising a compound of formula (I), or a pharmaceutically acceptable salt thereof, for use in a method of treating or lessening the severity of gut pain in a subject, wherein the composition is prepared for administration of the compound of formula (I), or the pharmaceutically acceptable salt thereof, to the subject once per day in a dose of about 750 mg.

In another aspect, disclosure relates to a composition comprising a compound of formula (I), or a pharmaceutically acceptable salt thereof, for use in a method of treating or lessening the severity of gut pain in a subject, wherein the composition is prepared for administration of the compound of formula (I), or the pharmaceutically acceptable salt thereof, to the subject once per day in a dose of about 750 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of gut pain in a subject, wherein the composition is prepared for administration of the compound of formula (I), or the pharmaceutically acceptable salt thereof, to the subject once per day in a dose of about 1250 mg.

In another aspect, disclosure relates to a composition comprising a compound of formula (I), or a pharmaceutically acceptable salt thereof, for use in a method of treating or lessening the severity of gut pain in a subject, wherein the composition is prepared for administration of the compound of formula (I), or the pharmaceutically acceptable salt thereof, to the subject once per day in a dose of about 1250 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of gut pain in a subject, wherein the composition is prepared for administration of the compound of formula (I), or the pharmaceutically acceptable salt thereof, to the subject once per day in a dose of 750 mg to 1250 mg.

In another aspect, disclosure relates to a composition comprising a compound of formula (I), or a pharmaceutically acceptable salt thereof, for use in a method of treating or lessening the severity of gut pain in a subject, wherein the composition is prepared for administration of the compound of formula (I), or the pharmaceutically acceptable salt thereof, to the subject once per day in a dose of 750 mg to 1250 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of neuropathic pain in a subject, wherein the composition is prepared for administration of the compound of formula (I), or the pharmaceutically acceptable salt thereof, to the subject.

In another aspect, disclosure relates to a composition comprising a compound of formula (I), or a pharmaceutically acceptable salt thereof, for use in a method of treating or lessening the severity of neuropathic pain in a subject, wherein the composition is prepared for administration of the compound of formula (I), or the pharmaceutically acceptable salt thereof, to the subject once per day in a dose of about 250 mg.

In another aspect, disclosure relates to a composition comprising a compound of formula (I), or a pharmaceutically acceptable salt thereof, for use in a method of treating or lessening the severity of neuropathic pain in a subject, wherein the composition is prepared for administration of the compound of formula (I), or the pharmaceutically acceptable salt thereof, to the subject once per day in a dose of about 1000 mg.

In another aspect, disclosure relates to a composition comprising a compound of formula (I), or a pharmaceutically acceptable salt thereof, for use in a method of treating or lessening the severity of neuropathic pain in a subject, wherein the composition is prepared for administration of the compound of formula (I), or the pharmaceutically acceptable salt thereof, to the subject once per day in a dose of about 1000 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of neuropathic pain in a subject, wherein the composition is prepared for administration of the compound of formula (I), or the pharmaceutically acceptable salt thereof, to the subject twice per day in a dose of about 500 mg (1000 mg per day).

In another aspect, disclosure relates to a composition comprising a compound of formula (I), or a pharmaceutically acceptable salt thereof, for use in a method of treating or lessening the severity of neuropathic pain in a subject, wherein the composition is prepared for administration of the compound of formula (I), or the pharmaceutically acceptable salt thereof, to the subject in a first dose of about 1500 mg and a subsequent dose of about 750 mg on the first day, and in two doses of about 750 mg per day each day after the first day.

In another aspect, disclosure relates to a composition comprising a compound of formula (I), or a pharmaceutically acceptable salt thereof, for use in a method of treating or lessening the severity of neuropathic pain in a subject, wherein the composition is prepared for administration of the compound of formula (I), or the pharmaceutically acceptable salt thereof, to the subject in a first dose of about 500 mg and a subsequent dose of about 250 mg on the first day, and in two doses of about 250 mg per day each day after the first day.

In another aspect, disclosure relates to a composition comprising a compound of formula (I), or a pharmaceutically acceptable salt thereof, for use in a method of treating or lessening the severity of neuropathic pain in a subject, wherein the composition is prepared for administration of the compound of formula (I), or the pharmaceutically acceptable salt thereof, to the subject once per day in a dose of about 750 mg.

In another aspect, disclosure relates to a composition comprising a compound of formula (I), or a pharmaceutically acceptable salt thereof, for use in a method of treating or lessening the severity of neuropathic pain in a subject, wherein the composition is prepared for administration of the compound of formula (I), or the pharmaceutically acceptable salt thereof, to the subject once per day in a dose of about 750 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of neuropathic pain in a subject, wherein the composition is prepared for administration of the compound of formula (I), or the pharmaceutically acceptable salt thereof, to the subject once per day in a dose of about 1250 mg.

In another aspect, disclosure relates to a composition comprising a compound of formula (I), or a pharmaceutically acceptable salt thereof, for use in a method of treating or lessening the severity of neuropathic pain in a subject, wherein the composition is prepared for administration of the compound of formula (I), or the pharmaceutically acceptable salt thereof, to the subject once per day in a dose of about 1250 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of neuropathic pain in a subject, wherein the composition is prepared for administration of the compound of formula (I), or the pharmaceutically acceptable salt thereof, to the subject once per day in a dose of 750 mg to 1250 mg.

In another aspect, disclosure relates to a composition comprising a compound of formula (I), or a pharmaceutically acceptable salt thereof, for use in a method of treating or lessening the severity of neuropathic pain in a subject, wherein the composition is prepared for administration of the compound of formula (I), or the pharmaceutically acceptable salt thereof, to the subject once per day in a dose of 750 mg to 1250 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of idiopathic small fiber neuropathy in a subject, wherein the composition is prepared for administration of the compound of formula (I), or the pharmaceutically acceptable salt thereof, to the subject.

In another aspect, disclosure relates to a composition comprising a compound of formula (I), or a pharmaceutically acceptable salt thereof, for use in a method of treating or lessening the severity of idiopathic small fiber neuropathy in a subject, wherein the composition is prepared for administration of the compound of formula (I), or the pharmaceutically acceptable salt thereof, to the subject once per day in a dose of about 250 mg.

In another aspect, disclosure relates to a composition comprising a compound of formula (I), or a pharmaceutically acceptable salt thereof, for use in a method of treating or lessening the severity of idiopathic small fiber neuropathy in a subject, wherein the composition is prepared for administration of the compound of formula (I), or the pharmaceutically acceptable salt thereof, to the subject once per day in a dose of about 1000 mg.

In another aspect, disclosure relates to a composition comprising a compound of formula (I), or a pharmaceutically acceptable salt thereof, for use in a method of treating or lessening the severity of idiopathic small fiber neuropathy in a subject, wherein the composition is prepared for administration of the compound of formula (I), or the pharmaceutically acceptable salt thereof, to the subject once per day in a dose of about 1000 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of idiopathic small fiber neuropathy in a subject, wherein the composition is prepared for administration of the compound of formula (I), or the pharmaceutically acceptable salt thereof, to the subject twice per day in a dose of about 500 mg (1000 mg per day).

In another aspect, disclosure relates to a composition comprising a compound of formula (I), or a pharmaceutically acceptable salt thereof, for use in a method of treating or lessening the severity of idiopathic small fiber neuropathy in a subject, wherein the composition is prepared for administration of the compound of formula (I), or the pharmaceutically acceptable salt thereof, to the subject in a first dose of about 1500 mg and a subsequent dose of about 750 mg on the first day, and in two doses of about 750 mg per day each day after the first day.

In another aspect, disclosure relates to a composition comprising a compound of formula (I), or a pharmaceutically acceptable salt thereof, for use in a method of treating or lessening the severity of idiopathic small fiber neuropathy in a subject, wherein the composition is prepared for administration of the compound of formula (I), or the pharmaceutically acceptable salt thereof, to the subject in a first dose of about 500 mg and a subsequent dose of about 250 mg on the first day, and in two doses of about 250 mg per day each day after the first day.

In another aspect, disclosure relates to a composition comprising a compound of formula (I), or a pharmaceutically acceptable salt thereof, for use in a method of treating or lessening the severity of idiopathic small fiber neuropathy in a subject, wherein the composition is prepared for administration of the compound of formula (I), or the pharmaceutically acceptable salt thereof, to the subject once per day in a dose of about 750 mg.

In another aspect, disclosure relates to a composition comprising a compound of formula (I), or a pharmaceutically acceptable salt thereof, for use in a method of treating or lessening the severity of idiopathic small fiber neuropathy in a subject, wherein the composition is prepared for administration of the compound of formula (I), or the pharmaceutically acceptable salt thereof, to the subject once per day in a dose of about 750 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of idiopathic small fiber neuropathy in a subject, wherein the composition is prepared for administration of the compound of formula (I), or the pharmaceutically acceptable salt thereof, to the subject once per day in a dose of about 1250 mg.

In another aspect, disclosure relates to a composition comprising a compound of formula (I), or a pharmaceutically acceptable salt thereof, for use in a method of treating or lessening the severity of idiopathic small fiber neuropathy in a subject, wherein the composition is prepared for administration of the compound of formula (I), or the pharmaceutically acceptable salt thereof, to the subject once per day in a dose of about 1250 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of idiopathic small fiber neuropathy in a subject, wherein the composition is prepared for administration of the compound of formula (I), or the pharmaceutically acceptable salt thereof, to the subject once per day in a dose of 750 mg to 1250 mg.

In another aspect, disclosure relates to a composition comprising a compound of formula (I), or a pharmaceutically acceptable salt thereof, for use in a method of treating or lessening the severity of idiopathic small fiber neuropathy in a subject, wherein the composition is prepared for administration of the compound of formula (I), or the pharmaceutically acceptable salt thereof, to the subject once per day in a dose of 750 mg to 1250 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of musculoskeletal pain in a subject, wherein the composition is prepared for administration of the compound of formula (I), or the pharmaceutically acceptable salt thereof, to the subject.

In another aspect, disclosure relates to a composition comprising a compound of formula (I), or a pharmaceutically acceptable salt thereof, for use in a method of treating or lessening the severity of musculoskeletal pain in a subject, wherein the composition is prepared for administration of the compound of formula (I), or the pharmaceutically acceptable salt thereof, to the subject once per day in a dose of about 250 mg.

In another aspect, disclosure relates to a composition comprising a compound of formula (I), or a pharmaceutically acceptable salt thereof, for use in a method of treating or lessening the severity of musculoskeletal pain in a subject, wherein the composition is prepared for administration of the compound of formula (I), or the pharmaceutically acceptable salt thereof, to the subject once per day in a dose of about 1000 mg.

In another aspect, disclosure relates to a composition comprising a compound of formula (I), or a pharmaceutically acceptable salt thereof, for use in a method of treating or lessening the severity of musculoskeletal pain in a subject, wherein the composition is prepared for administration of the compound of formula (I), or the pharmaceutically acceptable salt thereof, to the subject once per day in a dose of about 1000 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of musculoskeletal pain in a subject, wherein the composition is prepared for administration of the compound of formula (I), or the pharmaceutically acceptable salt thereof, to the subject twice per day in a dose of about 500 mg (1000 mg per day).

In another aspect, disclosure relates to a composition comprising a compound of formula (I), or a pharmaceutically acceptable salt thereof, for use in a method of treating or lessening the severity of musculoskeletal pain in a subject, wherein the composition is prepared for administration of the compound of formula (I), or the pharmaceutically acceptable salt thereof, to the subject in a first dose of about 1500 mg and a subsequent dose of about 750 mg on the first day, and in two doses of about 750 mg per day each day after the first day.

In another aspect, disclosure relates to a composition comprising a compound of formula (I), or a pharmaceutically acceptable salt thereof, for use in a method of treating or lessening the severity of musculoskeletal pain in a subject, wherein the composition is prepared for administration of the compound of formula (I), or the pharmaceutically acceptable salt thereof, to the subject in a first dose of about 500 mg and a subsequent dose of about 250 mg on the first day, and in two doses of about 250 mg per day each day after the first day.

In another aspect, disclosure relates to a composition comprising a compound of formula (I), or a pharmaceutically acceptable salt thereof, for use in a method of treating or lessening the severity of musculoskeletal pain in a subject, wherein the composition is prepared for administration of the compound of formula (I), or the pharmaceutically acceptable salt thereof, to the subject once per day in a dose of about 750 mg.

In another aspect, disclosure relates to a composition comprising a compound of formula (I), or a pharmaceutically acceptable salt thereof, for use in a method of treating or lessening the severity of musculoskeletal pain in a subject, wherein the composition is prepared for administration of the compound of formula (I), or the pharmaceutically acceptable salt thereof, to the subject once per day in a dose of about 750 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of musculoskeletal pain in a subject, wherein the composition is prepared for administration of the compound of formula (I), or the pharmaceutically acceptable salt thereof, to the subject once per day in a dose of about 1250 mg.

In another aspect, disclosure relates to a composition comprising a compound of formula (I), or a pharmaceutically acceptable salt thereof, for use in a method of treating or lessening the severity of musculoskeletal pain in a subject, wherein the composition is prepared for administration of the compound of formula (I), or the pharmaceutically acceptable salt thereof, to the subject once per day in a dose of about 1250 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of musculoskeletal pain in a subject, wherein the composition is prepared for administration of the compound of formula (I), or the pharmaceutically acceptable salt thereof, to the subject once per day in a dose of 750 mg to 1250 mg.

In another aspect, disclosure relates to a composition comprising a compound of formula (I), or a pharmaceutically acceptable salt thereof, for use in a method of treating or lessening the severity of musculoskeletal pain in a subject, wherein the composition is prepared for administration of the compound of formula (I), or the pharmaceutically acceptable salt thereof, to the subject once per day in a dose of 750 mg to 1250 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of osteoarthritis pain in a subject, wherein the composition is prepared for administration of the compound of formula (I), or the pharmaceutically acceptable salt thereof, to the subject.

In another aspect, disclosure relates to a composition comprising a compound of formula (I), or a pharmaceutically acceptable salt thereof, for use in a method of treating or lessening the severity of osteoarthritis pain in a subject, wherein the composition is prepared for administration of the compound of formula (I), or the pharmaceutically acceptable salt thereof, to the subject once per day in a dose of about 250 mg.

In another aspect, disclosure relates to a composition comprising a compound of formula (I), or a pharmaceutically acceptable salt thereof, for use in a method of treating or lessening the severity of osteoarthritis pain in a subject, wherein the composition is prepared for administration of the compound of formula (I), or the pharmaceutically acceptable salt thereof, to the subject once per day in a dose of about 1000 mg.

In another aspect, disclosure relates to a composition comprising a compound of formula (I), or a pharmaceutically acceptable salt thereof, for use in a method of treating or lessening the severity of osteoarthritis pain in a subject, wherein the composition is prepared for administration of the compound of formula (I), or the pharmaceutically acceptable salt thereof, to the subject once per day in a dose of about 1000 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of osteoarthritis pain in a subject, wherein the composition is prepared for administration of the compound of formula (I), or the pharmaceutically acceptable salt thereof, to the subject twice per day in a dose of about 500 mg (1000 mg per day).

In another aspect, disclosure relates to a composition comprising a compound of formula (I), or a pharmaceutically acceptable salt thereof, for use in a method of treating or lessening the severity of osteoarthritis pain in a subject, wherein the composition is prepared for administration of the compound of formula (I), or the pharmaceutically acceptable salt thereof, to the subject in a first dose of about 1500 mg and a subsequent dose of about 750 mg on the first day, and in two doses of about 750 mg per day each day after the first day.

In another aspect, disclosure relates to a composition comprising a compound of formula (I), or a pharmaceutically acceptable salt thereof, for use in a method of treating or lessening the severity of osteoarthritis pain in a subject, wherein the composition is prepared for administration of the compound of formula (I), or the pharmaceutically acceptable salt thereof, to the subject in a first dose of about 500 mg and a subsequent dose of about 250 mg on the first day, and in two doses of about 250 mg per day each day after the first day.

In another aspect, disclosure relates to a composition comprising a compound of formula (I), or a pharmaceutically acceptable salt thereof, for use in a method of treating or lessening the severity of osteoarthritis pain in a subject, wherein the composition is prepared for administration of the compound of formula (I), or the pharmaceutically acceptable salt thereof, to the subject once per day in a dose of about 750 mg.

In another aspect, disclosure relates to a composition comprising a compound of formula (I), or a pharmaceutically acceptable salt thereof, for use in a method of treating or lessening the severity of osteoarthritis pain in a subject, wherein the composition is prepared for administration of the compound of formula (I), or the pharmaceutically acceptable salt thereof, to the subject once per day in a dose of about 750 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of osteoarthritis pain in a subject, wherein the composition is prepared for administration of the compound of formula (I), or the pharmaceutically acceptable salt thereof, to the subject once per day in a dose of about 1250 mg.

In another aspect, disclosure relates to a composition comprising a compound of formula (I), or a pharmaceutically acceptable salt thereof, for use in a method of treating or lessening the severity of osteoarthritis pain in a subject, wherein the composition is prepared for administration of the compound of formula (I), or the pharmaceutically acceptable salt thereof, to the subject once per day in a dose of about 1250 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of osteoarthritis pain in a subject, wherein the composition is prepared for administration of the compound of formula (I), or the pharmaceutically acceptable salt thereof, to the subject once per day in a dose of 750 mg to 1250 mg.

In another aspect, disclosure relates to a composition comprising a compound of formula (I), or a pharmaceutically acceptable salt thereof, for use in a method of treating or lessening the severity of osteoarthritis pain in a subject, wherein the composition is prepared for administration of the compound of formula (I), or the pharmaceutically acceptable salt thereof, to the subject once per day in a dose of 750 mg to 1250 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of acute pain in a subject, wherein the composition is prepared for administration of the compound of formula (I), or the pharmaceutically acceptable salt thereof, to the subject.

In another aspect, disclosure relates to a composition comprising a compound of formula (I), or a pharmaceutically acceptable salt thereof, for use in a method of treating or lessening the severity of acute pain in a subject, wherein the composition is prepared for administration of the compound of formula (I), or the pharmaceutically acceptable salt thereof, to the subject once per day in a dose of about 250 mg.

In another aspect, disclosure relates to a composition comprising a compound of formula (I), or a pharmaceutically acceptable salt thereof, for use in a method of treating or lessening the severity of acute pain in a subject, wherein the composition is prepared for administration of the compound of formula (I), or the pharmaceutically acceptable salt thereof, to the subject once per day in a dose of about 1000 mg.

In another aspect, disclosure relates to a composition comprising a compound of formula (I), or a pharmaceutically acceptable salt thereof, for use in a method of treating or lessening the severity of acute pain in a subject, wherein the composition is prepared for administration of the compound of formula (I), or the pharmaceutically acceptable salt thereof, to the subject once per day in a dose of about 1000 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of acute pain in a subject, wherein the composition is prepared for administration of the compound of formula (I), or the pharmaceutically acceptable salt thereof, to the subject twice per day in a dose of about 500 mg (1000 mg per day).

In another aspect, disclosure relates to a composition comprising a compound of formula (I), or a pharmaceutically acceptable salt thereof, for use in a method of treating or lessening the severity of acute pain in a subject, wherein the composition is prepared for administration of the compound of formula (I), or the pharmaceutically acceptable salt thereof, to the subject in a first dose of about 1500 mg and a subsequent dose of about 750 mg on the first day, and in two doses of about 750 mg per day each day after the first day.

In another aspect, disclosure relates to a composition comprising a compound of formula (I), or a pharmaceutically acceptable salt thereof, for use in a method of treating or lessening the severity of acute pain in a subject, wherein the composition is prepared for administration of the compound of formula (I), or the pharmaceutically acceptable salt thereof, to the subject in a first dose of about 500 mg and a subsequent dose of about 250 mg on the first day, and in two doses of about 250 mg per day each day after the first day.

In another aspect, disclosure relates to a composition comprising a compound of formula (I), or a pharmaceutically acceptable salt thereof, for use in a method of treating or lessening the severity of acute pain in a subject, wherein the composition is prepared for administration of the compound of formula (I), or the pharmaceutically acceptable salt thereof, to the subject once per day in a dose of about 750 mg.

In another aspect, disclosure relates to a composition comprising a compound of formula (I), or a pharmaceutically acceptable salt thereof, for use in a method of treating or lessening the severity of acute pain in a subject, wherein the composition is prepared for administration of the compound of formula (I), or the pharmaceutically acceptable salt thereof, to the subject once per day in a dose of about 750 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of acute pain in a subject, wherein the composition is prepared for administration of the compound of formula (I), or the pharmaceutically acceptable salt thereof, to the subject once per day in a dose of about 1250 mg.

In another aspect, disclosure relates to a composition comprising a compound of formula (I), or a pharmaceutically acceptable salt thereof, for use in a method of treating or lessening the severity of acute pain in a subject, wherein the composition is prepared for administration of the compound of formula (I), or the pharmaceutically acceptable salt thereof, to the subject once per day in a dose of about 1250 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of acute pain in a subject, wherein the composition is prepared for administration of the compound of formula (I), or the pharmaceutically acceptable salt thereof, to the subject once per day in a dose of 750 mg to 1250 mg.

In another aspect, disclosure relates to a composition comprising a compound of formula (I), or a pharmaceutically acceptable salt thereof, for use in a method of treating or lessening the severity of acute pain in a subject, wherein the composition is prepared for administration of the compound of formula (I), or the pharmaceutically acceptable salt thereof, to the subject once per day in a dose of 750 mg to 1250 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of inflammatory pain in a subject, wherein the composition is prepared for administration of the compound of formula (I), or the pharmaceutically acceptable salt thereof, to the subject.

In another aspect, disclosure relates to a composition comprising a compound of formula (I), or a pharmaceutically acceptable salt thereof, for use in a method of treating or lessening the severity of inflammatory pain in a subject, wherein the composition is prepared for administration of the compound of formula (I), or the pharmaceutically acceptable salt thereof, to the subject once per day in a dose of about 250 mg.

In another aspect, disclosure relates to a composition comprising a compound of formula (I), or a pharmaceutically acceptable salt thereof, for use in a method of treating or lessening the severity of inflammatory pain in a subject, wherein the composition is prepared for administration of the compound of formula (I), or the pharmaceutically acceptable salt thereof, to the subject once per day in a dose of about 1000 mg.

In another aspect, disclosure relates to a composition comprising a compound of formula (I), or a pharmaceutically acceptable salt thereof, for use in a method of treating or lessening the severity of inflammatory pain in a subject, wherein the composition is prepared for administration of the compound of formula (I), or the pharmaceutically acceptable salt thereof, to the subject once per day in a dose of about 1000 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of inflammatory pain in a subject, wherein the composition is prepared for administration of the compound of formula (I), or the pharmaceutically acceptable salt thereof, to the subject twice per day in a dose of about 500 mg (1000 mg per day).

In another aspect, disclosure relates to a composition comprising a compound of formula (I), or a pharmaceutically acceptable salt thereof, for use in a method of treating or lessening the severity of inflammatory pain in a subject, wherein the composition is prepared for administration of the compound of formula (I), or the pharmaceutically acceptable salt thereof, to the subject in a first dose of about 1500 mg and a subsequent dose of about 750 mg on the first day, and in two doses of about 750 mg per day each day after the first day.

In another aspect, disclosure relates to a composition comprising a compound of formula (I), or a pharmaceutically acceptable salt thereof, for use in a method of treating or lessening the severity of inflammatory pain in a subject, wherein the composition is prepared for administration of the compound of formula (I), or the pharmaceutically acceptable salt thereof, to the subject in a first dose of about 500 mg and a subsequent dose of about 250 mg on the first day, and in two doses of about 250 mg per day each day after the first day.

In another aspect, disclosure relates to a composition comprising a compound of formula (I), or a pharmaceutically acceptable salt thereof, for use in a method of treating or lessening the severity of inflammatory pain in a subject, wherein the composition is prepared for administration of the compound of formula (I), or the pharmaceutically acceptable salt thereof, to the subject once per day in a dose of about 750 mg.

In another aspect, disclosure relates to a composition comprising a compound of formula (I), or a pharmaceutically acceptable salt thereof, for use in a method of treating or lessening the severity of inflammatory pain in a subject, wherein the composition is prepared for administration of the compound of formula (I), or the pharmaceutically acceptable salt thereof, to the subject once per day in a dose of about 750 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of inflammatory pain in a subject, wherein the composition is prepared for administration of the compound of formula (I), or the pharmaceutically acceptable salt thereof, to the subject once per day in a dose of about 1250 mg.

In another aspect, disclosure relates to a composition comprising a compound of formula (I), or a pharmaceutically acceptable salt thereof, for use in a method of treating or lessening the severity of inflammatory pain in a subject, wherein the composition is prepared for administration of the compound of formula (I), or the pharmaceutically acceptable salt thereof, to the subject once per day in a dose of about 1250 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of inflammatory pain in a subject, wherein the composition is prepared for administration of the compound of formula (I), or the pharmaceutically acceptable salt thereof, to the subject once per day in a dose of 750 mg to 1250 mg.

In another aspect, disclosure relates to a composition comprising a compound of formula (I), or a pharmaceutically acceptable salt thereof, for use in a method of treating or lessening the severity of inflammatory pain in a subject, wherein the composition is prepared for administration of the compound of formula (I), or the pharmaceutically acceptable salt thereof, to the subject once per day in a dose of 750 mg to 1250 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of cancer pain in a subject, wherein the composition is prepared for administration of the compound of formula (I), or the pharmaceutically acceptable salt thereof, to the subject.

In another aspect, disclosure relates to a composition comprising a compound of formula (I), or a pharmaceutically acceptable salt thereof, for use in a method of treating or lessening the severity of cancer pain in a subject, wherein the composition is prepared for administration of the compound of formula (I), or the pharmaceutically acceptable salt thereof, to the subject once per day in a dose of about 250 mg.

In another aspect, disclosure relates to a composition comprising a compound of formula (I), or a pharmaceutically acceptable salt thereof, for use in a method of treating or lessening the severity of cancer pain in a subject, wherein the composition is prepared for administration of the compound of formula (I), or the pharmaceutically acceptable salt thereof, to the subject once per day in a dose of about 1000 mg.

In another aspect, disclosure relates to a composition comprising a compound of formula (I), or a pharmaceutically acceptable salt thereof, for use in a method of treating or lessening the severity of cancer pain in a subject, wherein the composition is prepared for administration of the compound of formula (I), or the pharmaceutically acceptable salt thereof, to the subject once per day in a dose of about 1000 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of cancer pain in a subject, wherein the composition is prepared for administration of the compound of formula (I), or the pharmaceutically acceptable salt thereof, to the subject twice per day in a dose of about 500 mg (1000 mg per day).

In another aspect, disclosure relates to a composition comprising a compound of formula (I), or a pharmaceutically acceptable salt thereof, for use in a method of treating or lessening the severity of cancer pain in a subject, wherein the composition is prepared for administration of the compound of formula (I), or the pharmaceutically acceptable salt thereof, to the subject in a first dose of about 1500 mg and a subsequent dose of about 750 mg on the first day, and in two doses of about 750 mg per day each day after the first day.

In another aspect, disclosure relates to a composition comprising a compound of formula (I), or a pharmaceutically acceptable salt thereof, for use in a method of treating or lessening the severity of cancer pain in a subject, wherein the composition is prepared for administration of the compound of formula (I), or the pharmaceutically acceptable salt thereof, to the subject in a first dose of about 500 mg and a subsequent dose of about 250 mg on the first day, and in two doses of about 250 mg per day each day after the first day.

In another aspect, disclosure relates to a composition comprising a compound of formula (I), or a pharmaceutically acceptable salt thereof, for use in a method of treating or lessening the severity of cancer pain in a subject, wherein the composition is prepared for administration of the compound of formula (I), or the pharmaceutically acceptable salt thereof, to the subject once per day in a dose of about 750 mg.

In another aspect, disclosure relates to a composition comprising a compound of formula (I), or a pharmaceutically acceptable salt thereof, for use in a method of treating or lessening the severity of cancer pain in a subject, wherein the composition is prepared for administration of the compound of formula (I), or the pharmaceutically acceptable salt thereof, to the subject once per day in a dose of about 750 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of cancer pain in a subject, wherein the composition is prepared for administration of the compound of formula (I), or the pharmaceutically acceptable salt thereof, to the subject once per day in a dose of about 1250 mg.

In another aspect, disclosure relates to a composition comprising a compound of formula (I), or a pharmaceutically acceptable salt thereof, for use in a method of treating or lessening the severity of cancer pain in a subject, wherein the composition is prepared for administration of the compound of formula (I), or the pharmaceutically acceptable salt thereof, to the subject once per day in a dose of about 1250 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of cancer pain in a subject, wherein the composition is prepared for administration of the compound of formula (I), or the pharmaceutically acceptable salt thereof, to the subject once per day in a dose of 750 mg to 1250 mg.

In another aspect, disclosure relates to a composition comprising a compound of formula (I), or a pharmaceutically acceptable salt thereof, for use in a method of treating or lessening the severity of cancer pain in a subject, wherein the composition is prepared for administration of the compound of formula (I), or the pharmaceutically acceptable salt thereof, to the subject once per day in a dose of 750 mg to 1250 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of idiopathic pain in a subject, wherein the composition is prepared for administration of the compound of formula (I), or the pharmaceutically acceptable salt thereof, to the subject.

In another aspect, disclosure relates to a composition comprising a compound of formula (I), or a pharmaceutically acceptable salt thereof, for use in a method of treating or lessening the severity of idiopathic pain in a subject, wherein the composition is prepared for administration of the compound of formula (I), or the pharmaceutically acceptable salt thereof, to the subject once per day in a dose of about 250 mg.

In another aspect, disclosure relates to a composition comprising a compound of formula (I), or a pharmaceutically acceptable salt thereof, for use in a method of treating or lessening the severity of idiopathic pain in a subject, wherein the composition is prepared for administration of the compound of formula (I), or the pharmaceutically acceptable salt thereof, to the subject once per day in a dose of about 1000 mg.

In another aspect, disclosure relates to a composition comprising a compound of formula (I), or a pharmaceutically acceptable salt thereof, for use in a method of treating or lessening the severity of idiopathic pain in a subject, wherein the composition is prepared for administration of the compound of formula (I), or the pharmaceutically acceptable salt thereof, to the subject once per day in a dose of about 1000 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of idiopathic pain in a subject, wherein the composition is prepared for administration of the compound of formula (I), or the pharmaceutically acceptable salt thereof, to the subject twice per day in a dose of about 500 mg (1000 mg per day).

In another aspect, disclosure relates to a composition comprising a compound of formula (I), or a pharmaceutically acceptable salt thereof, for use in a method of treating or lessening the severity of idiopathic pain in a subject, wherein the composition is prepared for administration of the compound of formula (I), or the pharmaceutically acceptable salt thereof, to the subject in a first dose of about 1500 mg and a subsequent dose of about 750 mg on the first day, and in two doses of about 750 mg per day each day after the first day.

In another aspect, disclosure relates to a composition comprising a compound of formula (I), or a pharmaceutically acceptable salt thereof, for use in a method of treating or lessening the severity of idiopathic pain in a subject, wherein the composition is prepared for administration of the compound of formula (I), or the pharmaceutically acceptable salt thereof, to the subject in a first dose of about 500 mg and a subsequent dose of about 250 mg on the first day, and in two doses of about 250 mg per day each day after the first day.

In another aspect, disclosure relates to a composition comprising a compound of formula (I), or a pharmaceutically acceptable salt thereof, for use in a method of treating or lessening the severity of idiopathic pain in a subject, wherein the composition is prepared for administration of the compound of formula (I), or the pharmaceutically acceptable salt thereof, to the subject once per day in a dose of about 750 mg.

In another aspect, disclosure relates to a composition comprising a compound of formula (I), or a pharmaceutically acceptable salt thereof, for use in a method of treating or lessening the severity of idiopathic pain in a subject, wherein the composition is prepared for administration of the compound of formula (I), or the pharmaceutically acceptable salt thereof, to the subject once per day in a dose of about 750 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of idiopathic pain in a subject, wherein the composition is prepared for administration of the compound of formula (I), or the pharmaceutically acceptable salt thereof, to the subject once per day in a dose of about 1250 mg.

In another aspect, disclosure relates to a composition comprising a compound of formula (I), or a pharmaceutically acceptable salt thereof, for use in a method of treating or lessening the severity of idiopathic pain in a subject, wherein the composition is prepared for administration of the compound of formula (I), or the pharmaceutically acceptable salt thereof, to the subject once per day in a dose of about 1250 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of idiopathic pain in a subject, wherein the composition is prepared for administration of the compound of formula (I), or the pharmaceutically acceptable salt thereof, to the subject once per day in a dose of 750 mg to 1250 mg.

In another aspect, disclosure relates to a composition comprising a compound of formula (I), or a pharmaceutically acceptable salt thereof, for use in a method of treating or lessening the severity of idiopathic pain in a subject, wherein the composition is prepared for administration of the compound of formula (I), or the pharmaceutically acceptable salt thereof, to the subject once per day in a dose of 750 mg to 1250 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of postsurgical pain in a subject, wherein the composition is prepared for administration of the compound of formula (I), or the pharmaceutically acceptable salt thereof, to the subject.

In another aspect, disclosure relates to a composition comprising a compound of formula (I), or a pharmaceutically acceptable salt thereof, for use in a method of treating or lessening the severity of postsurgical pain in a subject, wherein the composition is prepared for administration of the compound of formula (I), or the pharmaceutically acceptable salt thereof, to the subject once per day in a dose of about 250 mg.

In another aspect, disclosure relates to a composition comprising a compound of formula (I), or a pharmaceutically acceptable salt thereof, for use in a method of treating or lessening the severity of postsurgical pain in a subject, wherein the composition is prepared for administration of the compound of formula (I), or the pharmaceutically acceptable salt thereof, to the subject once per day in a dose of about 1000 mg.

In another aspect, disclosure relates to a composition comprising a compound of formula (I), or a pharmaceutically acceptable salt thereof, for use in a method of treating or lessening the severity of postsurgical pain in a subject, wherein the composition is prepared for administration of the compound of formula (I), or the pharmaceutically acceptable salt thereof, to the subject once per day in a dose of about 1000 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of postsurgical pain in a subject, wherein the composition is prepared for administration of the compound of formula (I), or the pharmaceutically acceptable salt thereof, to the subject twice per day in a dose of about 500 mg (1000 mg per day).

In another aspect, disclosure relates to a composition comprising a compound of formula (I), or a pharmaceutically acceptable salt thereof, for use in a method of treating or lessening the severity of postsurgical pain in a subject, wherein the composition is prepared for administration of the compound of formula (I), or the pharmaceutically acceptable salt thereof, to the subject in a first dose of about 1500 mg and a subsequent dose of about 750 mg on the first day, and in two doses of about 750 mg per day each day after the first day.

In another aspect, disclosure relates to a composition comprising a compound of formula (I), or a pharmaceutically acceptable salt thereof, for use in a method of treating or lessening the severity of postsurgical pain in a subject, wherein the composition is prepared for administration of the compound of formula (I), or the pharmaceutically acceptable salt thereof, to the subject in a first dose of about 500 mg and a subsequent dose of about 250 mg on the first day, and in two doses of about 250 mg per day each day after the first day.

In another aspect, disclosure relates to a composition comprising a compound of formula (I), or a pharmaceutically acceptable salt thereof, for use in a method of treating or lessening the severity of postsurgical pain in a subject, wherein the composition is prepared for administration of the compound of formula (I), or the pharmaceutically acceptable salt thereof, to the subject once per day in a dose of about 750 mg.

In another aspect, disclosure relates to a composition comprising a compound of formula (I), or a pharmaceutically acceptable salt thereof, for use in a method of treating or lessening the severity of postsurgical pain in a subject, wherein the composition is prepared for administration of the compound of formula (I), or the pharmaceutically acceptable salt thereof, to the subject once per day in a dose of about 750 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of postsurgical pain in a subject, wherein the composition is prepared for administration of the compound of formula (I), or the pharmaceutically acceptable salt thereof, to the subject once per day in a dose of about 1250 mg.

In another aspect, disclosure relates to a composition comprising a compound of formula (I), or a pharmaceutically acceptable salt thereof, for use in a method of treating or lessening the severity of postsurgical pain in a subject, wherein the composition is prepared for administration of the compound of formula (I), or the pharmaceutically acceptable salt thereof, to the subject once per day in a dose of about 1250 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of postsurgical pain in a subject, wherein the composition is prepared for administration of the compound of formula (I), or the pharmaceutically acceptable salt thereof, to the subject once per day in a dose of 750 mg to 1250 mg.

In another aspect, disclosure relates to a composition comprising a compound of formula (I), or a pharmaceutically acceptable salt thereof, for use in a method of treating or lessening the severity of postsurgical pain in a subject, wherein the composition is prepared for administration of the compound of formula (I), or the pharmaceutically acceptable salt thereof, to the subject once per day in a dose of 750 mg to 1250 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of visceral pain in a subject, wherein the composition is prepared for administration of the compound of formula (I), or the pharmaceutically acceptable salt thereof, to the subject.

In another aspect, disclosure relates to a composition comprising a compound of formula (I), or a pharmaceutically acceptable salt thereof, for use in a method of treating or lessening the severity of visceral pain in a subject, wherein the composition is prepared for administration of the compound of formula (I), or the pharmaceutically acceptable salt thereof, to the subject once per day in a dose of about 250 mg.

In another aspect, disclosure relates to a composition comprising a compound of formula (I), or a pharmaceutically acceptable salt thereof, for use in a method of treating or lessening the severity of visceral pain in a subject, wherein the composition is prepared for administration of the compound of formula (I), or the pharmaceutically acceptable salt thereof, to the subject once per day in a dose of about 1000 mg.

In another aspect, disclosure relates to a composition comprising a compound of formula (I), or a pharmaceutically acceptable salt thereof, for use in a method of treating or lessening the severity of visceral pain in a subject, wherein the composition is prepared for administration of the compound of formula (I), or the pharmaceutically acceptable salt thereof, to the subject once per day in a dose of about 1000 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of visceral pain in a subject, wherein the composition is prepared for administration of the compound of formula (I), or the pharmaceutically acceptable salt thereof, to the subject twice per day in a dose of about 500 mg (1000 mg per day).

In another aspect, disclosure relates to a composition comprising a compound of formula (I), or a pharmaceutically acceptable salt thereof, for use in a method of treating or lessening the severity of visceral pain in a subject, wherein the composition is prepared for administration of the compound of formula (I), or the pharmaceutically acceptable salt thereof, to the subject in a first dose of about 1500 mg and a subsequent dose of about 750 mg on the first day, and in two doses of about 750 mg per day each day after the first day.

In another aspect, disclosure relates to a composition comprising a compound of formula (I), or a pharmaceutically acceptable salt thereof, for use in a method of treating or lessening the severity of visceral pain in a subject, wherein the composition is prepared for administration of the compound of formula (I), or the pharmaceutically acceptable salt thereof, to the subject in a first dose of about 500 mg and a subsequent dose of about 250 mg on the first day, and in two doses of about 250 mg per day each day after the first day.

In another aspect, disclosure relates to a composition comprising a compound of formula (I), or a pharmaceutically acceptable salt thereof, for use in a method of treating or lessening the severity of visceral pain in a subject, wherein the composition is prepared for administration of the compound of formula (I), or the pharmaceutically acceptable salt thereof, to the subject once per day in a dose of about 750 mg.

In another aspect, disclosure relates to a composition comprising a compound of formula (I), or a pharmaceutically acceptable salt thereof, for use in a method of treating or lessening the severity of visceral pain in a subject, wherein the composition is prepared for administration of the compound of formula (I), or the pharmaceutically acceptable salt thereof, to the subject once per day in a dose of about 750 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of visceral pain in a subject, wherein the composition is prepared for administration of the compound of formula (I), or the pharmaceutically acceptable salt thereof, to the subject once per day in a dose of about 1250 mg.

In another aspect, disclosure relates to a composition comprising a compound of formula (I), or a pharmaceutically acceptable salt thereof, for use in a method of treating or lessening the severity of visceral pain in a subject, wherein the composition is prepared for administration of the compound of formula (I), or the pharmaceutically acceptable salt thereof, to the subject once per day in a dose of about 1250 mg, for at least one week, at least two weeks, at least three weeks, at least four weeks, at least five weeks, or at least six weeks, or from one to six weeks.

In another aspect, disclosure relates to a composition comprising a compound of formula (I), or a pharmaceutically acceptable salt thereof, for use in a method of treating or lessening the severity of visceral pain in a subject, wherein the composition is prepared for administration of the compound of formula (I), or the pharmaceutically acceptable salt thereof, to the subject once per day in a dose of 750 mg to 1250 mg.

In another aspect, disclosure relates to a composition comprising a compound of formula (I), or a pharmaceutically acceptable salt thereof, for use in a method of treating or lessening the severity of visceral pain in a subject, wherein the composition is prepared for administration of the compound of formula (I), or the pharmaceutically acceptable salt thereof, to the subject once per day in a dose of 750 mg to 1250 mg, for at least one week, at least two weeks, at least three weeks, at least four weeks, at least five weeks, or at least six weeks, or from one to six weeks.

Manufacture of Medicaments

In another aspect, the disclosure relates to the use of the compound of formula (I), or a pharmaceutically acceptable salt or pharmaceutical composition thereof, for the manufacture of a medicament for treating or lessening the severity of pain in a subject in accordance with the method described herein (including any embodiment thereof).

Pharmaceutically Acceptable Salts, Pharmaceutical Compositions, Dosage Forms and Routes of Administration Pharmaceutically Acceptable Salts The methods described and claimed herein comprise administering to a subject a compound of formula (I), or a pharmaceutically acceptable salt thereof. As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" of the compound of formula (I) includes any non-toxic salt that, upon administration to a recipient, is capable of providing, either directly or indirectly, the compound of formula (I) or an inhibitorily active metabolite or residue thereof (e.g., the parent compound of a prodrug). As used herein, the term "inhibitorily active metabolite or residue thereof" means that a metabolite or residue thereof is also an inhibitor of a voltage-gated sodium channel. The compound of formula (I) is a prodrug of 2-(4-fluoro-2-methylphenoxy)-N-(2-oxo-1,2-dihydropyridin-4-yl)-4-(trifluoromethyl)benzamide, which is described in U.S. Publication No. 2014/0213616 A1. A "pharmaceutically acceptable salt" of the compound of formula (I) includes without limitation any non-toxic salt that, upon administration to a recipient, is capable of providing, either directly or indirectly, the compound of formula (I) or 2-(4-fluoro-2-methylphenoxy)-N-(2-oxo-1,2-dihydropyridin-4-yl)-4-(trifluoromethyl)benzamide.

Pharmaceutically acceptable salts are well known in the art. For example, S. M. Berge, et al. describe pharmaceutically acceptable salts in detail in *J. Pharmaceutical Sciences*, 1977, 66, 1-19, incorporated herein by reference. Pharmaceutically acceptable salts of the compound of formula (I) include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, and ammonium salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Pharmaceutical Compositions

In the methods described and claimed herein, the compound of formula (I), or a pharmaceutically acceptable salt thereof, may be administered in the form of a pharmaceutical composition comprising the compound of formula (I), or a pharmaceutically acceptable salt thereof, and a pharmaceutically acceptable carrier, adjuvant or vehicle.

The term "pharmaceutically acceptable carrier, adjuvant, or vehicle" includes any and all solvents, diluents, or other liquid vehicles, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compound of formula (I), or a pharmaceutically acceptable salt thereof, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Dosage Forms and Routes of Administration

The methods described and claimed herein may involve the administration of the compound of formula (I), or a pharmaceutically acceptable salt thereof, by any route of administration effective for treating or lessening the severity of one or more of the pain diseases recited herein. The compound of formula (I), or a pharmaceutically acceptable salt thereof, may be formulated in dosage unit form for ease of administration and uniformity of dosage. The term "dosage unit form," as used herein, refers to a physically discrete unit of agent appropriate for the subject to be treated.

The compound of formula (I), or pharmaceutically acceptable salt thereof, can be administered to humans and other animals orally, rectally, parenterally, intracisternally, intravaginally, intraperitoneally, topically (as by powders, ointments, or drops), bucally, as an oral or nasal spray, or the like, depending on the condition being treated.

Liquid dosage forms for oral administration include, but are not limited to, pharmaceutically acceptable emulsions, microemulsions, solutions, suspensions, syrups and elixirs. In addition to the compound of formula (I), or a pharmaceutically acceptable salt thereof, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of the compound of formula (I), it may be desirable to slow the absorption of the compound, or a pharmaceutically acceptable salt thereof, from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microcapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compound of formula (I), or a pharmaceutically acceptable salt thereof, with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the compound of formula (I), or a pharmaceutically acceptable salt thereof, is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

The active compound or salt can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound or salt may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of the compound of formula (I), or a pharmaceutically acceptable salt thereof, include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

EXAMPLES

Abbreviations

Unless otherwise noted, or where the context dictates otherwise, the following abbreviations shall be understood to have the following meanings:

| Abbreviation | Definition |
| --- | --- |
| TPGS | tocopherol polyethylene glycol succinate |
| HB/APAP | hydrocodone bitartrate/acetaminophen |
| NPRS | Numeric Pain Rating Scale |
| VRS | Verbal Categorical Rating Scale |
| q24h | every 24 hours |
| q12h | every 12 hours |
| q6h | every 6 hours |
| n | number of subjects meeting a specified criterion |
| n (%) | number of subjects meeting a specified criterion (percentage of the total number of subjects in study arm meeting that criterion) |
| SPID24 | NPRS pain intensity difference, relative to baseline, from 0 to 24 hours after the first dose for a given study arm |
| SD | standard deviation |
| SE | standard error |
| CI | confidence interval |
| SPID22 | NPRS pain intensity difference, relative to baseline, from 2 to 24 hours after the first dose for a given study arm |
| SPID48 | NPRS pain intensity difference, relative to baseline, from 0 to 48 hours after the first dose for a given study arm |
| $C_{max}$ | maximum observed concentration |
| $AUC_\tau$ | area under the curve over a dosing interval ($\tau$) |
| TEAE | treatment-emergent adverse event |

Example 1

Preparation of (4-(2-(4-fluoro-2-methylphenoxy)-4-(trifluoromethyl)benzamido)-2-oxopyridin-1(2H)-yl)methyl dihydrogen phosphate (Compound 1)

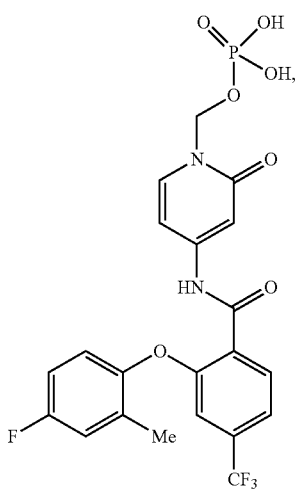

A synthesis of (4-(2-(4-fluoro-2-methylphenoxy)-4-(trifluoromethyl)benzamido)-2-oxopyridin-1(2H)-yl)methyl dihydrogen phosphate (Compound 1) is described in Examples 6, 13, 14, 15, and 15A-15F of U.S. Pat. No. 9,163,042, which Examples are incorporated herein by reference.

Figure 2:
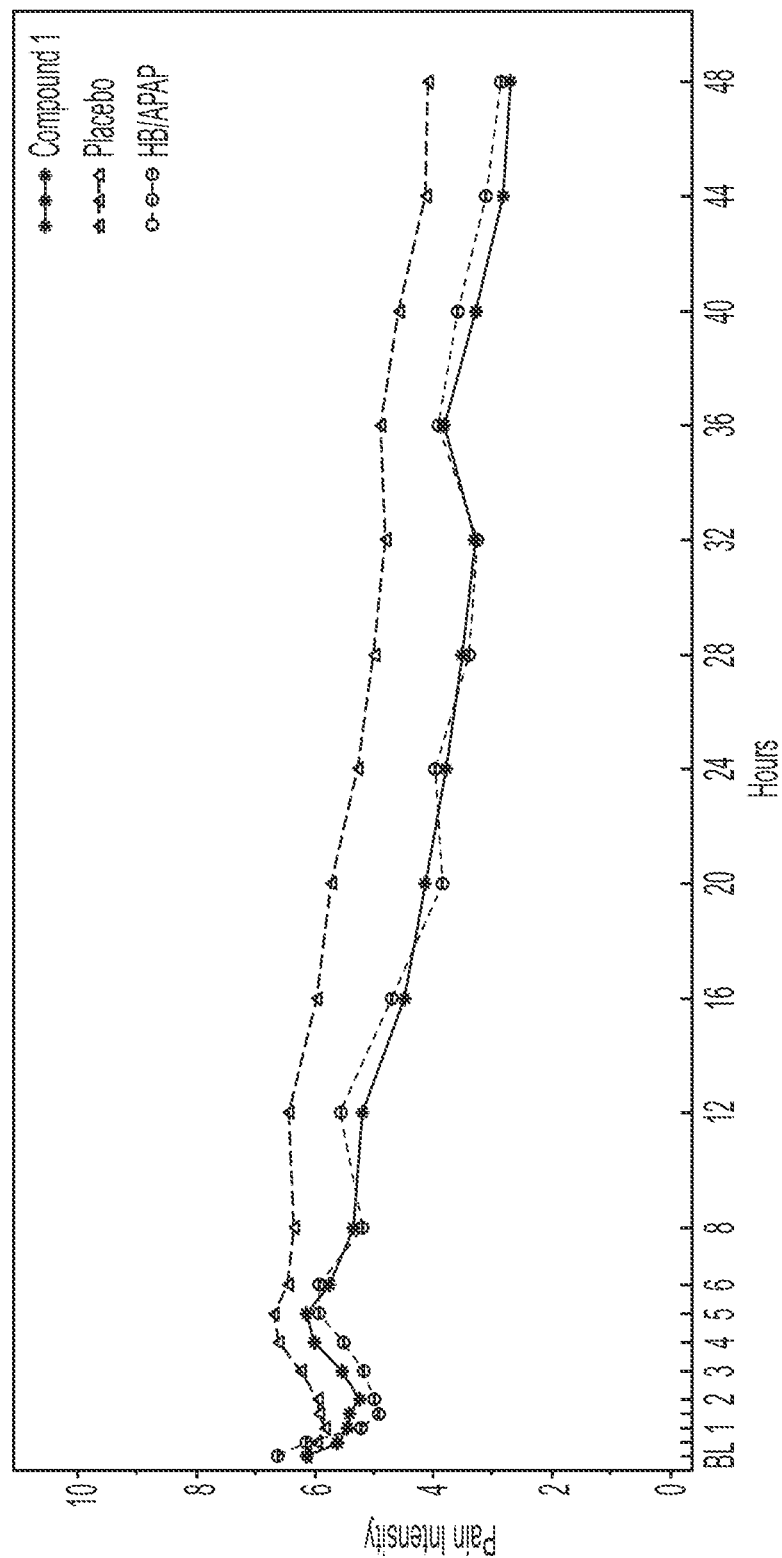
FIG. 2 is plot of mean NPRS pain intensity score versus time for subjects in the Investigational, Reference, and Placebo Arms of the clinical study described in Example 3.
Figure 3:
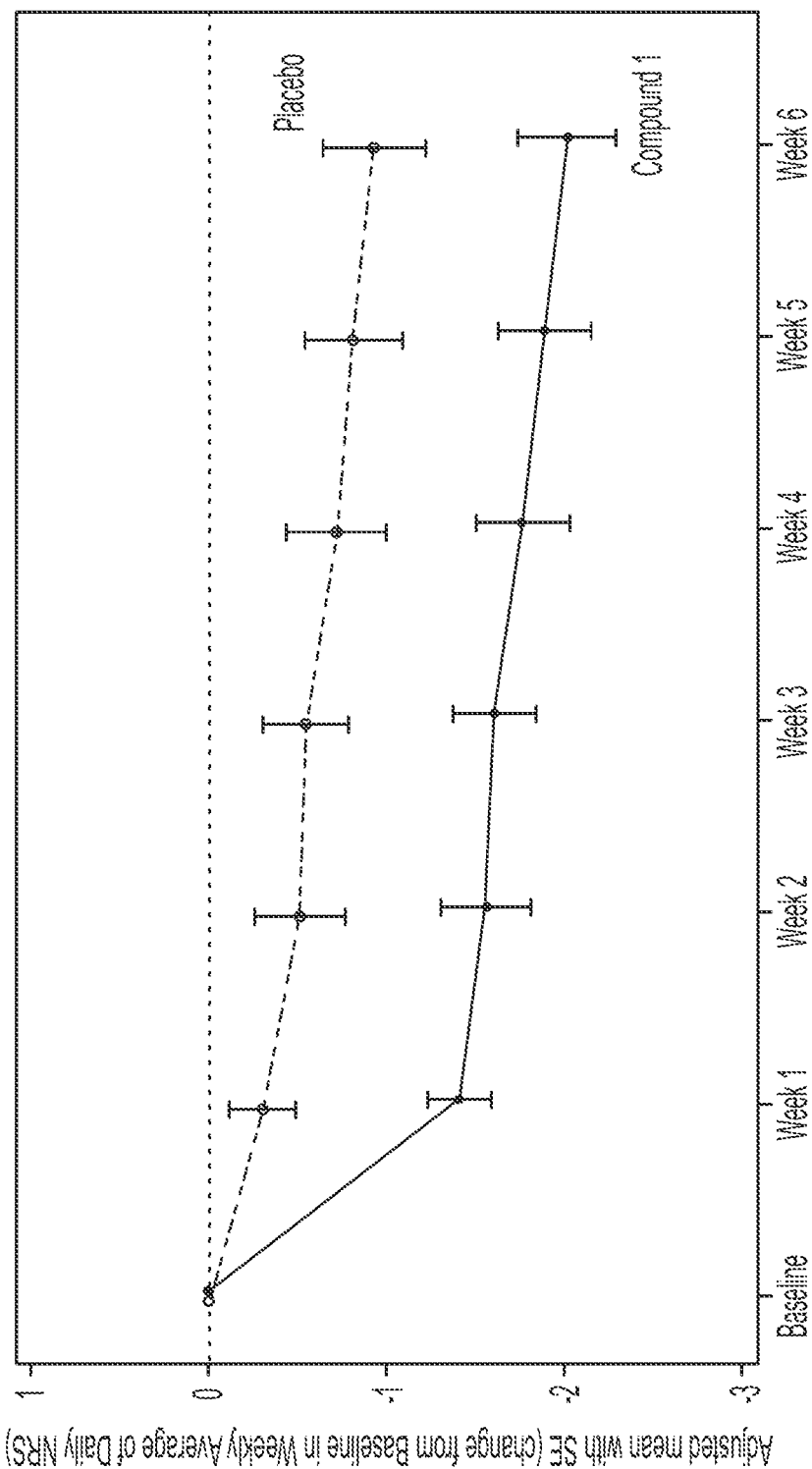
FIG. 3 is a plot of the adjusted mean change from baseline in the weekly average of daily pain intensity for subjects in the Treatment and Placebo Arms of the clinical study described in Example 5.

Form B of Compound 1, including the preparation and characterization thereof, is described in U.S. Pat. No. 9,163,042, column 20, line 47, to column 25, line 53; column 26, lines 39-51; and FIGS. 2 to 4, which passages and figures are incorporated herein by reference.

Example 2

Capsule Dosage Form of Compound 1

Capsules were manufactured at a dose strength of 250 mg of Compound 1 wherein tocopherol polyethylene glycol succinate (TPGS) was melted overnight at 50±5° C. in an oven. The melted TPGS and Form B of Compound 1 were added to a Skerman mixer to form a suspension. Once a homogeneous dispersion was formed, it was held at 50±5° C. and filled in hydroxypropyl methylcellulose Vcaps® 00EL capsules (Capsugel) using a Bosch 1500L automatic capsule filling machine. Each capsule contained 250 mg of Compound 1 and 750 mg of TPGS.

Example 3

A Study of the Efficacy and Safety of Compound 1 in Subjects with Pain Following Bunionectomy A randomized, double-blind, placebo-controlled, 3-arm, parallel-design study to evaluate the effect of Compound 1 on acute surgical pain was conducted. Bunionectomy is a well-established, multi-dose, surgical, acute pain model. A randomized, double-blind study design was selected to avoid observer bias and reduce symptoms or outcomes arising from the subjects' knowledge of treatment. A parallel design was considered most appropriate given the acute nature of bunionectomy surgery. An opioid reference arm assessing a standard-of-care treatment (hydrocodone bitartrate/acetaminophen (HB/APAP)) was included to establish the ability of the study, as executed, to successfully observe a treatment effect for Compound 1.

Study Subjects

Male and female patients between the ages of 18 and 65 years (inclusive) with pain that is ≥4 on an 11-point Numeric Pain Rating Scale (NPRS) and is moderate or severe on the Verbal Categorical Rating Scale (VRS) after bunionectomy.

Study Drugs

Investigational Drug: Compound 1. The investigational drug was administered orally in 250 mg capsules, prepared as described in Example 2. The investigational drug was administered every 12 hours (q12 h). The first dose was 1500 mg, and the remaining doses were 750 mg.

Reference Drug: HB/APAP. The reference drug was administered orally in 5 mg/325 mg capsules, supplied as over-encapsulated 5 mg/325 mg tablets. The reference drug was administered in a dose of 5 mg/325 mg every 6 hours (q6 h).

Study Protocol

The schedule for the study is summarized in Table 1. After a screening period, subjects received a primary unilateral first metatarsal bunionectomy repair on Day −1. A continuous popliteal sciatic block infusion (0.2% ropivacaine) was started after surgery, and remained in place until approximately 3 AM on Day 1. After removal of the popliteal sciatic block, each subject was randomized when the subject requested the first dose of study drug for pain relief and reported pain ≥4 on the NPRS and moderate or severe pain on the VRS. The NPRS and VRS criteria were designed to ensure subjects had sufficient pain to determine if the study drugs are effective. Subjects that did not meet the NPRS and VRS criteria within 9 hours of removal of the popliteal sciatic block were not enrolled in the study.

A total of 243 subjects were randomized approximately 1:1:1 to the Investigational Arm (80 subjects), Reference Arm (81 subjects), and Placebo Arm (82 subjects). To maintain the blind, all subjects received the same number of capsules in a double-dummy design.

In the Investigational Arm, Compound 1 was administered every 12 hours (q12 h) in a first dose of 1500 mg, followed by three 750 mg doses. The final dose of Compound 1 was given 36 hours after the first dose. HB/APAP placebo capsules were administered every 6 hours (q6 h).

In the Reference Arm, HB/APAP was administered every 6 hours (q6 h) at a dose of 5 mg/325 mg. The final dose of HB/APAP was given 42 hours after the first dose. Compound 1 placebo capsules were administered every 12 hours (q12 h).

In the Placebo Arm, Compound 1 placebo capsules were administered every 12 hours (q12 h), and HB/APAP placebo capsules were administered every 6 hours (q6 h).

Subjects had a Safety Follow-up Phone Interview 7 (±2) days after the last study drug dose for the purpose of collecting information on adverse events, medications, and treatments and procedures.

TABLE 1

Study Schedule

| Study Day | Event |
| --- | --- |
| Day -28 | Beginning of screening period |
| Day -1 | Bunionectomy |
| Day 1 (approximately 3 AM) | Removal of popliteal block |
| Day 1 | Randomization |
| Days 1-3 | Administration of study drug |
| Days 8-12 | Safety follow-up phone interview |

Disposition of Study Subjects

Of the 80 subjects assigned to the Investigational Arm, 74 (92.5%) completed the study treatment, and 6 (7.5%) discontinued due to lack of efficacy.

Of the 81 subjects assigned to the Reference Arm, 77 (95.1%) completed the study treatment, and 4 (4.9%) discontinued due to lack of efficacy.

Of the 82 subjects assigned to the Placebo Arm, 75 (91.5%) completed the study treatment, and 7 (8.5%) discontinued due to lack of efficacy.

Efficacy Assessments 11-point (0 to 10) Numeric Pain Rating Scale: NPRS scores are frequently used in bunionectomy studies and are recognized by the FDA as a valid pain intensity measure. On the 11-point NPRS, a score of 0 denoted no pain, and a score of 10 denoted the worst pain intensity imaginable. Subjects reported their pain on the 11-point NPRS immediately before their first dose of the study drug (baseline NPRS score) and 0.5, 1, 1.5, 2, 3, 4, 5, 6, 8, 12, 16, 20, 24, 28, 32, 36, 40, 44, and 48 hours (±5 minutes) after the first dose of study drug. Pain intensity also was recorded on the NPRS immediately before each administration of rescue medication. Pain intensity scores that were collected within 4 hours after a dose of rescue medication were taken as missing, and the missing values were imputed as the intensity recorded immediately before the administration of rescue medication.

4-point Verbal Categorical Rating Scale: Subjects reported their pain on the 4-point VRS (none, mild, moderate, or severe) immediately before their first dose of the study drug (baseline VRS).

Efficacy Results

Baseline NPRS and VRS Scores. The baseline NPRS and VRS scores for the subjects in the Placebo Arm, Investigational Arm, and Reference Arm are reported in Table 2. The NPRS scores reflect the mean (and standard deviation) of the NPRS scores of the subjects in each arm. The VRS scores reflect the number (and percentage) of subjects reporting "Moderate" and "Severe" pain at baseline in each arm.

TABLE 2

Baseline Pain Scores

| | Placebo Arm | Investigational Arm | Reference Arm |
| --- | --- | --- | --- |
| Baseline NPRS Score, Mean (SD) | 6.1 (1.5) | 6.1 (1.7) | 6.6 (1.6) |
| Baseline VRS Score (n (%)) | | | |
| Moderate | 62 (75.6) | 58 (72.5) | 49 (60.5) |
| Severe | 20 (24.4) | 20 (25.0) | 32 (39.5) |

NPRS Scores During Administration of Study Drugs. The mean NPRS for each study arm at each time point between 0 and 48 hours after first dose of study drug is depicted graphically in FIG. 2.

Time-Weighted Sums of Pain Intensity Differences.

The primary efficacy analysis was based on an analysis of covariance (ANCOVA) model. The Least Squares (LS) mean of the time-weighted sum of the NPRS pain intensity difference, relative to baseline, from 0 to 24 hours after the first dose ("SPID24") for each study arm is reported in Table 3. SPID24 is a standard measure of acute pain. Higher SPID24 scores represent improvements in pain relief. "Treatment difference" refers to the difference in SPID24 between the Investigational and Reference Arms, respectively, and the Placebo Arm.

Treatment with Compound 1 (in the Investigational Arm) showed statistically significant relief of acute pain compared to placebo, as demonstrated by a statistically significant increase in SPID24 compared to placebo. The pain relief observed after treatment with Compound 1 was also similar to that seen for HB/APAP (in the Reference Arm), as demonstrated by the SPID24 scores.

TABLE 3

SPID24 in Placebo, Investigational, and Reference Arms

| | Placebo Arm | Investigational Arm | Reference Arm |
| --- | --- | --- | --- |
| SPID24 (SE) | 6.64 (5.03) | 36.14 (5.15) | 40.16 (5.08) |
| Treatment difference | — | 29.50 | 33.52 |
| Treatment difference (95% CI) | — | (16.61, 42.40) | (20.61, 46.43) |
| P-value | — | <0.0001 | <0.0001 |

The LS mean of the time-weighted sum of the NPRS pain intensity difference, relative to baseline, from 2 to 24 hours after the first dose ("SPID22") for each study arm is reported in Table 4. The analysis was based on an analysis of covariance (ANCOVA) model. "Treatment difference" refers to the difference in SPID22 between the Investigational and Reference Arms, respectively, and the Placebo Arm.

TABLE 4

SPID22 in Placebo, Investigational, and Reference Arms

| | Placebo Arm | Investigational Arm | Reference Arm |
| --- | --- | --- | --- |
| SPID22 (SE) | 6.43 (4.82) | 34.95 (4.93) | 37.87 (4.87) |
| Treatment difference | — | 28.53 | 31.44 |
| Treatment difference (95% CI) | — | (16.18, 40.88) | (19.08, 43.81) |
| P-value | — | <0.0001 | <0.0001 |

The LS mean of the time-weighted sum of the NPRS pain intensity difference, relative to baseline, from 0 to 48 hours after the first dose ("SPID48") for each study arm is reported in Table 5. The primary efficacy analysis was based on an analysis of covariance (ANCOVA) model. "Treatment difference" refers to the difference in SPID48 between the Investigational and Reference Arms, respectively, and the Placebo Arm.

TABLE 5

SPID48 in Placebo, Investigational, and Reference Arms

| | Placebo Arm | Investigational Arm | Reference Arm |
|---|---|---|---|
| SPID48 (SE) | 49.43 (10.33) | 112.22 (10.57) | 116.80 (10.44) |
| Treatment difference | — | 62.79 | 67.38 |
| Treatment difference (95% CI) | — | (36.30, 89.27) | (40.86, 93.89) |
| P-value | — | <0.0001 | <0.0001 |

NPRS Responder Analysis. The number and percentage of subjects in each study arm achieving ≥30%, ≥50%, and ≥70% NPRS pain intensity reductions, relative to baseline, at 24 hours after the first dose are reported in Table 6. Responder rates were analyzed using the Cochran-Mantel-Haenszel test.

TABLE 6

Number and Percentage of Subjects Achieving Percentage NPRS Reductions

| NPRS Reduction at 24 hours | Placebo Arm (82 subjects) | Investigational Arm (80 subjects) | Reference Arm (81 subjects) |
|---|---|---|---|
| ≥30% (n (%)) | 26 (31.7) | 46 (57.5) | 51 (63.0) |
| P-value | — | 0.0007 | <0.0001 |
| ≥50% (n (%)) | 20 (24.4) | 41 (51.3) | 44 (54.3) |
| P-value | — | 0.0004 | <0.0001 |
| ≥70% (n (%)) | 8 (9.8) | 22 (27.5) | 18 (22.2) |
| P-value | — | 0.0026 | 0.0315 |

Safety Results

Safety evaluations included adverse events, clinical laboratory assessments, clinical evaluation of vital signs, electrocardiograms, and physical examinations. The study demonstrated that Compound 1 was generally well tolerated. More than 90 percent of patients in each arm of the study completed treatment. There were no discontinuations due to adverse events, and there were no serious adverse events in any arm of the study. The majority of adverse events were mild or moderate.

Treatment emergent adverse events (TEAEs) were largely consistent with typical post-operative adverse events in the study population. Gastrointestinal adverse events were more common in the Reference Arm (24%) compared to the Investigational Arm (13%) or Placebo Arm (16%).

Example 4

A Dose-Ranging Study to Evaluate the Efficacy and Safety of Compound 1 in Subjects with Acute Pain Following Bunionectomy A randomized, double-blind, placebo-controlled, dose-ranging, parallel-design study will be conducted to evaluate the dose response of the efficacy of Compound 1 in treating acute pain following bunionectomy. Bunionectomy is a well-established, multi-dose, surgical, acute pain model. A randomized, double-blind study design was selected to avoid observer bias and reduce symptoms or outcomes arising from the subjects' knowledge of treatment. A parallel design was considered most appropriate given the acute nature of bunionectomy surgery.

Study Subjects

Male and female subjects who are between the ages of 18 and 65 years (inclusive) with pain that is ≥4 on the 11-point Numeric Pain Rating Scale (NPRS) and is moderate or severe on the Verbal Categorical Rating Scale (VRS) after bunionectomy.

Study Drug

Investigational Drug: Compound 1. The investigational drug will be administered orally in 250 mg capsules, prepared as described in Example 2.

Study Protocol

Subjects will receive a primary unilateral first metatarsal bunionectomy repair on Day −1. A continuous popliteal sciatic block infusion (0.2% ropivacaine) will be started after surgery, and will be removed between 3 AM and 5 AM on Day 1. After removal of the popliteal sciatic block, a subject can be randomized once the subject requests the first dose of study drug for pain relief, and the subject's pain is ≥4 on the NPRS and is moderate or severe on the VRS. If a subject does not meet the NPRS and VRS criteria within 9 hours of removal of the popliteal sciatic block, the subject will not be eligible to enroll in the study.

The subjects will be randomized to 4 investigational arms:

Investigational Arm 1: Compound 1 will be administered every 24 hours (q24 h) in a dose of 250 mg. The final dose of Compound 1 will be given 24 hours after the first dose.

Investigational Arm 2: Compound 1 will be administered every 12 hours (q12 h) in a first dose of 500 mg, followed by three 250 mg doses. The final dose of Compound 1 will be given 36 hours after the first dose.

Investigational Arm 3: Compound 1 will be administered every 24 hours (q24 h) in a dose of 1000 mg. The final dose of Compound 1 will be given 24 hours after the first dose.

Investigational Arm 4: Compound 1 will be administered every 12 hours (q12 h) in a dose of 500 mg. The final dose of Compound 1 will be given 36 hours after the first dose.

Assessments 11-point (0 to 10) Numeric Pain Rating Scale: Subjects will report their pain on the 11-point NPRS immediately before their first dose of the study drug (baseline NPRS score) and throughout the study after the first dose of study drug.

4-point Verbal Categorical Rating Scale: Subjects will report their pain on the 4-point VRS (none, mild, moderate, or severe) immediately before their first dose of the study drug (baseline VRS).

Pharmacokinetic Parameters: Blood samples will be collected, and plasma pharmacokinetic parameters of 2-(4-fluoro-2-methylphenoxy)-N-(2-oxo-1,2-dihydropyridin-4-yl)-4-(trifluoromethyl)benzamide, the parent compound of Compound 1, will be determined by noncompartmental analysis and described using summary statistics.

Study Endpoints

The primary endpoint will be the time-weighted sum of the pain intensity difference between Compound 1 versus placebo as recorded on a Numeric Pain Rating Scale (NPRS) 0 to 48 hours (SPID48) after the first dose. Upon the detection of dose-response relationship, pairwise comparison in SPID48 between Compound 1 and placebo will be further conducted using an analysis of covariance (ANCOVA) model.

A secondary endpoint will be the time-weighted sum of the pain intensity difference between each dose level of Compound 1 versus placebo as recorded on a NPRS 0 to 24 hours (SPID24) after the first dose.

A secondary endpoint will be the proportions of subjects with at least 30%, 50%, or 70% reductions in NPRS at 24 hours after the first dose of Compound 1 versus placebo.

A secondary endpoint will be the plasma PK parameters of 2-(4-fluoro-2-methylphenoxy)-N-(2-oxo-1,2-dihydropyridin-4-yl)-4-(trifluoromethyl)benzamide, the parent compound of Compound 1.

A secondary endpoint will be the safety and tolerability based on the incidence and type of adverse events (AEs), changes from baseline in clinically significant laboratory test results, and vital signs at designated visits.

Example 5

A Study to Evaluate the Efficacy and Safety of Compound 1 for the Treatment of Pain Caused by Small Fiber Neuropathy A randomized, double-blind, placebo-controlled, 6-week study that evaluated treatment with Compound 1 (Treatment Arm) or placebo (Placebo Arm) in patients with chronic pain caused by small fiber neuropathy was conducted.

Study Subjects

Males and females between the ages of 18 and 80 years, inclusive, with small fiber neuropathy.

Study Drug

Compound 1 was administered orally in 250 mg capsules, prepared as described in Example 2.

Study Protocol

The study included a 7-day run-in period, followed a 6-week treatment period. The subjects were randomized to a Placebo Arm (43 subjects) and a Treatment Arm (46 subjects) between the run-in period and the treatment period.

During the run-in period, subjects reported their average pain and sleep interference to establish a baseline NRS pain score and DSIS score.

During the treatment period, Compound 1 was administered to the subjects in the Treatment Arm every 24 hours (q24 h) in a dose of 1250 mg. Subjects in the Placebo Arm received placebo capsules.

Efficacy Assessments 11-point Numeric Rating Scale (NRS). Pain intensity was evaluated using an 11-point NRS. The 11-point scale ranged from 0 (no pain) to 10 (worst imaginable pain). From Day −7 through Week 6, subjects reported their average daily pain during the last 24 hours on the NRS via electronic diary.

Daily Sleep Interference Scale (DSIS). Subjects reported pain interference with sleep using an 11-point scale ranging from 0 (none) to 10 (severe). The DSIS score was reported each morning in an electronic diary.

Patient Global Impression of Change (PGIC). Subjects' impressions of their overall health status were reported on a 7-point scale from 1 (very much improved) to 7 (very much worse) at study visits.

Efficacy Results

Change from Baseline Pain Intensity. NRS pain scores were averaged over weekly periods to reduce the impact on the analyses of individual high or low pain scores. The mean change from baseline in the weekly average of daily pain intensity on the 11-point NRS over the course of the treatment period for subjects in the Placebo and Treatment Arms is depicted graphically in FIG. 3. The mean change at Week 6 is reported in Table 7. The mean change from baseline for those treated with Compound 1 compared to placebo was −1.09 (95% CI: −1.88 to −0.29) at Week 6. A treatment difference of greater than 1 point was observed as early as Week 1, demonstrating pain relief as early as the first week of treatment that was sustained through the six-week treatment period.

TABLE 7

Mean Change from Baseline Pain Intensity

|  | Placebo Arm | Treatment Arm |
| --- | --- | --- |
| Baseline (SD) | 5.99 (1.41) | 6.43 (1.44) |
| Mean change from baseline NRS at week 6 (SE) | −0.93 (0.29) | −2.02 (0.27) |
| Mean change from baseline, 95% confidence interval | (−1.50, −0.36) | (−2.56, −1.47) |
| Within-group P-value | 0.0017 | <0.0001 |

Change from Baseline in Daily Sleep Interference Scale. The mean change from baseline in the weekly average of DSIS score at Week 6 for subjects in the Placebo and Treatment Arms is reported in Table 8.

TABLE 8

Change from Baseline on Daily Sleep Interference Scale

|  | Placebo Arm | Treatment Arm |
| --- | --- | --- |
| Baseline | 5.10 | 5.94 |
| Mean change from baseline (SE) | −0.67 (0.29) | −1.78 (0.28) |

NRS Responder Rate Analysis. The number and percentage of subjects with ≥30% and ≥50% reduction in the weekly average of daily pain intensity on the 11-point NRS at Week 6 is reported in Table 9. The total number of subjects for determining the percentage was based on subjects who had data at Week 6.

TABLE 9

Number and Percentage of Subjects Achieving Percentage NRS Reductions

|  | Placebo Arm % (n/Total) | Treatment Arm % (n/Total) |
| --- | --- | --- |
| ≥30% | 26.5% (9/34) | 45.0% (18/40) |
| ≥50% | 17.6% (6/34) | 32.5% (13/40) |

Proportion of Subjects Categorized as Improved. The number and percentage of subjects categorized as improved on the PGIC assessment at Week 6 is reported in Table 10. The total number of subjects for determining the percentage was based on subjects who had data at Week 6.

TABLE 10

Number and Percentage of Subjects Categorized as Improved

|  | Placebo Arm % (n/Total) | Treatment Arm % (n/Total) |
| --- | --- | --- |
| Improved | 13.5% (5/37) | 39.5% (17/43) |

Many modifications and variations of the embodiments described herein may be made without departing from the scope, as is apparent to those skilled in the art. The specific embodiments described herein are offered by way of example only.

What is claimed is:

1. A method of treating or lessening the severity of pain in a subject, comprising administering to the subject orally a compound of formula (I)

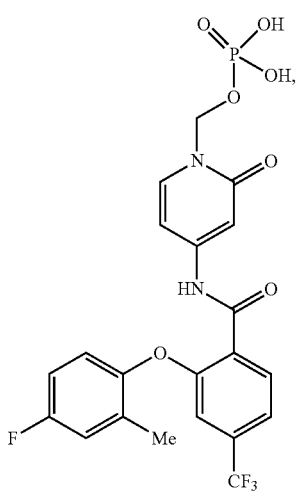

or a pharmaceutically acceptable salt thereof, wherein:

(a) the compound of formula (I), or a pharmaceutically acceptable salt thereof, is administered every 12 hours in a first dose of 1500 mg and a subsequent dose of 750 mg; or (b) the compound of formula (I), or a pharmaceutically acceptable salt thereof, is administered every 12 hours in a first dose of 500 mg and a subsequent dose of 250 mg.

2. The method of claim 1, wherein the compound of formula (I), or a pharmaceutically acceptable salt thereof, is administered every 12 hours in a first dose of 1500 mg and a subsequent dose of 750 mg.

3. The method of claim 2, wherein the pain is acute pain.

4. The method of claim 3, wherein the acute pain is acute post-operative pain.

5. The method of claim 2, wherein the pain is postsurgical pain.

6. The method of claim 5, wherein the postsurgical pain is bunionectomy pain.

7. The method of claim 1, wherein the compound of formula (I), or a pharmaceutically acceptable salt thereof, is administered every 12 hours in a first dose of 500 mg and a subsequent dose of 250 mg.

8. The method of claim 7, wherein the pain is acute pain.

9. The method of claim 8, wherein the acute pain is acute post-operative pain.

10. The method of claim 7, wherein the pain is postsurgical pain.

11. The method of claim 10, wherein the postsurgical pain is bunionectomy pain.

* * * * *